US011008358B2

(12) United States Patent
Myers et al.

(10) Patent No.: US 11,008,358 B2
(45) Date of Patent: May 18, 2021

(54) SYNTHESIS OF DESOSAMINES

(71) Applicant: President and Fellows of Harvard College, Cambridge, MA (US)

(72) Inventors: Andrew G. Myers, Boston, MA (US); Ziyang Zhang, San Francisco, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/724,654

(22) Filed: Dec. 23, 2019

(65) Prior Publication Data

US 2020/0347087 A1 Nov. 5, 2020

Related U.S. Application Data

(63) Continuation of application No. 15/558,910, filed as application No. PCT/US2016/024210 on Mar. 25, 2016, now Pat. No. 10,544,182.

(60) Provisional application No. 62/138,168, filed on Mar. 25, 2015.

(51) Int. Cl.
| C07H 15/12 | (2006.01) |
| C07H 17/02 | (2006.01) |
| C07H 11/02 | (2006.01) |
| C07H 15/18 | (2006.01) |
| C07C 201/12 | (2006.01) |
| C07C 201/14 | (2006.01) |
| C07H 1/00 | (2006.01) |

(52) U.S. Cl.
CPC ........... *C07H 15/12* (2013.01); *C07C 201/12* (2013.01); *C07C 201/14* (2013.01); *C07H 1/00* (2013.01); *C07H 11/02* (2013.01); *C07H 15/18* (2013.01); *C07H 17/02* (2013.01); *C07B 2200/07* (2013.01)

(58) Field of Classification Search
CPC .......... C07H 15/12; C07H 15/18; C07H 1/00; C07H 11/02; C07H 17/02
See application file for complete search history.

(56) References Cited

U.S. PATENT DOCUMENTS

| 10,544,182 B2 | 1/2020 | Myers et al. |
| 2018/0111956 A1 | 4/2018 | Myers et al. |

FOREIGN PATENT DOCUMENTS

| CN | 102690297 A | 9/2012 | |
| EP | 1950219 A1 | 7/2008 | |
| WO | WO 2007/043710 A1 | 4/2007 | |
| WO | WO-2007099392 A2 * | 9/2007 | ............... C07H 1/00 |
| WO | WO 2008/099368 A1 | 8/2008 | |
| WO | WO 2014/165792 A2 | 10/2014 | |
| WO | WO 2009/023196 A1 | 2/2019 | |

OTHER PUBLICATIONS

Mochalin et al., Chem. Heterocycl. Compd., 1977, 13, p. 699-709. (Year: 1977).*
CN 201680025578.X, Jan. 21, 2020, Chinese Office Action.
EP 16769766.3, Feb. 1, 2019, Extended European Search Report.
JP 2017-550180, May 11, 2020, Japanese Office Action.
PCT/US2016/024210, Aug. 12, 2016, International Search Report and Written Opinion.
PCT/US2016/024210, Oct. 5, 2017, International Preliminary Report on Patentability.
Chinese Office Action in connection with Application No. CN 201680025578.X dated Jan. 21, 2020.
Extended European Search Report in connection with Application No. EP 16769766 dated Feb. 1, 2019.

(Continued)

*Primary Examiner* — Jonathan S Lau
(74) *Attorney, Agent, or Firm* — Wolf, Greenfield & Sacks, P.C.

(57) ABSTRACT

The present invention provides desosamine and mycaminose analogs and nitro sugars and methods for their preparation. The invention also provides methods of cyclizing a compound of Formula (A') with glyoxal to give a nitro sugar of Formula (B). Methods for the preparation of compound of Formula (D') are provided comprising cyclization of a nitro alcohol to give a nitro sugar and reduction and alkylation of the nitro sugar to give a desosamine, mycaminose, or an analog thereof.

(A)

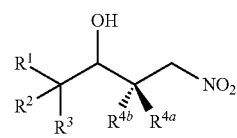

(B)

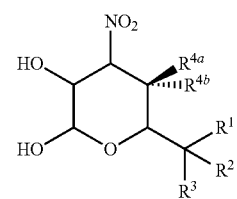

(D')

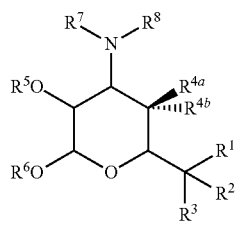

20 Claims, 1 Drawing Sheet

(56) References Cited

OTHER PUBLICATIONS

Japanese Office Action in connection with Application No. JP 2017-550180 dated May 11, 2020.
International Search Report in connection with Application No. PCT/US2016/024210, dated Aug. 12, 2016.
International Preliminary Report on Patentability in connection with Application No. PCT/US2016/024210, dated Oct. 5, 2017.
[No Author Listed] CID 10839468, dated Oct. 26, 2006. 1 page.
Baer et al., Carbohydrate components for modified anthracyclines: synthesis of derivatives of 3-amino-3,4,6-trideoxy-L-lyxo- and -L-xylo-hexose, and attempts at fluorination of C-2 [published correction appears in Carbohydr Res Aug. 1, 1989;191(1):c1]. Carbohydr Res. 1988;184:151-161.
Baer et al., A Stereospecific Synthesis of L-Desosamine. Canadian Journal of Chemistry, 1974;52(1):122-4. doi.org/10.1139/v74-017.
Baer et al., Reactions of nitro sugars. V. Some reactions with methyl 3-deoxy-3-nitro-α-d-hexopyranoside. Canadian Journal of Chemistry, 1967;45(9): 983-990, https://doi.org/10.1139/v67-163.
Berge et al., Pharmaceutical salts. J Pharm Sci. Jan. 1977;66(1):1-19.
Busscher et al., Carbohydrate mimic of 2-deoxystreptamine for the preparation of conformationally constrained aminoglycosides. Tetrahedron, 2007;63(15):3183-3188.
Davidson et al., Stereoselective Synthesis of d-Desosamine and Related Glycals via Tungsten-Catalyzed Alkynol Cycloisomerization. Org. Lett., 2004;6(10):1601-3. DOI: 10.1021/o1049630m.
Giguere et al., Enantioselective de novo synthesis of 4-deoxy-D-hexopyranoses via hetero-Diels-Alder cycloadditions: total synthesis of ezoaminuroic acid and neosidomycin. J Org Chem. Dec. 2, 2011;76(23):9687-98. doi: 10.1021/jo201673w. Epub Nov. 10, 2011.
He et al., Formation of unusual sugars: mechanistic studies and biosynthetic applications. Annu Rev Biochem. 2002;71:701-54. Epub Nov. 9, 2001.
Kinoshita et al., Simple synthesis of methyl $_{DL}$-desosaminide. J.C.S. Chem. Comm. 1979;493:766-767.
Korte et al., Zur synthese des d,L-picrocins. Tetrahedron 1962;18(6):657-66.
Lichtenthaler, New methods of preparative organic chemistry IV: Cyclization of dialdehydes with nitromethane. Angew. Chem. Internat. Edit. 1964;3(3)211-224.
Martins et al., Antimicrobial activity of chitosan derivatives containing N-quaternized moieties in its backbone: a review. Int J Mol Sci. Nov. 13, 2014;15(11):20800-32. doi: 10.3390/ijms151120800.
Mukaiyama et al., An efficient glycosylation of alcohol using 1-thioglucoside derivative. Chemistry Letters 1979; 487-490. Published by the Chemical Society of Japan.
Newman, Degradation and Synthesis of Desosamine. J. Org. Chem., 1964;29(6):1461-8. DOI: 10.1021/jo01029a046.
Richardson, The synthesis of desosamine hydrochloride. J. Chem. Soc., 1964;5364-70.
Roestamadji et al., Loss of individual electrostatic interactions between aminoglycoside antibiotics and resistance enzymes as an effective means to overcoming bacterial drug resistance. J. Am. Chem. Soc. 1995;117(45):11060-11069.
Shvekhgeimer et al., Aliphatic nitro alcohols. Synthesis, chemical transformations and applications. Russ Chem Rev, 1998;67(1):35-68.
Simak et al., A stereocontrolled synthesis of 3-acetamido-1,3,5-trideoxy- and 1,3,5,6-tetradeoxy-1,5-imino-D-glucitol. Carbohydr Res. 2009;344(8):966-971.
Sofia et al., Carbohydrate-Based Small-Molecule Scaffolds for the Construction of Universal Pharmacophore Mapping Libraries. J. Org. Chem. 1998;63(9):2802-2803.
Tsuzuki et al., Motilides, macrolides with gastrointestinal motor stimulating activity. I. O-substituted and tertiary N-substituted derivatives of 8,9-anhydroerythromycin A 6,9-hemiacetal. Chem Pharm Bull (Tokyo). 1989;37(10):2687-2700.
Velvadapu et al., Concise syntheses of d-desosamine, 2-thiopyrimidinyl desosamine donors, and methyl desosaminide analogues from d-glucose. Carbohydrate Research Jan. 2008;343(1):145-150.
Woodward et al., Asymmetric total synthesis of erythromycin: Total synthesis of erythromycin. J. Am. Chem. Soc. 1981;103:3215-3217.
Zhang et al., Synthesis of D-Desosamine and Analogs by Rapid Assembly of 3-Amino Sugars. Angew Chem Int Ed Engl. 2016;55(2):523-527.

\* cited by examiner

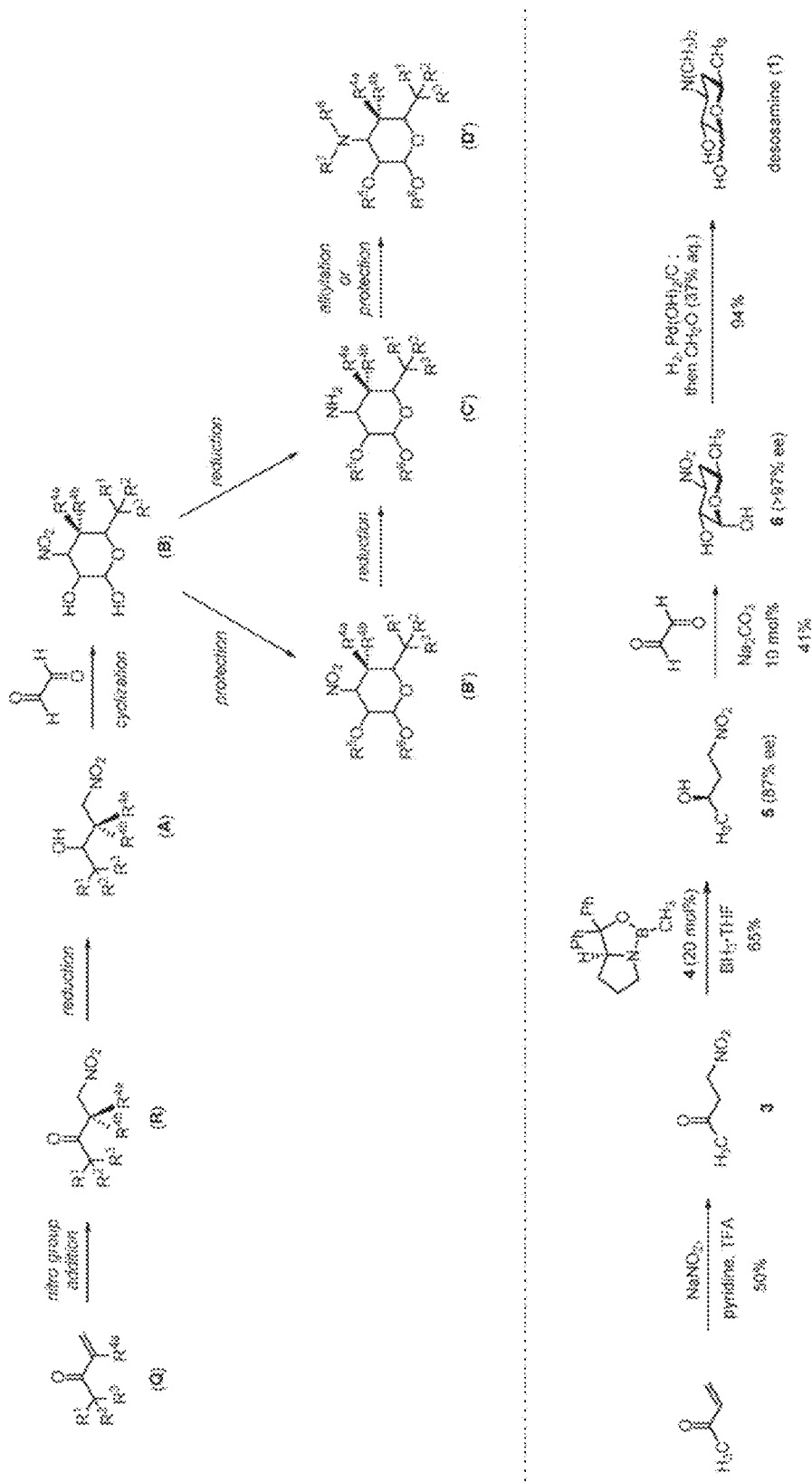

SYNTHESIS OF DESOSAMINES

RELATED APPLICATIONS

The present application is a continuation of and claims priority under 35 U.S.C. § 120 to U.S. patent application U.S. Ser. No. 15/558,910, filed Sep. 15, 2017, which is a national stage filing under 35 U.S.C. § 371 of international application, PCT/US2016/024210, filed Mar. 25, 2016, which claims priority under 35 U.S.C. § 119(e) to U.S. provisional patent application, U.S. Ser. No. 62/138,168, filed Mar. 25, 2015, each of which is incorporated herein by reference.

GOVERNMENT SUPPORT

This invention was made with government support under AI058395 awarded by the National Institutes of Health. The government has certain rights in the invention.

BACKGROUND

Emerging resistance to existing antibiotics is rapidly developing as a crisis of global proportions, especially for *Staphylococcus aureus, Streptococcus pyogenes*, and *Streptococcus pneumonia* infections. Pathogenic bacteria can transmit genes coding for antibiotic resistance both vertically (to their progeny) and horizontally (to neighboring bacteria of different lineages), and as a result antibiotic resistance can evolve quickly, particularly in nosocomial (hospital) settings. See, e.g., Wright, *Chem. Commun.* (2011) 47:4055-4061. This year, >99,000 people will die in the U.S. from healthcare-associated infections, more than all casualties from car accidents, HIV, and breast cancer combined, creating an estimated burden of up to $45 billion in U.S. healthcare costs. See, e.g., Klevens et al., *Public Health Rep.* (2007) 122:160-166. The current crisis is exacerbated by the fact that most major pharmaceutical companies have essentially abandoned research in the development of new antibiotics. See, e.g., Projan, *Curr. Opin. Microbiol.* (2003) 6:427-430. The current rate of introduction of new antibiotics does not adequately address growing resistance, and with the ease of international travel and increasing population densities, the need for innovation in the field has never been higher.

The sugars desosamine and mycaminose are critical components of many macrolide antibiotics. For the development of practical and scalable synthetic routes to macrolide antibiotics and novel analogs, there is a need for simple and efficient methods of preparing desosamine, mycaminose, and analogs thereof.

SUMMARY OF THE INVENTION

The present invention describes methods of preparing desosamine and mycaminose, and analogs thereof; intermediates in their preparation; and novel desosamine and mycaminose analogs. D-desosamine and D-mycaminose are monosaccharides with the following structures:

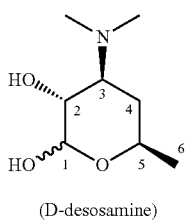
(D-desosamine)

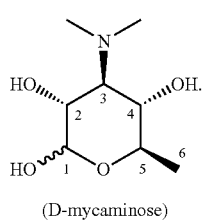
(D-mycaminose)

D-desosamine is a component of erythromycin, and many other macrolide antibiotics (e.g., tylosin, azithromycin, solithromycin, cethromycin) feature a desosamine or mycaminose sugar attached to the macrolide at the C5 position. X-ray crystallographic studies reveal that both sugars make extensive contacts with the 23S subunit of bacterial ribosomal RNA, and thus it is thought that they play key roles in antibiotic activity. See, e.g., Tu et al., *Cell* (2005) 121:257-270; Mankin et al., *Current Opinion in Microbiology* (2008) 11:414-421. Variation of the C5 sugar with desosamine or mycaminose derivatives may afford macrolide antibiotics with desired pharmaceutical properties (e.g., efficacy versus resistant strains, improved pharmacokinetics, reduced side-effects).

Since the structure of desosamine was determined in 1962, a number of syntheses of the compound have been reported. See, e.g., Korte et al., *Tetrahedron Lett.* (1962) 18:657-666; Newman, *J. Org. Chem.* (1964) 29:1461-1468; Richardson, *J. Chem. Soc.* (1964) 5364-5370; Baer et al., *Can. J. Chem.* (1974) 52:122-124; Davidson et al., *Org. Lett.* (2004) 6:1601-1603; Velvadapu et al., *Carbohydr. Res.* (2008) 343:145-150. Richardson, Davidson et al., and Velvadapu et al., in particular, have reported stereospecific approaches to the naturally occurring enantiomer, D-desosamine. Richardson's synthesis from 3-acetoamido-4,6-O-benzylidene-3-deoxy-D-α-glucopyranoside proceeded in 8 steps and 1.6% yield. Davidson et al. reported an 11-step synthesis of D-desosamine-1,2-diacetate that featured a tungsten-catalyzed alkynol cycloisomerization. This route employed (R)-3-tert-butyldimethylsiloxybutanal as starting material and proceeded in 13% overall yield. Velvadapu et al. published a 5-step route to D-desosamine employing methyl D-α-glucopyranoside as the starting material and proceeded in 16% overall yield. Desosamine can also be obtained from erythromycin by acidic hydrolysis, but the process is laborious and low-yielding.

We provide a practical and efficient method of preparing a desosamine, mycaminose, or analog thereof. Starting with a nitro alcohol of Formula (A):

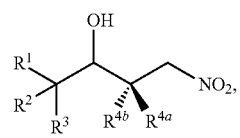

the synthesis of a desosamine or mycaminose analog can be accomplished in a few steps. First, the nitro alcohol of Formula (A) is cyclized with glyoxal:

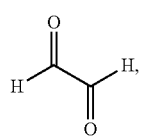

to yield a nitro sugar of Formula (B):

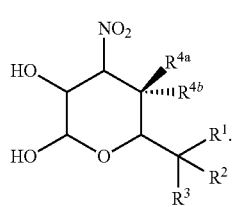
(B)

Following optional protection to yield a nitro sugar of Formula (B'):

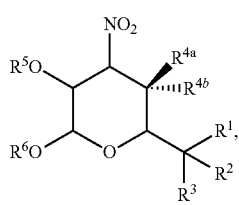
(B')

the nitro sugar is reduced to transform the nitro group into an amine. The resulting amino sugar of Formula (C'):

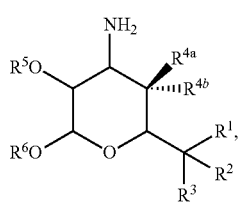
(C')

is then alkylated or protected to give a desosamine or mycaminose of Formula (D'):

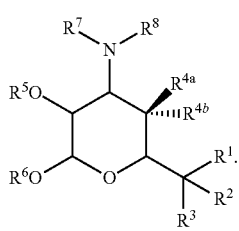
(D')

Definitions for the substituents $R^1$, $R^2$, $R^3$, $R^{4a}$, $R^{4b}$, $R^5$, $R^6$, $R^7$, and $R^8$ are provided in the Detailed Description.

The nitro alcohol of Formula (A) may be prepared by any method. An example is the following two step procedure from a vinyl ketone. Addition of a nitro group to the vinyl ketone of Formula (Q):

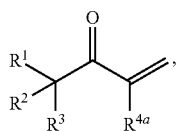
(Q)

affords a nitro ketone of Formula (R):

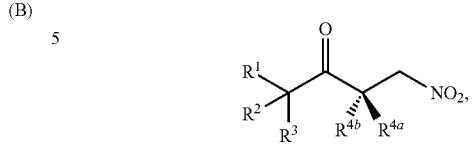
(R)

which is then reduced to yield the nitro alcohol of Formula (A).

The desosamine and mycaminose analogs may be modified to prepare glycosyl donors (e.g., to be used in the glycosylation step of a macrolide synthesis). A method provided herein for preparing a thioglycoside desosamine or mycaminose derivative comprises the steps of optionally protecting a compound of Formula (D') to yield a compound of Formula (E'):

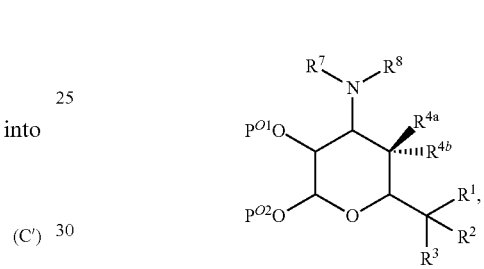
(E')

and contacting a compound of Formula (E') with 2-mercaptopyrimidine to form a thioglycoside of Formula (F'):

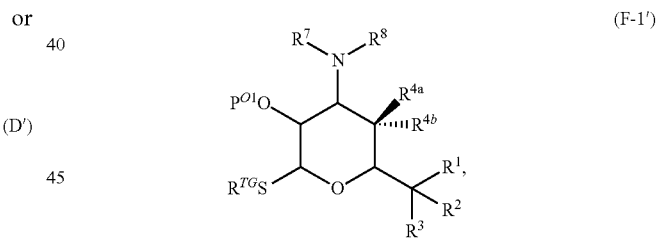
(F-1')

wherein $R^1$, $R^2$, $R^3$, $R^{4a}$, $R^{4b}$, $P^{O1}$, $P^{O2}$, $R^{TG}$, $R^7$, and $R^8$ are as defined herein.

The present disclosure provides novel desosamine and mycaminose analogs, as a compound of Formula (J):

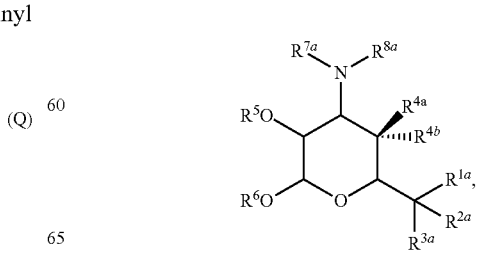
(J)

or salt thereof. In addition, the intermediate nitro sugar is provided as a compound of Formula (K):

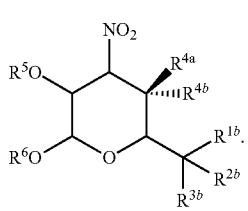

(K)

or a salt thereof. See the Detailed Description for definitions of $R^{1b}$, $R^{2b}$, $R^{3b}$, $R^{4a}$, $R^{4b}$, $R^5$, $R^6$, $R^7$ and $R^8$.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWING

The accompanying drawing, which constitute a part of this specification, illustrate several embodiments of the invention and together with the description, serve to explain the principles of the invention.

FIG. 1. Synthetic scheme of desosamine and mycaminose analogs, and synthesis of D-desosamine.

DETAILED DESCRIPTION OF CERTAIN EMBODIMENTS

Desosamine (3-(dimethylamino)-3,4,6-trideoxyhexose) is a monosaccharide with a structure of the formula:

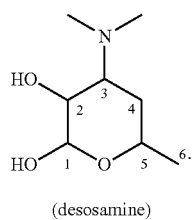

(desosamine)

The carbons are numbered from 1 to 6 following the convention for hexose sugars and are referred to herein as C1, C2, C3, C4, C5, and C6. There are several possible stereoisomers of desosamine, and analogs thereof. The stereoisomer found in many macrolides containing desosamine is D-desosamine of the structure:

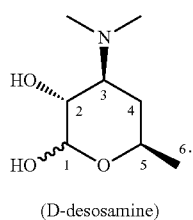

(D-desosamine)

Those skilled in the art will recognize that the stereochemistry at the hemiacetal carbon (C1) of D-desosamine may be of either the (R) or (S) configuration, and those configurations may interconvert through the process of anomerization. Typically the two anomers are in equilibrium when the sugar is in solution. The cyclic hemiacetal forms are also in equilibrium with a linear form, which is an intermediate of the anomerization process, and for D-desosamine is of formula:

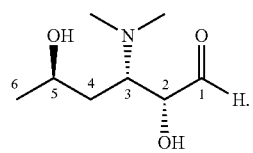

As used herein, the term "desosamine," when not only referring to 3-(dimethylamino)-3,4,6-trideoxyhexose, encompasses desosamine, desosamine analogs, desosamine derivatives, and protected desosamines. Mycaminose is a monosaccharide of similar structure to desosamine with a hydroxyl group at the C4 position, as in the following structures:

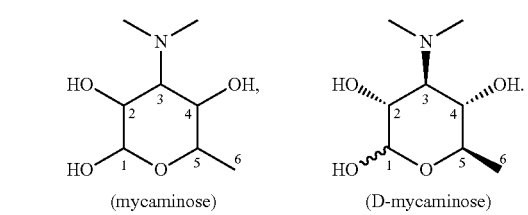

(mycaminose)      (D-mycaminose)

The term "mycaminose," when not only referring to 3-(dimethylamino)-3,6-dideoxyhexose, encompasses mycaminose, mycaminose analogs, mycaminose derivatives, and protected mycaminoses. The C4 position of a desosamine is substituted with two hydrogen atoms, while the C4 position of a mycaminose has at least one non-hydrogen substituent (e.g., hydroxyl, alkoxy).

In the case of desosamine itself methods herein provide a four-step route to the sugar. The process described herein provides a synthesis of highly enantiomerically enriched D-desosamine from methyl vinyl ketone (See FIG. 1). The method is suitable for large-scale synthesis and requires no chromatography. In other aspects, the method provides a synthetic route to analogs of desosamine and enantiomerically enriched desosamine derivatives. The invention also contemplates analogs of both desosamine and mycaminose and related sugars. The synthesis of desosamine, mycaminose, and analogs thereof may, in some embodiments, be accomplished in four steps (e.g., from a vinyl ketone), or depending on the compound, intermediates, and starting materials necessary may require fewer or more steps. Desosamines include compounds with substitution at any or all positions of desosamine. The methods herein may afford desosamines as either neutral compounds or salts.

The invention is, in part, directed to methods of synthesizing desosamine and mycaminose analogs. As generally described herein, the desosamine or mycaminose is prepared according to Scheme 1. First, a compound of Formula (A) is cyclized with glyoxal ($C_2H_2O_2$) to yield a compound of Formula (B). Second, the compound of Formula (B), a nitro sugar, is reduced to yield a compound of Formula (C'), an amino sugar. Third, the compound of Formula (C') is alkylated or protected to yield a compound of Formula (D'). The second and third steps may be performed in a single procedure, i.e., without isolation of the amino sugar. The synthesis may be carried out without protection of the C1 and C2 hydroxy positions, in which case $R^5$ and $R^6$ are hydrogen for compounds of both Formula (C') and (D'). Alternatively, the hydroxy positions may be protected prior to the step of reducing to transform a compound of Formula (B) into a compound of Formula (B'). The compound of Formula (B') would then be reduced to yield a compound of Formula (C') and subsequently alkylated or protected to yield a compound of Formula (D').

The schemes provided are not limiting, and the disclosure contemplates methods wherein additional steps are added, existing steps are omitted or substituted, or the order of steps is altered. For example, for certain functional groups, additional protection or deprotection steps may be necessary or desired to maintain compatibility with certain reactions or reagents. The synthetic steps, formulae of starting material, intermediates, and products, and substituents therein are further defined below.

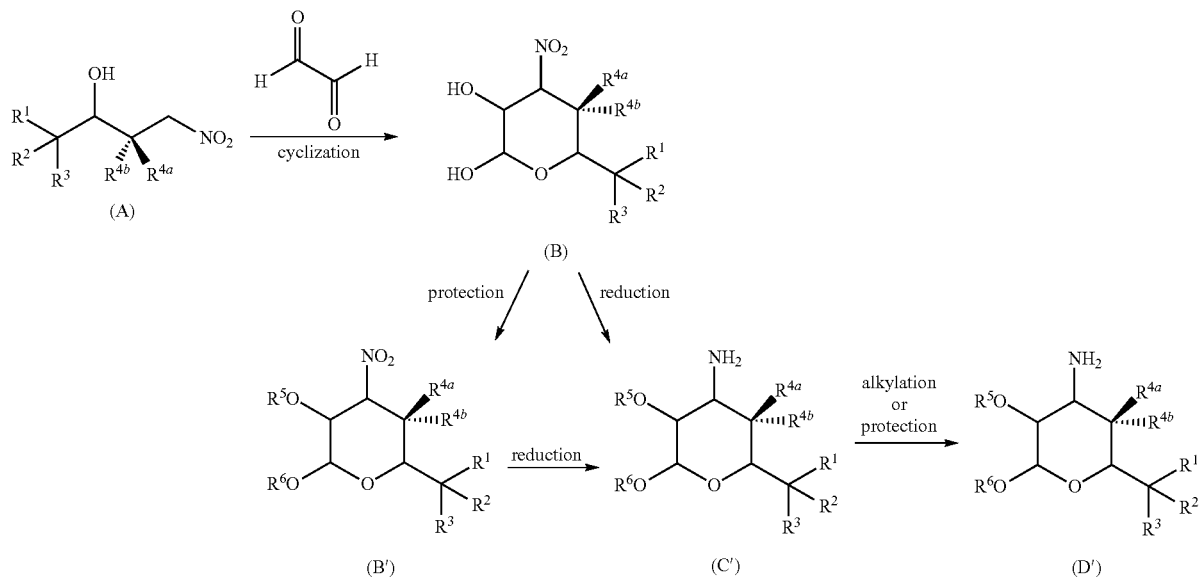

The compound of Formula (A) may be prepared according to Scheme 2. A nitro group is added to a vinyl ketone of Formula (Q), to yield a β-nitro ketone of Formula (R). The compound of Formula (R) is then reduced to yield the compound of Formula (A).

Methods of Preparing a Desosamine, Mycaminose, or Analog Thereof

In certain embodiments, the invention provides methods for the preparation of a compound of Formula (D'):

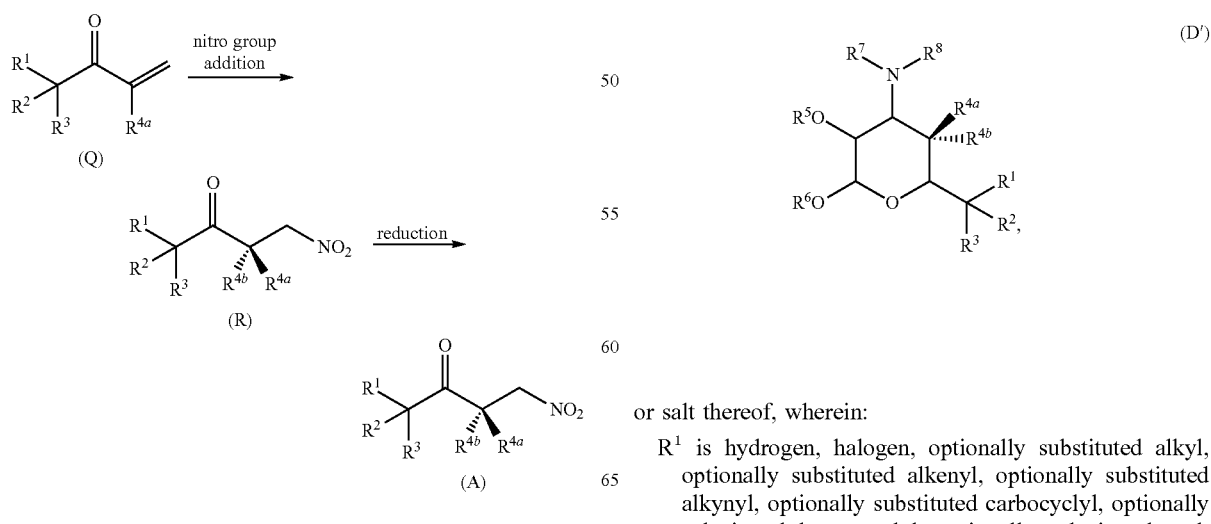

or salt thereof, wherein:
$R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^S$, —N(R$^S$)$_2$, —NR$^S$(OR$^S$), —SR$^S$, —SSR$^S$, —Si(R$^S$)$_3$, —OSi(R$^S$)$_3$, or of formula:

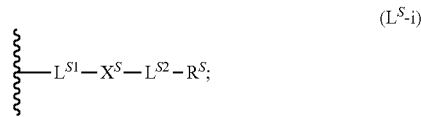

(L$^S$-i)

each of R$^2$ and R$^3$ is independently hydrogen, halogen, optionally substituted C$_1$-C$_6$ alkyl, —OR$^{SO}$, or —N(R$^{SN}$)$_2$.

L$^{S1}$ is a bond, —NR$^S$—, —O—, or —S—, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;

X$^S$ is a bond, —C(=O)—, —C(=NR$^{SN}$)—, —S(=O)—, or —S(=O)$_2$—;

L$^{S2}$ is a bond, —NR$^S$—, —O—, or —S—, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;

each R$^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two R$^S$ attached to the same nitrogen atom are taken together to form =N$_2$ or an optionally substituted heterocyclyl or heteroaryl ring;

each of R$^7$ and R$^8$ is independently hydrogen, optionally substituted C$_1$-C$_6$ alkyl, optionally substituted carbocyclyl, optionally substituted aryl, optionally substituted heterocyclyl, optionally substituted heteroaryl, optionally substituted acyl, or a nitrogen protecting group, or R$^7$ and R$^8$ are joined to form an optionally substituted heterocyclyl or heteroaryl ring;

each R$^{SN}$ is independently hydrogen, optionally substituted C$_1$-C$_6$ alkyl, or a nitrogen protecting group, or two R$^{SN}$ attached to the same nitrogen atom are joined to form an optionally substituted heterocyclyl or heteroaryl ring;

each of R$^{4a}$ and R$^{4b}$ is independently hydrogen, halogen, optionally substituted C$_1$-C$_6$ alkyl, or —OR$^{SO}$; and each of R$^5$, R$^6$ and R$^{SO}$ is independently hydrogen, optionally substituted C$_1$-C$_6$ alkyl, a carbohydrate, or an oxygen protecting group.

Unless otherwise stated, any formulae described herein are also meant to include salts, solvates, hydrates, polymorphs, co-crystals, tautomers, stereoisomers, and isotopically labeled derivatives thereof. In certain embodiments, the provided compound is a salt of any of the formulae described herein. In certain embodiments, the provided compound is a pharmaceutically acceptable salt of any of the formulae described herein. In certain embodiments, the provided compound is a solvate of any of the formulae described herein. In certain embodiments, the provided compound is a hydrate of any of the formulae described herein. In certain embodiments, the provided compound is a polymorph of any of the formulae described herein. In certain embodiments, the provided compound is a co-crystal of any of the formulae described herein. In certain embodiments, the provided compound is a tautomer of any of the formulae described herein. In certain embodiments, the provided compound is a stereoisomer of any of the formulae described herein. In certain embodiments, the provided compound is of an isotopically labeled form of any of the formulae described herein. For example, compounds having the present structures except for the replacement of hydrogen by deuterium or tritium, replacement of $^{19}$F with $^{18}$F, or the replacement of a $^{12}$C by a $^{13}$C or $^{14}$C are within the scope of the disclosure. In certain embodiments, the provided compound is a deuterated form of any of the formulae described herein.

A compound of Formula (D') may be provided by alkylating or protecting the amine at the C3 position. In certain embodiments, the invention provides methods of preparing a compound of Formula (D'):

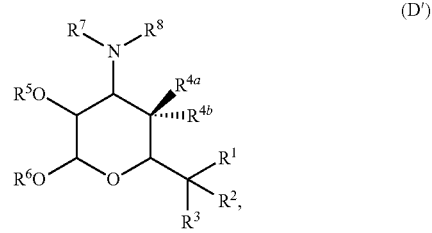

(D')

or salt thereof, comprises alkylating or protecting a compound of Formula (C'):

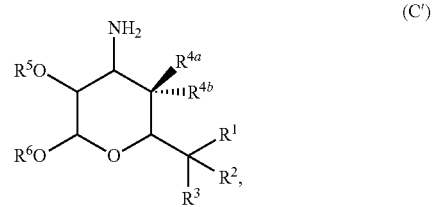

(C')

or salt thereof, with an alkylating or protecting agent, wherein R$^1$, R$^2$, R$^3$, R$^{4a}$, R$^{4b}$, R$^5$, R$^6$, R$^7$, and R$^8$ are as defined herein.

In certain embodiments, for the step of alkylating or protecting a compound of Formula (C'), the compound of Formula (C') is a salt of Formula (C—X'):

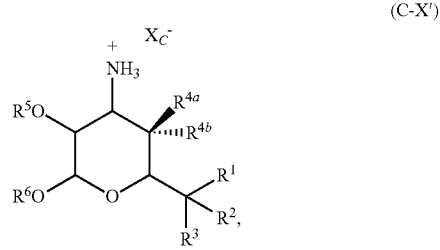

(C-X')

and the step of alkylating or protecting is performed in the presence of a base, and $X_c^-$ is an anion. In certain embodiments, $X_c^-$ is selected the group consisting of halide, $H_3CC(=O)O^-$, $NO_3^-$, $ClO_4^-$, $OH^-$, $H_2PO_4^-$, $HCO_3^-$ $HSO_4^-$, sulfonates, carboxylates, carboranes, $BF_4^-$, $PF_4^-$, $PF_6^-$, $AsF_6^-$, $SbF_6^-$, $B[3,5\text{-}(CF_3)_2C_6H_3]_4^-$, $BPh_4^-$, and $Al(OC(CF_3)_3)_4^-$. In some embodiments, $X_c^-$ is fluoride. In some embodiments, $X_c^-$ is chloride, bromide, or iodide. In some embodiments, $X_c^-$ is acetate.

The alkylation step may comprise dimethylation of the amine to give a dimethylamino group. When this demethylation is carried out with aqueous formaldehyde, the reaction is known as the Eschweiler-Clarke reaction. In some embodiments, the alkylating agent is formaldehyde. In some embodiments, the step of alkylating with formaldehyde is performed in the presence of formic acid. In some embodiments, the step of alkylating with formaldehyde is performed in the presence of sodium cyanoborohydride. In some embodiments, the alkylating agent is benzyl bromide. In some embodiments, the protecting agent is di-tert-butyl dicarbonate ($Boc_2O$). In some embodiments, the step of alkylating or protecting is performed in the presence of a base (e.g., a carbonate, a bicarbonate). In some embodiments, the alkylating agent is an organomagnesium, organolithium, organocopper, organozinc, organosodium, or organopotassium reagent. In some embodiments, the alkylating reagent is an alkyl halide. In some embodiments, the alkylating agent is bromomethane, diazoamethane, 2,2-dimethoxypropane, dimethyl carbonate, dimethyl dicarbonate, dimethyl sulfate, 1,2-dimethylhydrazine, dimethylzinc, methyl fluorosulfonate, methyl iodide, methyl methansulfonate, methyl trifluoromethanesulfonate, methylcobalamin, or trimetyloxonium tetrafluoroborate. In some embodiments, the step of alkylating or protecting is performed in the presence of a protecting agent and a base (e.g., a carbonate, a bicarbonate).

The protecting agent may be any reagent suitable for modifying an amine with a nitrogen protecting group, as defined herein. In some embodiments, the protecting agent is benzyl chloroformate, fluorenylmethyloxycarbonyl chloride, acetic anhydride, acetyl chloride, benzoyl chloride, p-toluenesulfonyl chloride, p-bromobenzenesulfonyl chloride, 2-nitrobenzenesulfonyl chloride, 4-nitrobenzenesulfonyl chloride, methanesulfonyl chloride, or trifluoromethanesulfonyl chloride. In some embodiments, the step of protecting is performed in the presence of a protecting agent and a base (e.g., a carbonate, a bicarbonate).

A compound of Formula (C') may be provided by reducing the nitro group of a compound of Formula (B') to yield an amino group. In certain embodiments, the method of preparing a compound of Formula (C'):

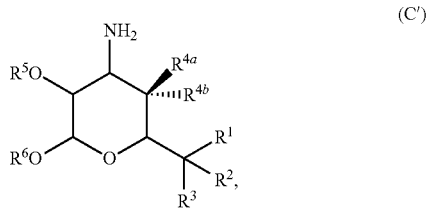

or salt thereof, comprises reducing a compound of Formula (B'):

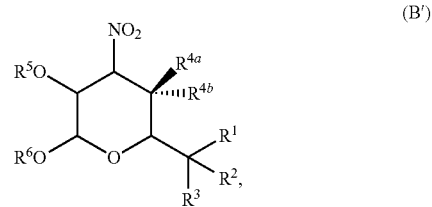

or salt thereof, wherein $R^1$, $R^2$, $R^3$, $R^{4a}$, $R^{4b}$, $R^5$, and $R^6$ are as defined herein. In certain embodiments, $R^5$ and $R^6$ are hydrogen. In certain other embodiments, the method further comprises protecting a compound of Formula (B):

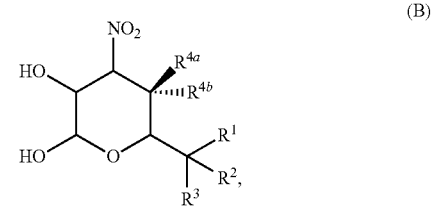

or salt thereof, to yield a compound of Formula (B'), or salt thereof. In some embodiments, the step of reducing is performed in the presence of $H_2$ and a catalyst. In some embodiments, the catalyst comprises palladium hydroxide. In some embodiments, the catalyst comprises palladium, platinum, rhodium, ruthenium, iridium, cobalt, iron, or nickel. In some embodiments, the catalyst is palladium on carbon or Raney nickel. In some embodiments, the step of reducing is performed in the presence of formic acid, a borane, an ammonium salt, or a silane.

A compound of Formula (B) may be provided by cyclizing a compound of Formula (A) with glyoxal. Glyoxal may be represented by the following structure:

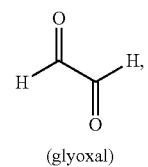

(glyoxal)

but may also exist in various hydrated and/or oligomeric forms. In certain embodiments, the method of preparing a compound of Formula (B):

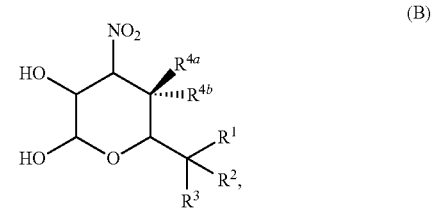

or salt thereof, comprises cyclizing an alcohol of Formula (A):

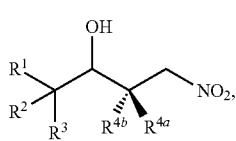

or salt thereof, with glyoxal:

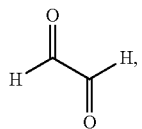

wherein $R^1$, $R^2$, $R^3$, $R^{4a}$, and $R^{4b}$ are as defined herein. In certain embodiments, the step of cyclizing is performed in the presence of a base. In certain embodiments, the step of cyclizing is performed in the presence of aqueous glyoxal. In certain embodiments, the step of cyclizing is performed in water. In certain embodiments, the step of cyclizing is performed in a biphasic mixture (e.g., water and an immiscible organic solvent). In some embodiments, the biphasic mixture comprises dichloromethane and water. In certain embodiments, the step of cyclizing is performed in water or a biphasic mixture in the presence of a base. In some embodiments, the base is a carbonate.

The step of cyclizing may be stereoselective, for instance when a particular stereoisomer of a compound of Formula (A) is provided. In certain embodiments, the compound of Formula (B), or salt thereof, is of Formula (B-1):

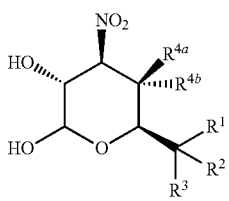

or salt thereof; and the alcohol of Formula (A) is of Formula (A-1):

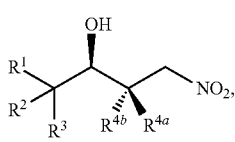

or salt thereof. In certain embodiments, the compound of Formula (B), or salt thereof, is of Formula (B-2):

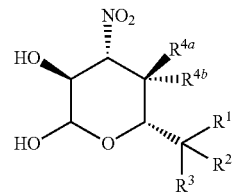

or salt thereof; and the alcohol of Formula (A) is of Formula (A-2):

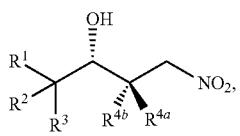

or salt thereof. In certain embodiments, the compound of Formula (B) is obtained in at least about 50% enantiomeric excess, at least about 75% enantiomeric excess, at least about 90% enantiomeric excess, at least about 95% enantiomeric excess, at least about 97% enantiomeric excess, or at least about 99% enantiomeric excess. In certain embodiments, the compound of Formula (A) is provided in at least about 50% enantiomeric excess, at least about 75% enantiomeric excess, at least about 90% enantiomeric excess, at least about 95% enantiomeric excess, at least about 97% enantiomeric excess, or at least about 99% enantiomeric excess.

A compound of Formula (A) may be provided by reducing a β-nitro ketone of Formula (R). In certain embodiments, the method of preparing a compound of Formula (A) comprises reducing a compound of Formula (R):

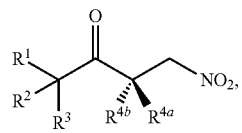

or salt thereof, to yield a compound of Formula (A), or salt thereof. In certain embodiments, the step of reduction is stereoselective. In some embodiments, the compound of Formula (A) is a compound of Formula (A-1):

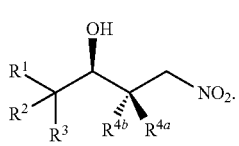

In some embodiments, the compound of Formula (A) is a compound of Formula (A-2):

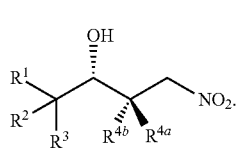

(A-2)

In some embodiments, the compound of Formula (A) is obtained in at least about 50% enantiomeric excess, at least about 75% enantiomeric excess, at least about 90% enantiomeric excess, at least about 95% enantiomeric excess, at least about 97% enantiomeric excess, or at least about 99% enantiomeric excess. In certain embodiments, the step of reducing is performed in the presence of a borane and a chiral catalyst. In some embodiments, the borane is $BH_3$ or $BH_3$-THF complex. In some embodiments, the chiral catalyst is an oxazaborilidine. In some embodiments, the catalyst is a Corey-Bakshi-Shibata catalyst. See, e.g., Corey et al., *J. Am. Chem. Soc.* (1987) 109:5551-5553; *Angew. Chem. Int. Ed.* (1998) 37:1986-2012. In some embodiments, the catalyst is of formula:

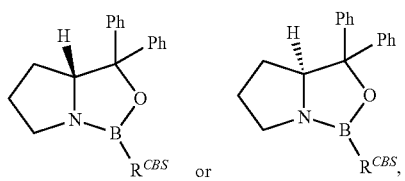

wherein $R^{CBS}$ is hydrogen, $C_1$-$C_6$ alkyl, or $C_1$-$C_6$ alkoxy.

A compound of Formula (R) may be provided by adding a nitro group to a vinyl ketone of Formula (Q). In certain embodiments, the method of preparing a compound of Formula (R) comprises adding a nitro group to a compound of Formula (Q):

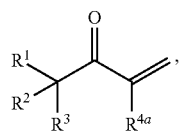

(Q)

or salt thereof, to yield a compound of Formula (R), or salt thereof. In certain embodiments, the step of adding a nitro group comprises contacting the compound of Formula (Q) with sodium nitrite. In certain embodiments, the step of adding a nitro group is performed in the presence an acid. In certain embodiments, the step of adding a nitro group is performed in the presence of an acid and pyridine. In some embodiments, the acid is acetic acid or trifluoroacetic acid. In some embodiments, the acid is pyridinium trifluoroacetic acid.

In an another aspect, the invention provides methods for preparing a glycosyl donor derivative of a desosamine, mycaminose, or analog thereof. A glycosyl donor is a carbohydrate that will react to form a glycosidic bond with a suitable acceptor. For example, the hydroxyl group of a macrolide (or macrolide precursor) may react with a glycosyl donor resulting in a glycosidic attachment of the desosamine or mycaminose to the macrolide (or precursor). Typical glycosyl donors have a leaving group attached to the anomeric carbon. Exemplary groups for the anomeric leaving group include halogens, thioethers, acetimidates, acetate, phosphates, and O-pentenyl. A thioglycoside is sugar with a thioether group at the anomeric carbon (C1). A method for preparing desosamine or mycaminose thioglycosides is described in Scheme 3. First, a compound of Formula (D') is optionally protected (e.g., when at least one of $R^5$ and $R^6$ is hydrogen) to give a compound of Formula (E'). The protected desosamine is then treated with a reagent suitable to replace the substituent at the anomer carbon with a leaving group, thus yielding a compound of Formula (F').

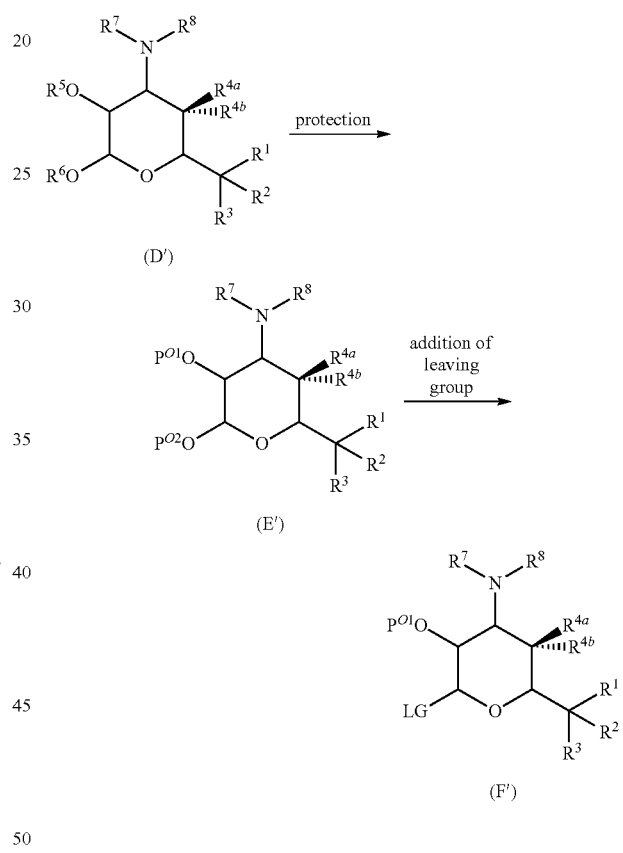

Scheme 3.

In certain embodiments, the method of preparing a compound of Formula (F') comprises the steps of optionally protecting a compound of Formula (D'), or salt thereof, to yield a compound of Formula (E'):

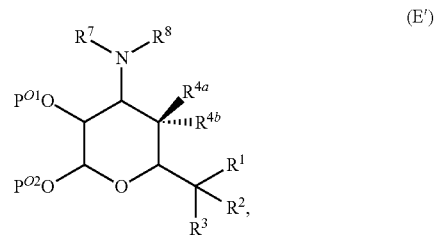

(E')

or salt thereof, and substituting the anomer carbon of a compound of Formula (E'), or salt thereof, with a leaving group to form a compound of Formula (F'):

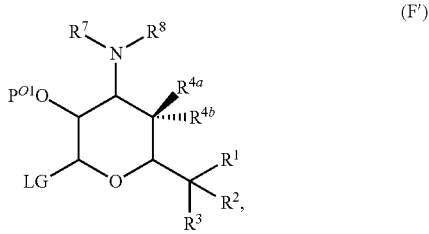

or salt thereof, wherein:
R$^1$, R$^2$, R$^3$, R$^{4a}$, R$^{4b}$, R$^5$, R$^6$, R$^7$, and R$^8$ are as defined herein;
each of P$^{O1}$ and P$^{O2}$ is independently optionally substituted C$_1$-C$_6$ alkyl, or an oxygen protecting group; and
LG is a leaving group.

Scheme 4.

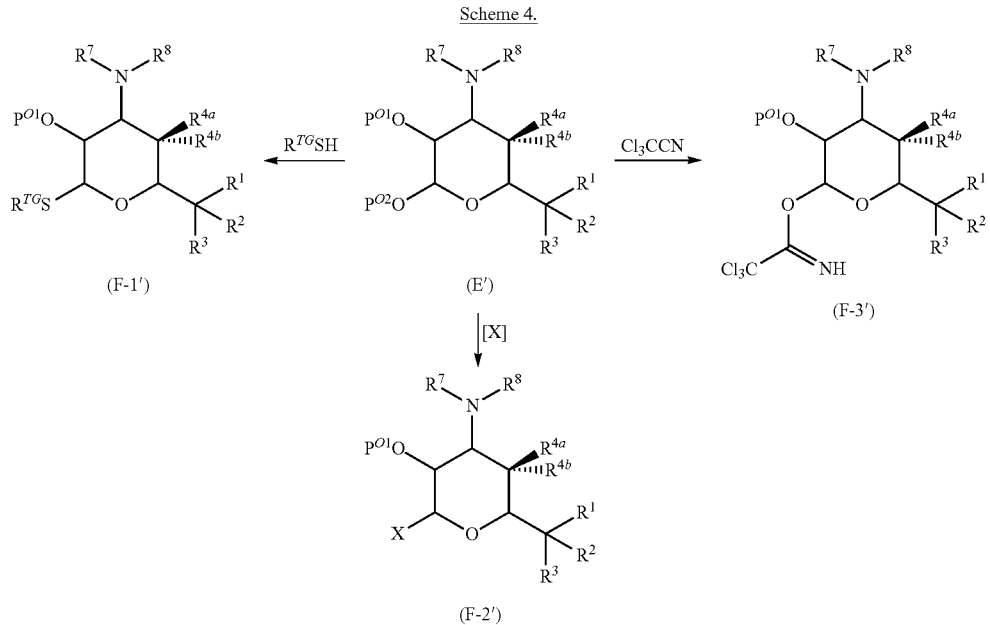

Exemplary methods of adding substituting the anomeric carbon with a leaving group are shown in Scheme 4. R$^{TG}$ is optionally substituted C$_1$-C$_6$ alkyl, optionally substituted phenyl, or optionally substituted heteroaryl. X is a halogen or triflate. [X] is a halogen or triflate donor (e.g., TMSCl, TMSBr, TMSI, TMSOTf, Bu$_4$NBr, Bu$_4$NI).

In certain embodiments, the leaving group is a halogen. In some embodiments, the leaving group is —F. In some embodiments, the leaving group is —Cl, —Br, or —I. In certain embodiments, the leaving group is an acetimidate (e.g., acetimidate, N-methylacetimidate, N-phenylacetimidate, trichloroacetimidate, N-methyltrichloroacetimidate, N-phenyltrichloroacetimidate, trifluoroacetimidate, N-methyltrifluoroacetimidate, N-phenyltrifluoroacetimidate). In certain embodiments, the leaving group is acetate. In certain embodiments, the leaving group is a phosphate. In certain embodiments, the leaving group is —O(CH$_2$)$_3$CH=CH$_2$.

In certain embodiments, the leaving group is —SR$^{TG}$. In some embodiments, R$^{TG}$ is optionally substituted C$_1$-C$_6$ alkyl. In some embodiments, R$^{TG}$ is C$_1$-C$_6$ alkyl. In some embodiments, R$^{TG}$ is optionally substituted aryl. In some embodiments, R$^{TG}$ is phenyl. In some embodiments, R$^{TG}$ is heteroaryl. In some embodiments, R$^{TG}$ is pyridinyl or pyramindyl. In some embodiments, —SR$^{TG}$ is:

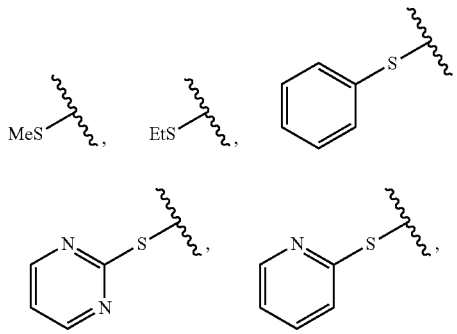

-continued

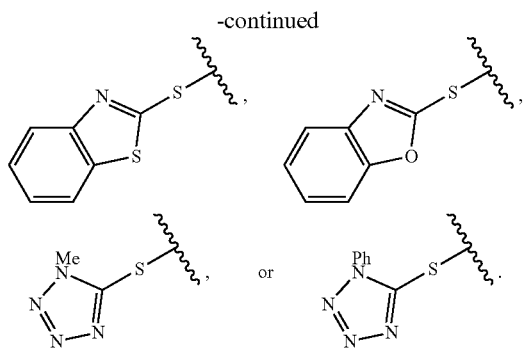

In certain embodiments, the step of substituting the anomeric carbon with —SR$^{TG}$ is performed in the presence of a boron trihalide (e.g., BF$_3$). In certain embodiments, the step of substituting the anomeric carbon with —SR$^{TG}$ is performed in the presence of a phosphine (e.g., triphenyl phosphine) and an azodicarboxylate (e.g., diethyl azodicarboxylate). In certain embodiments, the step of substituting the anomeric carbon with —SR$^{TG}$ is performed in the presence of a silyl compound and a base. In some embodiments, the silyl compound is a silyl halide (e.g., trimethylsilyl chloride) or a silyl triflate (e.g., trimethylsilyl triflate). In some embodiments, the base is a pyridine (e.g., pyridine, 2,4-lutidine, 2,6-lutidine). In some embodiments, the silyl compound is trimethylsilyl triflate, and the base is 2,6-lutidine.

In certain embodiments, the step of protecting is performed in the presence of methylchloroformate and a base (e.g., a carbonate, an amine). In some embodiments, the base is trimethylamine, trimethylamine, or diisopropylethylamine. The protecting groups P$^{O1}$ and P$^{O2}$ may each independently be any oxygen protecting group, as defined herein. In some embodiments, P$^{O1}$ is alkoxycarbonyl. In some embodiments, P$^{O2}$ is alkoxycarbonyl. In some embodiments, P$^{O1}$ and P$^{O2}$ are alkoxycarbonyl. In some embodiments, P$^{O1}$ is methoxycarbonyl. In some embodiments, P$^{O2}$ is methoxycarbonyl. In some embodiments, P$^{O1}$ and P$^{O2}$ are methoxycarbonyl. In some embodiments, each of P$^{O1}$ and P$^{O2}$ are independently acetyl, benzoyl, benzyl, methoxymethyl ether, p-methoxybenzyl ether, methylthiomethylether, pivaloyl, tetrahydropyranyl, tetrahydrofuranyl, triphenylmethyl, or silyl (e.g., trimethyl silyl, tert-butyldimethylsilyl, triisopropylsilyloxymethyl, triisopropylsilyl).

In certain embodiments, the method for preparing a compound of Formula (D') is for the preparation of a compound listed in Table 1. The method contemplates both the α and β anomer, though only one anomer is drawn for each compound in the table.

TABLE 1

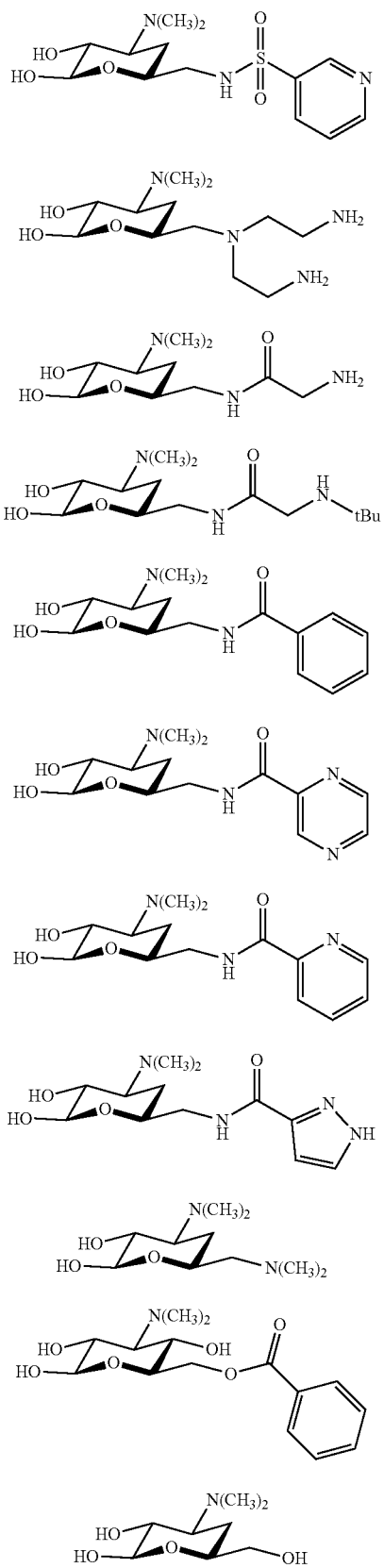

TABLE 1-continued

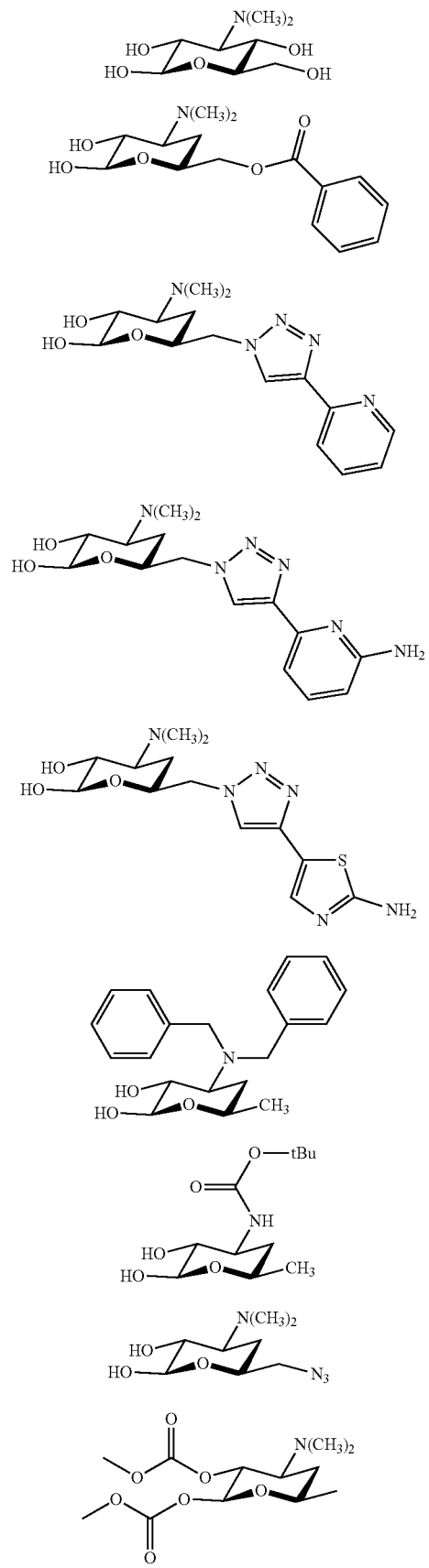

TABLE 1-continued

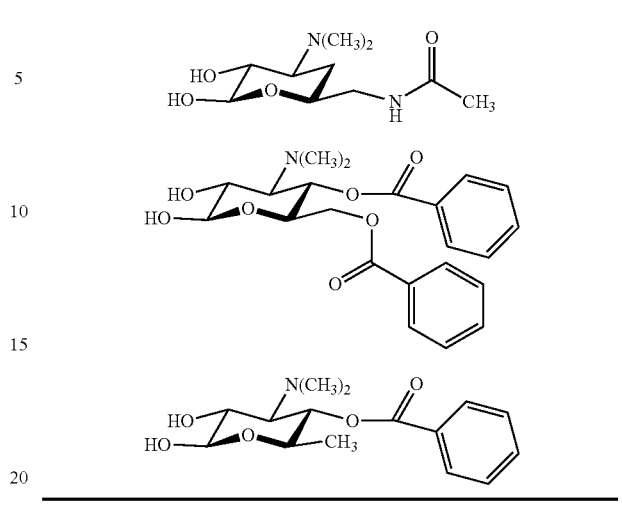

Compounds of Formula (J)

In another aspect, the invention provides novel desosamine or mycaminose analogs which have not been previously disclosed. In certain embodiments, the desosamine or mycaminose analog is a compound of Formula (J):

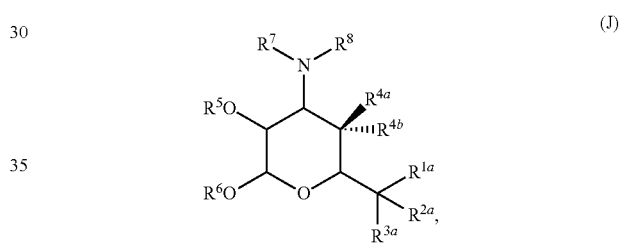

or salt thereof, wherein:

$R^{1a}$ is —$N(R^S)_2$, —$NR^S(OR^S)$, or of formula:

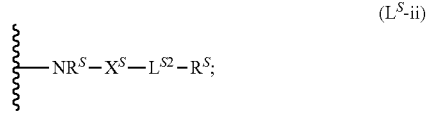

each of $R^{2a}$ and $R^{3a}$ is independently hydrogen, halogen, optionally substituted $C_1$-$C_6$ alkyl, or —$OR^{SO}$.

$X^S$ is a bond, —C(=O)—, —C(=$NR^{SN}$)—, —S(=O)—, or —S(=O)$_2$—;

$L^{S2}$ is a bond, —$NR^S$—, —O—, or —S—, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;

each $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two $R^S$ attached to the same nitrogen atom are taken together to form $=N_2$ or an optionally substituted heterocyclyl or heteroaryl ring;

each of $R^{7a}$ and $R^{8a}$ is independently optionally substituted $C_1$-$C_6$ alkyl, optionally substituted carbocyclyl, optionally substituted aryl, optionally substituted heterocyclyl, optionally substituted heteroaryl, optionally substituted acyl, or a nitrogen protecting group, or $R^{7a}$ and $R^{8a}$ are joined to form an optionally substituted heterocyclyl or heteroaryl ring;

each $R^{SN}$ is independently hydrogen, optionally substituted $C_1$-$C_6$ alkyl, or a nitrogen protecting group, or two $R^{SN}$ attached to the same nitrogen atom are joined to form an optionally substituted heterocyclyl or heteroaryl ring;

each of $R^{4a}$ and $R^{4b}$ is independently hydrogen, halogen, optionally substituted $C_1$-$C_6$ alkyl, or —$OR^{SO}$; and each of $R^5$, $R^6$ and $R^{SO}$ is independently hydrogen, optionally substituted $C_1$-$C_6$ alkyl, a carbohydrate, or an oxygen protecting group.

In certain embodiments, $R^{1a}$ is not:

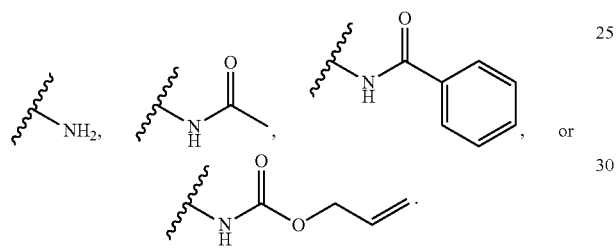

In certain embodiments, a compound of Formula (J) is a compound listed in Table 2. The invention contemplates both the α and β anomer, though only one anomer is drawn for each compound in the table.

TABLE 2

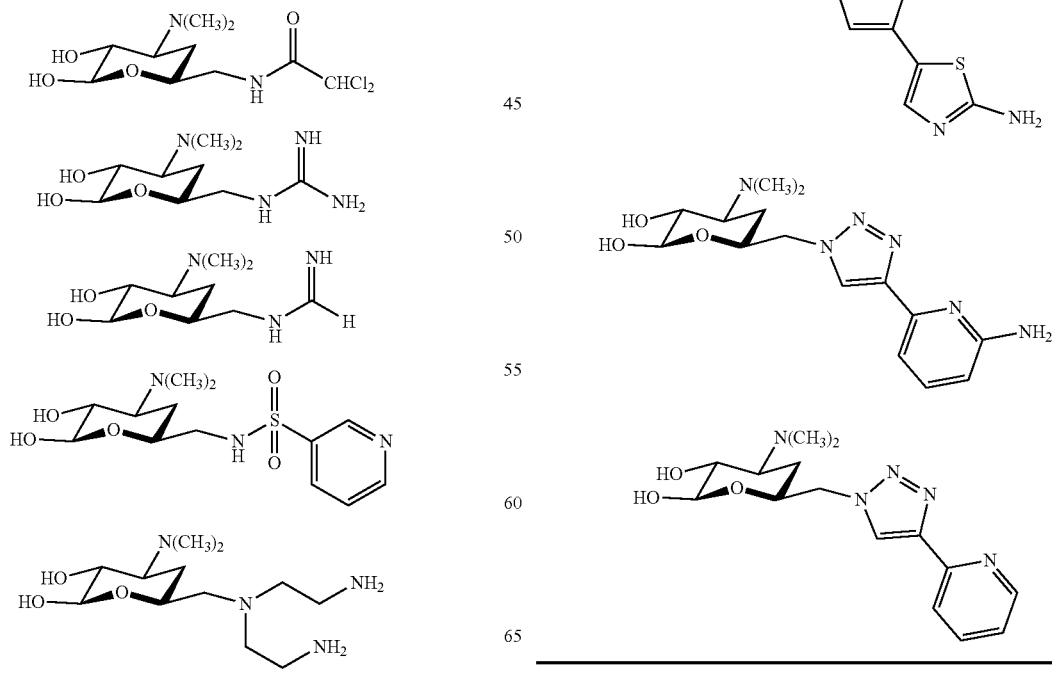

TABLE 2-continued

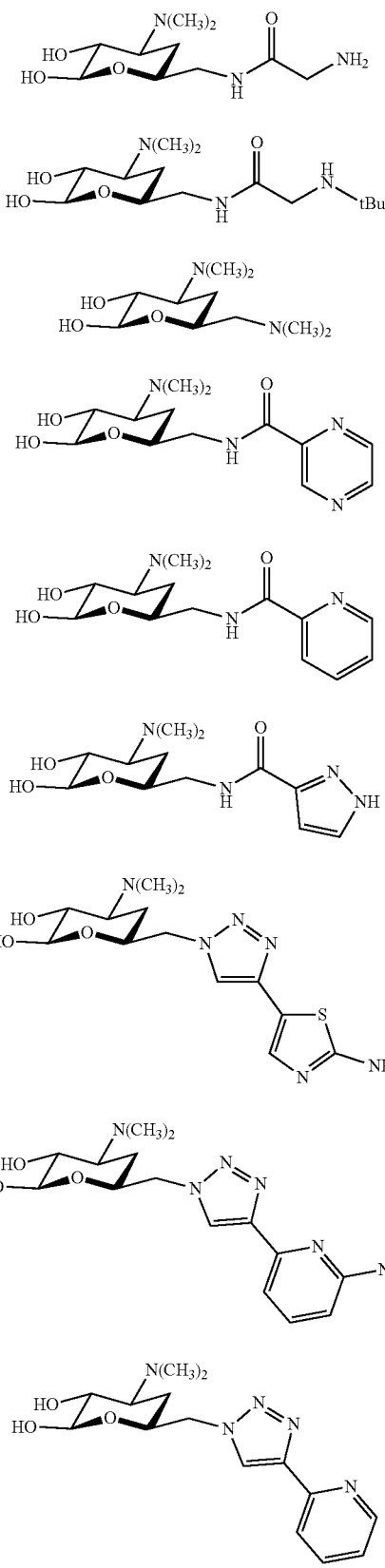

Compounds of Formula (K)

In another aspect, the invention provides a nitro sugar, which may be an intermediate in the preparation of a desosamine or mycaminose analog. In certain embodiments, the nitro sugar is a compound of Formula (K):

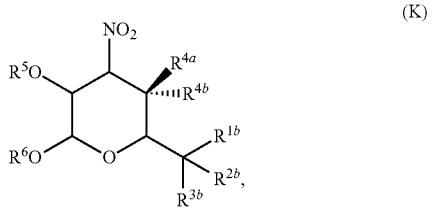

or salt thereof, wherein:

$R^{1b}$ is —N($R^S$)$_2$, —NR$^S$(OR$^S$), or of formula:

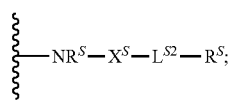

each of $R^{2b}$ and $R^{3b}$ is independently hydrogen, halogen, optionally substituted $C_1$-$C_6$ alkyl, or —OR$^{SO}$.

$X^S$ is a bond, —C(=O)—, —C(=NR$^{SN}$)—, —S(=O)—, or —S(=O)$_2$—;

$L^{S2}$ is a bond, —NR$^S$—, —O—, or —S—, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;

each $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two $R^S$ attached to the same nitrogen atom are taken together to form =N$_2$ or an optionally substituted heterocyclyl or heteroaryl ring;

$R^{SN}$ is hydrogen, optionally substituted alkyl, or a nitrogen protecting group; each of $R^{4a}$ and $R^{4b}$ is independently hydrogen, optionally substituted $C_1$-$C_6$ alkyl, or —OR$^{SO}$; and each of $R^5$, $R^6$ and $R^{SO}$ is independently hydrogen, halogen, optionally substituted $C_1$-$C_6$ alkyl, a carbohydrate, or an oxygen protecting group.

In certain embodiments, $R^{1b}$ is not:

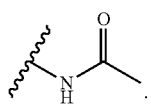

In certain embodiments, a compound of Formula (J) is a compound listed in Table 3. The invention contemplates both α and β anomer, though only one anomer is drawn for each compound in the table.

TABLE 3

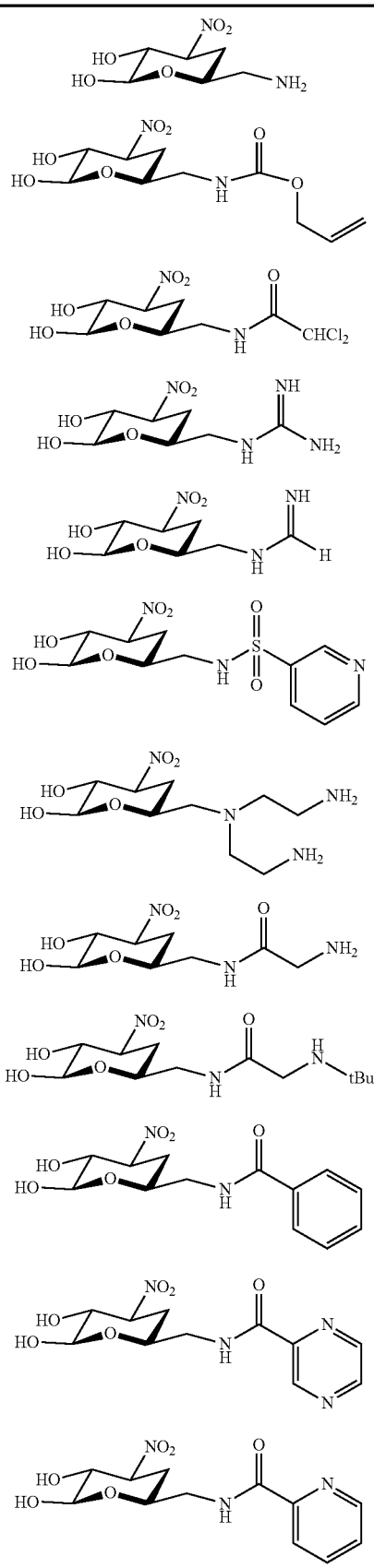

TABLE 3-continued

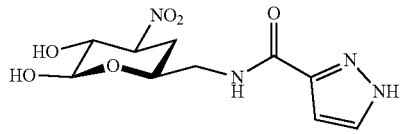

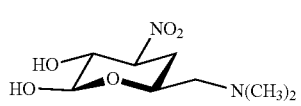

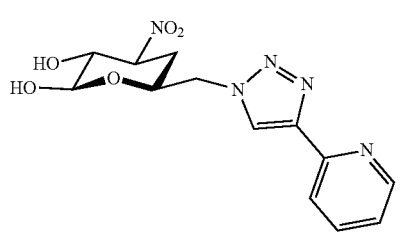

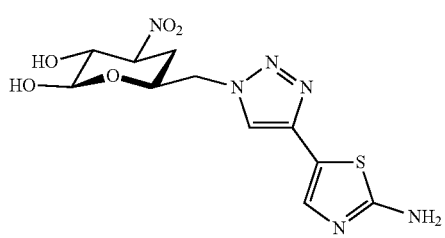

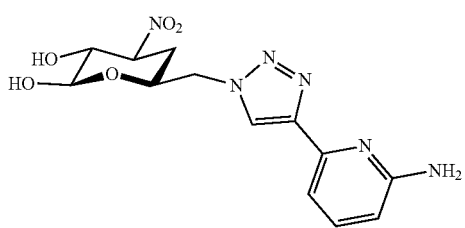

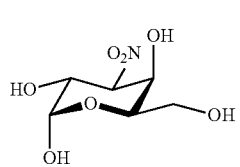

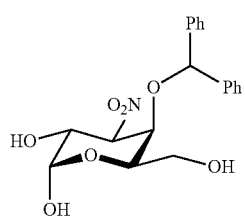

Additional Formulae

In certain embodiments, a compound of Formula (D') is of Formula (D-1'):

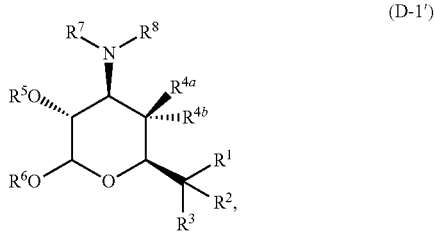

(D-1')

or salt thereof, wherein $R^1$, $R^2$, $R^3$, $R^{4a}$, $R^{4b}$, $R^5$, $R^6$, $R^7$, and $R^8$ are as defined herein.

In certain embodiments, a compound of Formula (D') is of Formula (D-2'):

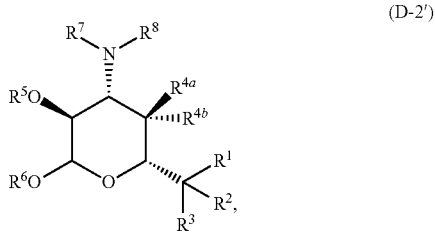

(D-2')

or salt thereof, wherein $R^1$, $R^2$, $R^3$, $R^{4a}$, $R^{4b}$, $R^5$, $R^6$, $R^7$, and $R^8$ are as defined herein.

In certain embodiments, a compound of Formula (D') is of Formula (D-d-1'):

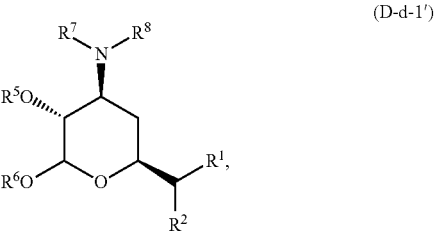

(D-d-1')

or salt thereof, wherein $R^1$, $R^2$, $R^5$, $R^6$, $R^7$, and $R^8$ are as defined herein.

In certain embodiments, a compound of Formula (D') is of Formula (D-d-1'):

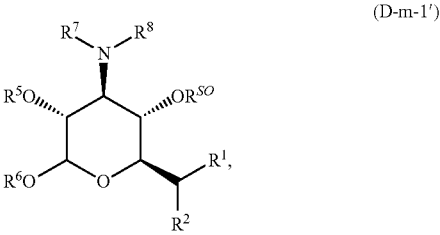

(D-m-1')

or salt thereof, wherein $R^1$, $R^2$, $R^{SO}$, $R^5$, $R^6$, $R^7$, and $R^8$ are as defined herein.

In certain embodiments, a compound of Formula (D') is of Formula (D-d-1'-A):

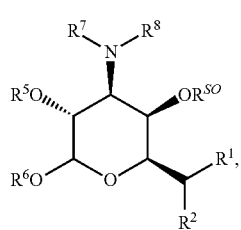
(D-m-1'-A)

or salt thereof, wherein $R^1$, $R^2$, $R^{SO}$, $R^5$, $R^6$, $R^7$, and $R^8$ are as defined herein.

In certain embodiments, a compound of Formula (J) is of Formula (J-1):

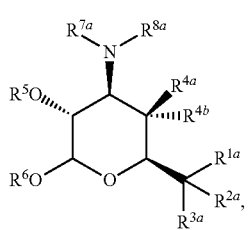
(J-1)

or salt thereof, wherein $R^{1a}$, $R^{2a}$, $R^{3a}$, $R^{4a}$, $R^{4b}$, $R^5$, $R^6$, $R^{7a}$, and $R^{8a}$ are as defined herein.

In certain embodiments, a compound of Formula (J) is of Formula (J-2):

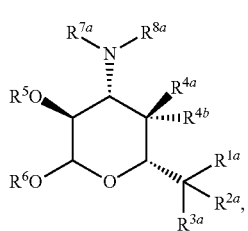
(J-2)

or salt thereof, wherein $R^{1a}$, $R^{2a}$, $R^{3a}$, $R^{4a}$, $R^{4b}$, $R^5$, $R^6$, $R^{7a}$, and $R^{8a}$ are as defined herein.

In certain embodiments, a compound of Formula (J) is of Formula (J-d-1):

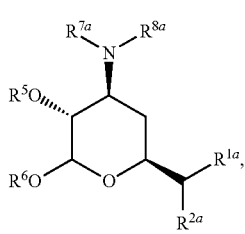
(J-d-1)

or salt thereof, wherein $R^{1a}$, $R^{2a}$, $R^5$, $R^6$, $R^{7a}$, and $R^{8a}$ are as defined herein.

In certain embodiments, a compound of Formula (J) is of Formula (J-m-1):

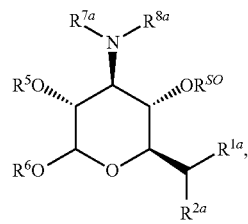
(J-m-1)

or salt thereof, wherein $R^{1a}$, $R^{2a}$, $R^{SO}$, $R^5$, $R^6$, $R^{7a}$, and $R^{8a}$ are as defined herein.

In certain embodiments, a compound of Formula (J) is of Formula (J-m-1-A):

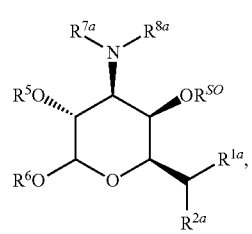
(J-m-1-A)

or salt thereof, wherein $R^{1a}$, $R^{2a}$, $R^S$, $R^5$, $R^6$, $R^{7a}$, and $R^{8a}$ are as defined herein.

In certain embodiments, a compound of Formula (K) is of Formula (K-1):

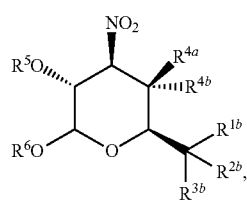
(K-1)

or salt thereof, wherein $R^{1b}$, $R^{2b}$, $R^{3b}$, $R^{4a}$, $R^{4b}$, $R^5$, and $R^6$ are as defined herein.

In certain embodiments, a compound of Formula (K) is of Formula (K-2):

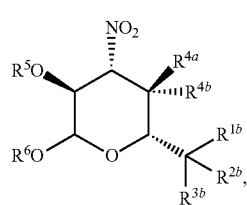
(K-2)

or salt thereof, wherein $R^{1b}$, $R^{2b}$, $R^{3b}$, $R^{4a}$, $R^{4b}$, $R^5$, and $R^6$ are as defined herein.

In certain embodiments, a compound of Formula (K) is of Formula (K-d-1):

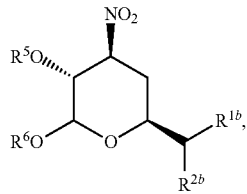

(K-d-1)

or salt thereof, wherein $R^{1b}$, $R^{2b}$, $R^5$, and $R^6$ are as defined herein.

In certain embodiments, a compound of Formula (K) is of Formula (K-m-1):

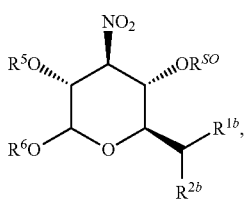

(K-m-1)

or salt thereof, wherein $R^{1b}$, $R^{2b}$, $R^{SO}$, $R^5$, and $R^6$ are as defined herein.

In certain embodiments, a compound of Formula (K) is of Formula (K-m-1-A):

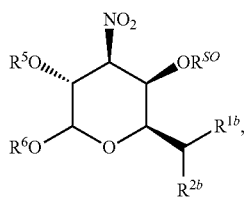

(K-m-1-A)

or salt thereof, wherein $R^{1b}$, $R^{2b}$, $R^{SO}$, $R^5$, and $R^6$ are as defined herein.

Group $R^1$

Compounds of Formula (A), (B), (B'), (C'), (D'), (Q), and (R) include $R^1$, which may be hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^S$, $-N(R^S)_2$, $-NR^S(OR^S)$, $-SR^S$, $-SSR^S$, $-Si(R^S)_3$, $-OSi(R^S)_3$, or of formula:

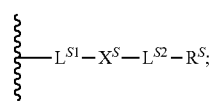

($L^S$-i)

wherein $R^S$, $L^{S1}$, $X^S$, $L^{S2}$ are as defined for compounds of Formula (D'). In certain embodiments, $R^1$ is hydrogen, halogen, optionally substituted alkyl, optionally substituted carbocyclyl, optionally substituted heterocyclyl, optionally substituted aryl, optionally substituted heteroaryl, $-OR^S$, $-N(R^S)_2$, or of Formula ($L^S$-i). In certain embodiments, $R^1$ is hydrogen, optionally substituted alkyl, $-OR^S$, $-N(R^S)_2$, or of Formula ($L^S$-i). In some embodiments, $R^1$ is hydrogen. In some embodiments, $R^1$ is $-F$. In some embodiments, $R^1$ is $-Cl$, $-Br$, or $-I$. In some embodiments, $R^1$ is optionally substituted alkyl. In some embodiments, $R^1$ is optionally substituted $C_1$-$C_6$ alkyl. In some embodiments, $R^1$ is $C_1$-$C_6$ alkyl. In some embodiments, $R^1$ is methyl. In some embodiments, $R^1$ is ethyl, propyl, or butyl. In some embodiments, $R^1$ is optionally substituted carbocyclyl. In some embodiments, $R^1$ is optionally substituted heterocyclyl. In some embodiments, $R^1$ is optionally substituted aryl. In some embodiments, $R^1$ is optionally substituted phenyl. In some embodiments, $R^1$ is optionally substituted heteroaryl. In some embodiments, $R^1$ is optionally substituted alkenyl. In some embodiments, $R^1$ is optionally substituted alkynyl. In some embodiments, $R^1$ is $-NR^S(OR^S)$. In some embodiments, $R^1$ is optionally substituted $-SR^S$. In some embodiments, $R^1$ is optionally substituted $-SSR^S$. In some embodiments, $R^1$ is optionally substituted $-Si(R^S)_3$. In some embodiments, $R^1$ is optionally substituted $-Si(OR^S)$.

$R^1$ may be is $-OR$. In some embodiments, $R^1$ is hydrogen. In some embodiments, $R^S$ is optionally substituted alkyl. In some embodiments, $R^S$ is optionally substituted $C_1$-$C_6$ alkyl. In some embodiments, $R^S$ is $C_1$-$C_6$ alkyl. In some embodiments, $R^S$ is methyl. In some embodiments, $R^S$ is ethyl. In some embodiments, $R^S$ is propyl. In some embodiments, $R^S$ is optionally substituted alkenyl. In some embodiments, $R^S$ is optionally substituted alkynyl. In some embodiments, $R^S$ is optionally substituted carbocyclyl. In some embodiments, $R^S$ is optionally substituted heterocyclyl. In some embodiments, $R^S$ is optionally substituted aryl. In some embodiments, $R^S$ is optionally substituted phenyl. In some embodiments, $R^S$ is optionally substituted heteroaryl. In certain embodiments, $R^S$ is an oxygen protecting group. In some embodiments, $R^S$ is alkoxycarbonyl. In some embodiments, $R^S$ is methoxycarbonyl. In some embodiments, $R^S$ is acetyl, benzoyl, benzyl, methoxymethyl ether, p-methoxybenzyl ether, methylthiomethylether, pivaloyl, tetrahydropyranyl, tetrahydrofuranyl, triphenylmethyl, or silyl (e.g., trimethyl silyl, tert-butyldimethylsilyl, triisopropylsilyloxymethyl, triisopropylsilyl). In certain embodiments, $R^S$ is a carbohydrate. In certain embodiments, $R^S$ is a monosaccharide.

In certain embodiments, $R^1$ is:

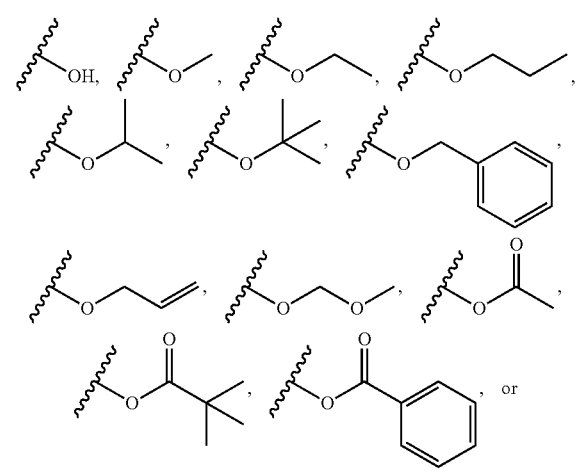

-continued

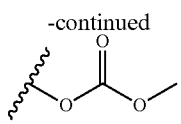

R[1] may be —N(R[S])[2]. The R[S] groups of —N(R[S])[2] may be the same or different. In certain embodiments, R[1] is NHR[S]. In certain embodiments, R[1] is —NMeR[S]. In some embodiments, R[1] is —NH[2]. In some embodiments, at least one R[1] is optionally substituted alkyl. In some embodiments, at least one R[S] is optionally substituted $C_1$-$C_6$ alkyl. In some embodiments, at least one R[S] is $C_1$-$C_6$ alkyl. In some embodiments, at least one R[S] is ethyl. In some embodiments, at least one R[S] is propyl. In some embodiments, R[S] is optionally substituted alkenyl. In some embodiments, R[S] is optionally substituted alkynyl. In some embodiments, at least one R[S] is optionally substituted carbocyclyl. In some embodiments, at least one R[S] is optionally substituted heterocyclyl. In some embodiments, at least one R[S] is optionally substituted aryl. In some embodiments, at least one R[S] is optionally substituted phenyl. In some embodiments, at least one R[S] is optionally substituted heteroaryl. In certain embodiments, at least one R[S] is a nitrogen protecting group. In some embodiments, at least one R[S] is benzyl. In some embodiments, at least one R[S] is alkoxycarbonyl. In some embodiments, at least one R[S] is methoxycarbonyl or tert-butoxycarbonyl. In some embodiments, at least one R[S] is carbobenzyloxy, fluorophenylmethyloxycarbonyl, acetyl, benzoyl, p-toluenesulfonyl, p-bromobenzenesulfonyl, 2-nitrobenzenesulfonyl, 4-nitrobenzenesulfonyl, methanesulfonyl, or trifluoromethanesulfonyl. In certain embodiments, two R[S] attached to the same nitrogen atom are taken together to form =N[2], i.e. —N(R[S])[2] is —N[3]. In certain embodiments, two R[S] attached to the same nitrogen atom are joined to form an optionally substituted heterocyclyl ring. In certain embodiments, two R[S] attached to the same nitrogen atom are joined to form an optionally substituted heteroaryl ring.

In certain embodiments R[1] is:

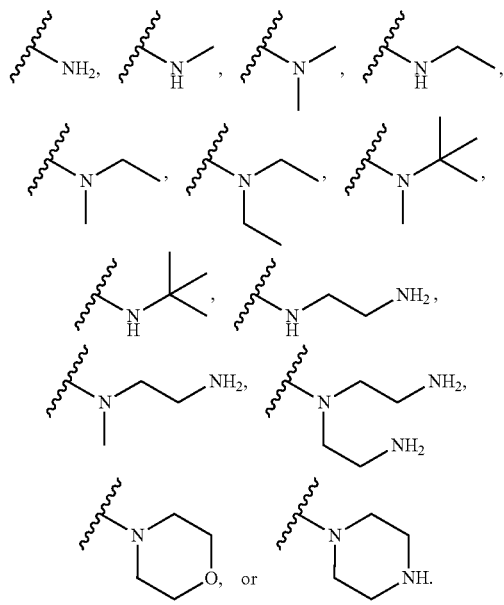

In certain embodiments, R[1] is of the formula:

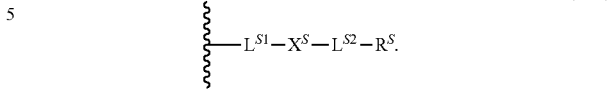

(L[S]-i)

In certain embodiments, L[S1] is a bond. In certain embodiments, L[S1] is —NR[S]—. In some embodiments, L[S1] is —NH—. In certain embodiments, L[S1] is —O—. In certain embodiments, L[S1] is —S—. In certain embodiments, L[S1] is optionally substituted alkylene. In certain embodiments, L[S1] is optionally substituted alkenylene. In certain embodiments, L[S1] is optionally substituted alkynylene. In certain embodiments, L[S1] is optionally substituted heteroalkylene. In certain embodiments, L[S1] is optionally substituted heteroalkenylene. In certain embodiments, L[S1] is optionally substituted heteroalkynylene. In certain embodiments, L[S2] is a bond. In certain embodiments, L[S2] is —NR[S]—. In some embodiments, L[S2] is —NH—. In certain embodiments, L[S2] is —O—. In certain embodiments, L[S2] is —S—. In certain embodiments, L[S2] is optionally substituted alkylene. In certain embodiments, L[S2] is optionally substituted alkenylene. In certain embodiments, L[S2] is optionally substituted alkynylene. In certain embodiments, L[S2] is optionally substituted heteroalkylene. In certain embodiments, L[S2] is optionally substituted heteroalkenylene. In certain embodiments, L[S2] is optionally substituted heteroalkynylene. In certain embodiments, X[S] is —C(=O)—. In certain embodiments, X[S] is —C(=NR[SN]). In some embodiments, X[S] is —C(=NH)—. In certain embodiments, X[S] is —S(=O)—. In certain embodiments, X[S] is —S(=O)[2]—. In certain embodiments, at least one R[S] is optionally substituted alkyl. In some embodiments, at least one R[S] is optionally substituted $C_1$-$C_6$ alkyl. In some embodiments, at least one R[S] is $C_1$-$C_6$ alkyl. In some embodiments, at least one R[S] is ethyl. In some embodiments, at least one R[S] is propyl. In some embodiments, R[S] is optionally substituted alkenyl. In some embodiments, R is optionally substituted alkynyl. In some embodiments, at least one R[S] is optionally substituted carbocyclyl. In some embodiments, at least one R[S] is optionally substituted heterocyclyl. In some embodiments, at least one R[S] is optionally substituted aryl. In some embodiments, at least one R[S] is optionally substituted phenyl. In some embodiments, at least one R[S] is optionally substituted heteroaryl. In certain embodiments, at least one R[S] is a nitrogen protecting group. In some embodiments, at least one R[S] is benzyl. In some embodiments, at least one R[S] is alkoxycarbonyl. In some embodiments, at least one R[S] is methoxycarbonyl or tert-butoxycarbonyl. In some embodiments, at least one R[S] is carbobenzyloxy, fluorophenylmethyloxycarbonyl, acetyl, benzoyl, p-toluenesulfonyl, p-bromobenzenesulfonyl chloride, 2-nitrobenzenesulfonyl, 4-nitrobenzenesulfonyl, methanesulfonyl, or trifluoromethanesulfonyl. In certain embodiments, R[S] is an oxygen protecting group. In some embodiments, R[S] is alkoxycarbonyl. In some embodiments, R[S] is methoxycarbonyl. In some embodiments, R[S] is acetyl, benzoyl, benzyl, methoxymethyl ether, p-methoxybenzyl ether, methylthiomethylether, pivaloyl, tetrahydropyranyl, tetrahydrofuranyl, triphenylmethyl, or silyl (e.g., trimethyl silyl, tert-butyldimethylsilyl, triisopropylsilyloxymethyl, triisopropylsilyl).

In certain embodiments, R¹ is —NHC(=O)R^S, —NHC(=O)OR^S, or —NHC(=O)N(R^S)₂. In certain embodiments, R¹ is:

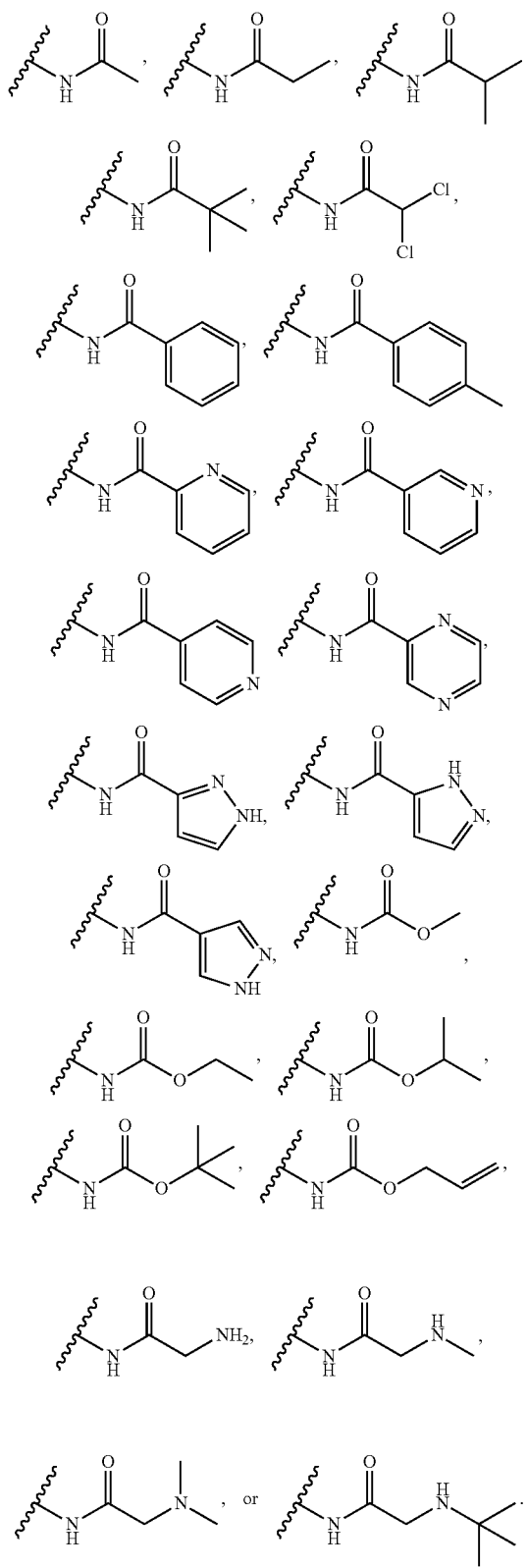

In certain embodiments, R¹ is —NHC(=NR^SN)R^S, —NHC(=NR^SN)OR^S, or —NHC(=NR^SN)N(R^S)₂. In certain embodiments, R¹ is:

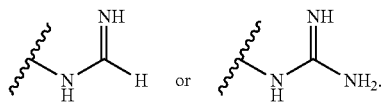

In certain embodiments, R¹ is —NHS(=O)₂R^S In certain embodiments, R¹ is:

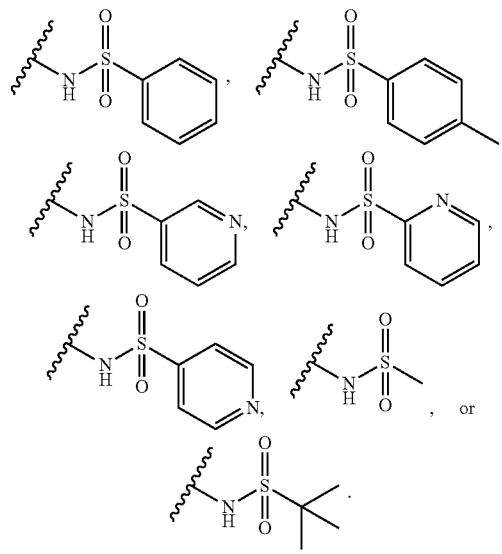

Group R^{1a}

Compounds of Formula (J) include R^{1a}, which may be —N(R^S)₂, —NR^S(OR^S), or of formula:

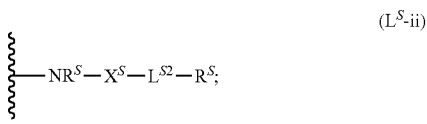

(L^S-ii)

wherein R^S, X^S, and L^{S2} are as defined for compounds of Formula (J). In some embodiments, R^{1a} is —NR^S(OR^S). R^{1a} may be —N(R^S)₂. The R^S groups of —N(R^S)₂ may be the same or different. In certain embodiments, R^{1a} is —NHR^S. In certain embodiments, R^{1a} is —NMeR^S. In some embodiments, R^{1a} is —NH₂. In some embodiments, at least one R^S is optionally substituted alkyl. In some embodiments, at least one R^S is optionally substituted $C_1$-$C_6$ alkyl. In some embodiments, at least one R^S is $C_1$-$C_6$ alkyl. In some embodiments, at least one R^S is ethyl. In some embodiments, at least one R^S is propyl. In some embodiments, R^S is optionally substituted alkenyl. In some embodiments, R^S is optionally substituted alkynyl. In some embodiments, at least one R^S is optionally substituted carbocyclyl. In some embodiments, at least one R^S is optionally substituted heterocyclyl. In some embodiments, at least one R^S is optionally substituted aryl. In some embodiments, at least one R^S is optionally substituted phenyl. In some embodiments, at least one R^S is optionally substituted heteroaryl. In certain embodiments, at least one R^S is a nitrogen protecting group.

In some embodiments, at least one $R^S$ is benzyl. In some embodiments, at least one $R^S$ is alkoxycarbonyl. In some embodiments, at least one $R^S$ is methoxycarbonyl or tert-butoxycarbonyl. In some embodiments, at least one $R^S$ is carbobenzyloxy, fluorophenylmethyloxycarbonyl, acetyl, benzoyl, p-toluenesulfonyl, p-bromobenzenesulfonyl, 2-nitrobenzenesulfonyl, 4-nitrobenzenesulfonyl, methanesulfonyl, or trifluoromethanesulfonyl. In certain embodiments, two $R^S$ attached to the same nitrogen atom are taken together to form $=N_2$, i.e. $-N(R^S)_2$ is $-N_3$. In certain embodiments, two $R^S$ attached to the same nitrogen atom are joined to form an optionally substituted heterocyclyl ring. In certain embodiments, two $R^S$ attached to the same nitrogen atom are joined to form an optionally substituted heteroaryl ring. In certain embodiments $R^{1a}$ is:

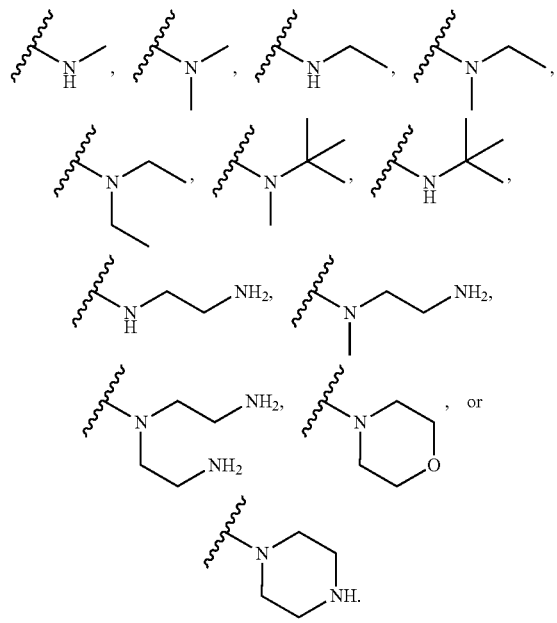

$R^{1a}$ may be of formula:

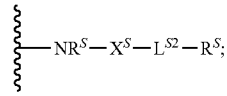

$(L^S\text{-ii})$

In certain embodiments, $L^{S2}$ is a bond. In certain embodiments, $L^{S2}$ is $-NR^S-$. In some embodiments, $L^{S2}$ is $-NH-$. In certain embodiments, $L^{S2}$ is $-O-$. In certain embodiments, $L^{S2}$ is $-S-$. In certain embodiments, $L^{S2}$ is optionally substituted alkylene. In certain embodiments, $L^{S2}$ is optionally substituted alkenylene. In certain embodiments, $L^{S2}$ is optionally substituted alkynylene. In certain embodiments, $L^{S2}$ is optionally substituted heteroalkylene. In certain embodiments, $L^{S2}$ is optionally substituted heteroalkenylene. In certain embodiments, $L^{S2}$ is optionally substituted heteroalkynylene. In certain embodiments, $X^S$ is $-C(=O)-$. In certain embodiments, $X^S$ is $-C(=NR^{SN})-$. In some embodiments, $X^S$ is $-C(=NH)-$. In certain embodiments, $X^S$ is $-S(=O)-$. In certain embodiments, $X^S$ is $-S(=O)_2-$. In some embodiments, at least one $R^S$ is optionally substituted alkyl.

In some embodiments, at least one $R^S$ is optionally substituted $C_1$-$C_6$ alkyl. In some embodiments, at least one $R^S$ is $C_1$-$C_6$ alkyl. In some embodiments, at least one $R^S$ is ethyl. In some embodiments, at least one $R^S$ is propyl. In some embodiments, $R^S$ is optionally substituted alkenyl. In some embodiments, $R^S$ is optionally substituted alkynyl. In some embodiments, at least one $R^S$ is optionally substituted carbocyclyl. In some embodiments, at least one $R^S$ is optionally substituted heterocyclyl. In some embodiments, at least one $R^S$ is optionally substituted aryl. In some embodiments, at least one $R^S$ is optionally substituted phenyl. In some embodiments, at least one $R^S$ is optionally substituted heteroaryl. In certain embodiments, at least one $R^S$ is a nitrogen protecting group. In some embodiments, at least one $R^S$ is benzyl. In some embodiments, at least one $R^S$ is alkoxycarbonyl. In some embodiments, at least one $R^S$ is methoxycarbonyl or tert-butoxycarbonyl. In some embodiments, at least one $R^S$ is carbobenzyloxy, fluorophenylmethyloxycarbonyl, acetyl, benzoyl, p-toluenesulfonyl, p-bromobenzenesulfonyl chloride, 2-nitrobenzenesulfonyl, 4-nitrobenzenesulfonyl, methanesulfonyl, or trifluoromethanesulfonyl. In certain embodiments, $R^S$ is an oxygen protecting group. In some embodiments, $R^S$ is alkoxycarbonyl. In some embodiments, $R^S$ is methoxycarbonyl. In some embodiments, $R^S$ is acetyl, benzoyl, benzyl, methoxymethyl ether, p-methoxybenzyl ether, methylthiomethylether, pivaloyl, tetrahydropyranyl, tetrahydrofuranyl, triphenylmethyl, or silyl (e.g., trimethyl silyl, tert-butyldimethylsilyl, triisopropylsilyloxymethyl, triisopropylsilyl).

In certain embodiments, $R^{1a}$ is $-NHC(=O)R^S$, $-NHC(=O)OR^S$, or $-NHC(=O)N(R^S)_2$. In certain embodiments, $R^{1a}$ is:

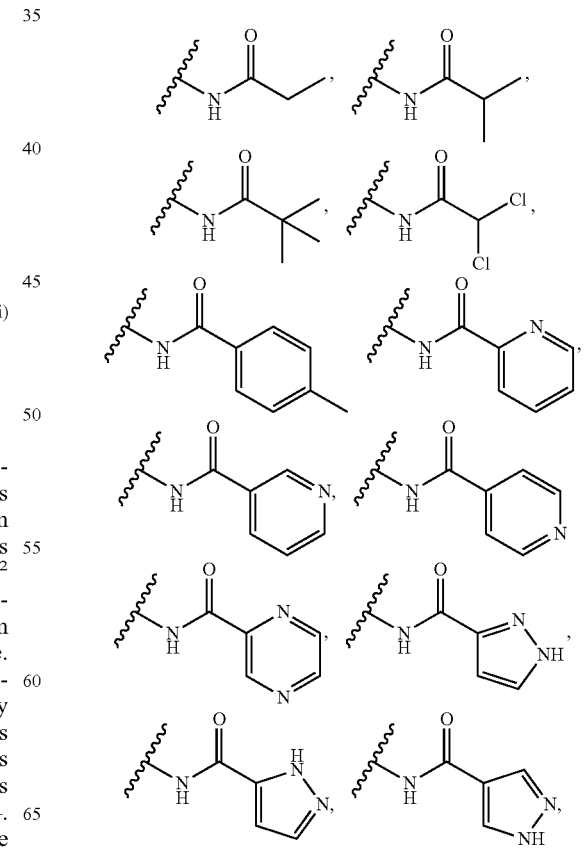

-continued

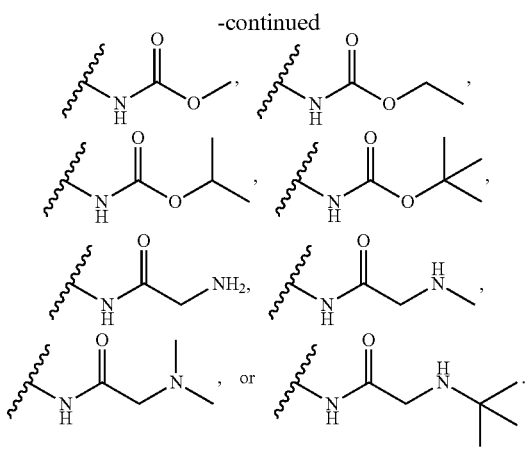

In certain embodiments, $R^{1a}$ is —NHC(=NR$^{SN}$)R$^S$, —NHC(=NR$^{SN}$)OR$^S$, or —NHC(=NR$^{SN}$)N(R$^S$)$_2$. In certain embodiments, $R^{1a}$ is:

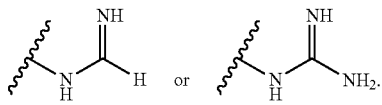

In certain embodiments, $R^{1a}$ is —NHS(=O)$_2$R$^S$. In certain embodiments, $R^{1a}$ is:

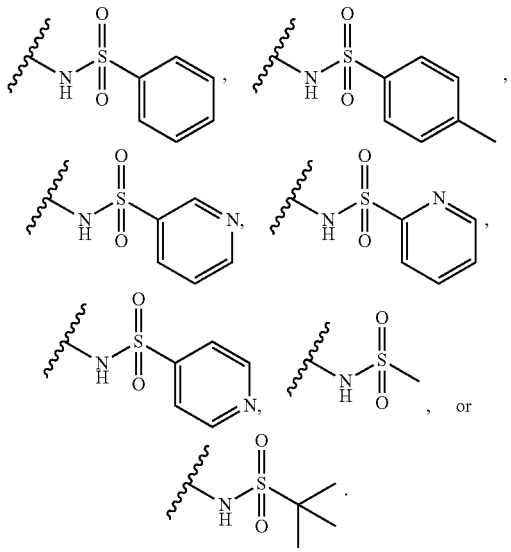

Group $R^{1b}$

Compounds of Formula (J) include $R^{1b}$, which may be —N(R$^S$)$_2$, —NR$^S$(OR$^S$), or of formula:

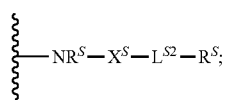
(L$^S$-ii)

wherein R$^S$, X$^S$, are L$^{S2}$ are as defined for compounds of Formula (J). In some embodiments, $R^{1b}$ is —NR$^S$(OR$^S$). $R^{1b}$ may be —N(R$^S$)$_2$. The R$^S$ groups of —N(R$^S$)$_2$ may be the same or different. In certain embodiments, $R^{1b}$ is NHR$^S$. In certain embodiments, $R^{1b}$ is —NMeR$^S$. In some embodiments, $R^{1b}$ is —NH$_2$. In some embodiments, at least one R$^S$ is optionally substituted alkyl. In some embodiments, at least one R$^S$ is optionally substituted C$_1$-C$_6$ alkyl. In some embodiments, at least one R$^S$ is C$_1$-C$_6$ alkyl. In some embodiments, at least one R$^S$ is ethyl. In some embodiments, at least one R$^S$ is propyl. In some embodiments, R$^S$ is optionally substituted alkenyl. In some embodiments, R$^S$ is optionally substituted alkynyl. In some embodiments, at least one R$^S$ is optionally substituted carbocyclyl. In some embodiments, at least one R$^S$ is optionally substituted heterocyclyl. In some embodiments, at least one R$^S$ is optionally substituted aryl. In some embodiments, at least one R$^S$ is optionally substituted phenyl. In some embodiments, at least one R$^S$ is optionally substituted heteroaryl. In certain embodiments, at least one R$^S$ is a nitrogen protecting group. In some embodiments, at least one R$^S$ is benzyl. In some embodiments, at least one R$^S$ is alkoxycarbonyl. In some embodiments, at least one R$^S$ is methoxycarbonyl or tert-butoxycarbonyl. In some embodiments, at least one R$^S$ is carbobenzyloxy, fluorophenylmethyloxycarbonyl, acetyl, benzoyl, p-toluenesulfonyl, p-bromobenzenesulfonyl, 2-nitrobenzenesulfonyl, 4-nitrobenzenesulfonyl, methanesulfonyl, or trifluoromethanesulfonyl. In certain embodiments, two R$^S$ attached to the same nitrogen atom are taken together to form =N$_2$, i.e. —N(R$^S$)$_2$ is —N$_3$. In certain embodiments, two R$^S$ attached to the same nitrogen atom are joined to form an optionally substituted heterocyclyl ring. In certain embodiments, two R$^S$ attached to the same nitrogen atom are joined to form an optionally substituted heteroaryl ring. In certain embodiments $R^{1b}$ is:

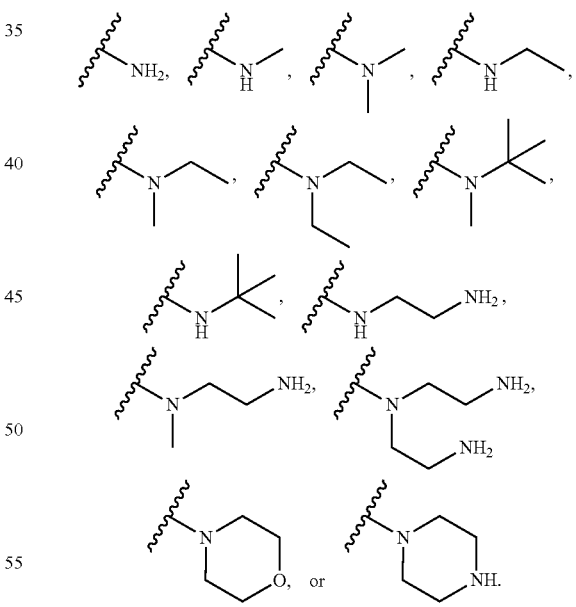

$R^{1b}$ may be of formula:

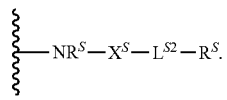
(L$^S$-ii)

In certain embodiments, $L^{S2}$ is a bond. In certain embodiments, $L^{S2}$ is —$NR^S$—. In some embodiments, $L^{S2}$ is —NH—. In certain embodiments, $L^{S2}$ is —O—. In certain embodiments, $L^{S2}$ is —S—. In certain embodiments, $L^{S2}$ is optionally substituted alkylene. In certain embodiments, $L^{S2}$ is optionally substituted alkenylene. In certain embodiments, $L^{S2}$ is optionally substituted alkynylene. In certain embodiments, $L^{S2}$ is optionally substituted heteroalkylene. In certain embodiments, $L^{S2}$ is optionally substituted heteroalkenylene. In certain embodiments, $L^{S2}$ is optionally substituted heteroalkynylene. In certain embodiments, $X^S$ is —C(=O)—. In certain embodiments, $X^S$ is —C(=$NR^{SN}$)—. In some embodiments, $X^S$ is —C(=NH)—. In certain embodiments, $X^S$ is —S(=O)—. In certain embodiments, $X^S$ is —S(=O)$_2$—. In some embodiments, at least one $R^S$ is optionally substituted alkyl. In some embodiments, at least one $R^S$ is optionally substituted $C_1$-$C_6$ alkyl. In some embodiments, at least one $R^S$ is $C_1$-$C_6$ alkyl. In some embodiments, at least one $R^S$ is ethyl. In some embodiments, at least one $R^S$ is propyl. In some embodiments, $R^S$ is optionally substituted alkenyl. In some embodiments, $R^S$ is optionally substituted alkynyl. In some embodiments, at least one $R^S$ is optionally substituted carbocyclyl. In some embodiments, at least one $R^S$ is optionally substituted heterocyclyl. In some embodiments, at least one $R^S$ is optionally substituted aryl. In some embodiments, at least one $R^S$ is optionally substituted phenyl. In some embodiments, at least one $R^S$ is optionally substituted heteroaryl. In certain embodiments, at least one $R^S$ is a nitrogen protecting group. In some embodiments, at least one $R^S$ is benzyl. In some embodiments, at least one $R^S$ is alkoxycarbonyl. In some embodiments, at least one $R^S$ is methoxycarbonyl or tert-butoxycarbonyl. In some embodiments, at least one $R^S$ is carbobenzyloxy, fluorophenylmethyloxycarbonyl, acetyl, benzoyl, p-toluenesulfonyl, p-bromobenzenesulfonyl chloride, 2-nitrobenzenesulfonyl, 4-nitrobenzenesulfonyl, methanesulfonyl, or trifluoromethanesulfonyl. In certain embodiments, $R^S$ is an oxygen protecting group. In some embodiments, $R^S$ is alkoxycarbonyl. In some embodiments, $R^S$ is methoxycarbonyl. In some embodiments, $R^S$ is acetyl, benzoyl, benzyl, methoxymethyl ether, p-methoxybenzyl ether, methylthiomethylether, pivaloyl, tetrahydropyranyl, tetrahydrofuranyl, triphenylmethyl, or silyl (e.g., trimethyl silyl, tert-butyldimethylsilyl, triisopropylsilyloxymethyl, triisopropylsilyl).

In certain embodiments, $R^{1b}$ is —NHC(=O)$R^S$, —NHC(=O)O$R^S$, or —NHC(=O)N($R^S$)$_2$. In certain embodiments, $R^{1b}$ is:

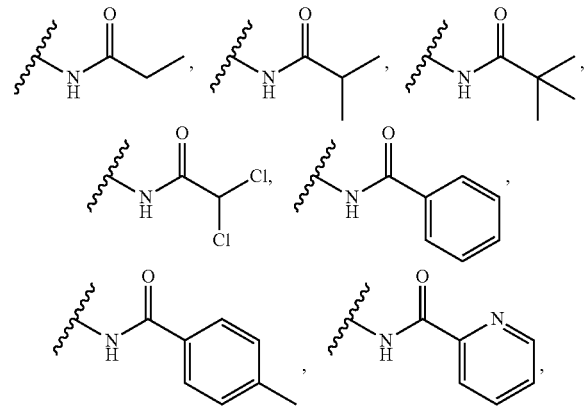

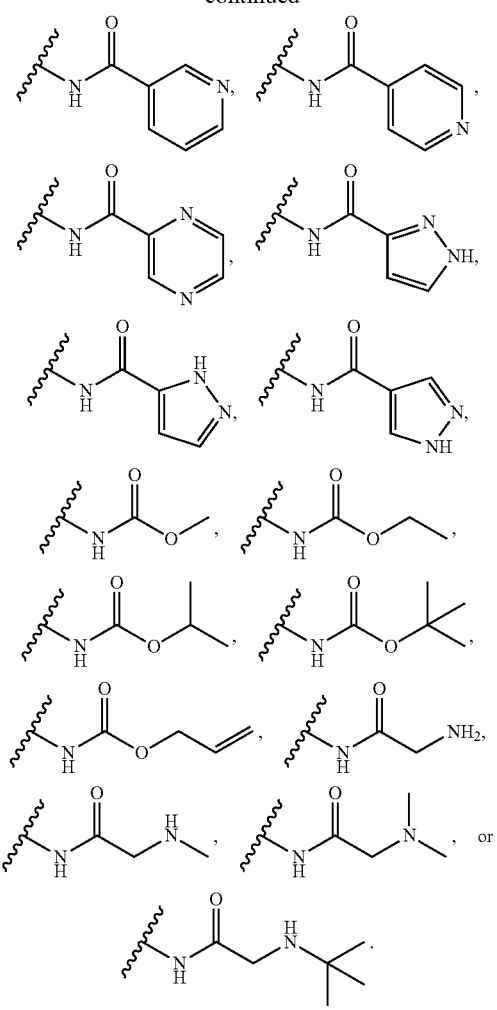

In certain embodiments, $R^{1b}$ is —NHC(=$NR^{SN}$)$R^S$, —NHC(=$NR^{SN}$)O$R^S$, or —NHC(=$NR^{SN}$)N($R^S$)$_2$. In certain embodiments, $R^{1b}$ is

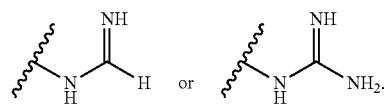

In certain embodiments, —NHS(=O)$_2R^S$ In certain embodiments, $R^{1b}$ is:

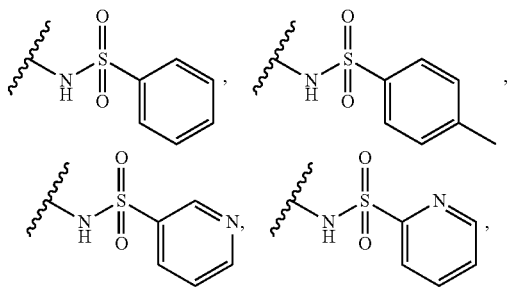

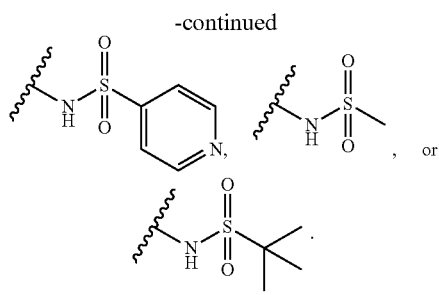
, or

Groups R² and R³

Compounds of Formulae (A), (B), (B'), (C'), (D'), (Q), and (R) include R² and R³, which each may independently be hydrogen, halogen, optionally substituted $C_1$-$C_6$ alkyl, —$R^{SO}$, or —$N(R^{SN})_2$. In certain embodiments, R² and R³ are both hydrogen. In certain embodiments, at least one of R² and R³ is hydrogen. In some embodiments, R² is hydrogen. In some embodiments, R² is optionally substituted $C_1$-$C_6$ alkyl. In some embodiments, R² is $C_1$-$C_6$ alkyl. In some embodiments, R² is methyl. In some embodiments, R² is ethyl, propyl, or butyl. In some embodiments, R² is —F. In some embodiments, R² is —Cl, —Br, or —I. In certain embodiments, R² is —$OR^{SO}$. In some embodiments, R² is —OH. In some embodiments, R² is methoxy, ethoxy, propoxy, or butoxy. In some embodiments, R² is —$OR^{SO}$, and $R^{SO}$ is an oxygen protecting group (e.g., alkoxycarbonyl). In certain embodiments R² is —$N(R^{SN})_2$ In some embodiments, R² is —$NHR^{SN}$. In some embodiments, R² is —$NH_2$. In some embodiments, R² is —NHMe or —$NMe_2$. In some embodiments, R² is —$NHR^{SN}$, and $R^{SN}$ is a nitrogen protecting group. In some embodiments, R³ is hydrogen. In some embodiments, R³ is optionally substituted $C_1$-$C_6$ alkyl. In some embodiments, R³ is $C_1$-$C_6$ alkyl. In some embodiments, R³ is methyl. In some embodiments, R³ is ethyl, propyl, or butyl. In some embodiments, R³ is —F. In some embodiments, R³ is —Cl, —Br, or —I. In certain embodiments, R³ is —$OR^{SO}$. In some embodiments, R³ is —OH. In some embodiments, R³ is methoxy, ethoxy, propoxy, or butoxy. In some embodiments, R³ is —$OR^{SO}$, and $R^{SO}$ is an oxygen protecting group (e.g., alkoxycarbonyl). In certain embodiments R³ is —$N(R^{SN})_2$. In some embodiments, R³ is —$NHR^{SN}$. In some embodiments, R³ is —$NH_2$. In some embodiments, R³ is —NHMe or —$NMe_2$. In some embodiments, R³ is —$NHR^{SN}$, and RN is a nitrogen protecting group.

Groups $R^{2a}$ and $R^{3a}$

Compounds of Formula (J) include $R^{2a}$ and $R^{3a}$, which each may independently be hydrogen, halogen, optionally substituted $C_1$-$C_6$ alkyl, or —$OR^{SO}$. In certain embodiments, $R^{2a}$ and $R^{3a}$ are hydrogen. In certain embodiments, at least one of $R^{2a}$ and $R^{3a}$ is hydrogen. In some embodiments, $R^{2a}$ is hydrogen. In some embodiments, $R^{2a}$ is optionally substituted $C_1$-$C_6$ alkyl. In some embodiments, $R^{2a}$ is $C_1$-$C_6$ alkyl. In some embodiments, $R^{2a}$ is methyl. In some embodiments, $R^{2a}$ is ethyl, propyl, or butyl. In some embodiments, $R^{2a}$ is —F. In some embodiments, $R^{2a}$ is —Cl, —Br, or —I. In certain embodiments, $R^{2a}$ is —$OR^{SO}$. In some embodiments, $R^{2a}$ is —OH. In some embodiments, $R^{2a}$ is methoxy, ethoxy, propoxy, or butoxy. In some embodiments, $R^{2a}$ is —$OR^{SO}$, and $R^{SO}$ is an oxygen protecting group (e.g., alkoxycarbonyl). In some embodiments, $R^{3a}$ is hydrogen. In some embodiments, $R^{3a}$ is optionally substituted $C_1$-$C_6$ alkyl. In some embodiments, $R^{3a}$ is $C_1$-$C_6$ alkyl. In some embodiments, $R^{3a}$ is methyl. In some embodiments, $R^{3a}$ is ethyl, propyl, or butyl. In some embodiments, $R^{3a}$ is —F. In some embodiments, $R^{3a}$ is —Cl, —Br, or —I. In certain embodiments, $R^{3a}$ is —$OR^{SO}$. In some embodiments, $R^{3a}$ is —OH. In some embodiments, $R^{3a}$ is methoxy, ethoxy, propoxy, or butoxy. In some embodiments, $R^{3a}$ is —$OR^{SO}$, and $R^{SO}$ is an oxygen protecting group (e.g., alkoxycarbonyl).

Groups $R^{2b}$ and $R^{3b}$

Compounds of Formula (K) include $R^{2b}$ and $R^{3b}$, which each may independently be hydrogen, halogen, optionally substituted $C_1$-$C_6$ alkyl, —$OR^{SO}$. In certain embodiments, $R^{2b}$ and $R^{3b}$ are hydrogen. In certain embodiments, at least one of $R^{2b}$ and $R^{3b}$ is hydrogen. In some embodiments, $R^{2b}$ is hydrogen. In some embodiments, $R^{2b}$ is optionally substituted $C_1$-$C_6$ alkyl. In some embodiments, $R^{2b}$ is $C_1$-$C_6$ alkyl. In some embodiments, $R^{2b}$ is methyl. In some embodiments, $R^{2b}$ is ethyl, propyl, or butyl. In some embodiments, $R^{2b}$ is —F. In some embodiments, $R^{2b}$ is —Cl, —Br, or —I. In certain embodiments, $R^{2b}$ is —$OR^{SO}$. In some embodiments, $R^{2b}$ is —OH. In some embodiments, $R^{2b}$ is methoxy, ethoxy, propoxy, or butoxy. In some embodiments, $R^{2b}$ is —$OR^{SO}$, and $R^{SO}$ is an oxygen protecting group (e.g., alkoxycarbonyl). In some embodiments, $R^{3b}$ is hydrogen. In some embodiments, $R^{3b}$ is optionally substituted $C_1$-$C_6$ alkyl. In some embodiments, $R^{3b}$ is $C_1$-$C_6$ alkyl. In some embodiments, $R^{3b}$ is methyl. In some embodiments, $R^{3b}$ is ethyl, propyl, or butyl. In some embodiments, $R^{3b}$ is —F. In some embodiments, $R^{3b}$ is —Cl, —Br, or —I. In certain embodiments, $R^{3b}$ is —$OR^{SO}$. In some embodiments, $R^{3b}$ is —OH. In some embodiments, $R^{3b}$ is methoxy, ethoxy, propoxy, or butoxy. In some embodiments, $R^{3b}$ is —$OR^{SO}$, and $R^{SO}$ is an oxygen protecting group (e.g., alkoxycarbonyl).

Groups $R^{4a}$ and $R^{4b}$

Compounds of Formulae (A), (B), (B'), (C'), (D'), (J), (K), and (Q) include $R^{4a}$ and $R^{4b}$, which each may independently be hydrogen, halogen, optionally substituted $C_1$-$C_6$ alkyl, or —$OR^{SO}$. Compounds of Formula (R) also include group $R^{4a}$. In certain embodiments, $R^{4a}$ and R³ are hydrogen. In certain embodiments, at least one of $R^{4a}$ and R³ is hydrogen. In some embodiments, $R^{4a}$ is hydrogen. In some embodiments, $R^{4a}$ is optionally substituted $C_1$-$C_6$ alkyl. In some embodiments, $R^{4a}$ is $C_1$-$C_6$ alkyl. In some embodiments, $R^{4a}$ is methyl. In some embodiments, $R^{4a}$ is ethyl, propyl, or butyl. In some embodiments, $R^{4a}$ is —F. In some embodiments, $R^{4a}$ is —Cl, —Br, or —I. In certain embodiments, $R^{4a}$ is —$OR^{SO}$. In some embodiments, $R^{4a}$ is —OH. In some embodiments, $R^{4a}$ is methoxy, ethoxy, propoxy, or butoxy. In some embodiments, $R^{4b}$ is —$OR^{SO}$, and $R^{SO}$ is an oxygen protecting group (e.g., alkoxycarbonyl). In some embodiments, $R^{4a}$ is —$OR^{SO}$, and $R^{SO}$ is a carbohydrate. In some embodiments, $R^{4b}$ is —$OR^{SO}$, and $R^{SO}$ is a monosaccharide. In some embodiments, $R^{4b}$ is hydrogen. In some embodiments, $R^{4b}$ is optionally substituted $C_1$-$C_6$ alkyl. In some embodiments, $R^{4b}$ is $C_1$-$C_6$ alkyl. In some embodiments, $R^{4b}$ is methyl. In some embodiments, $R^{4b}$ is ethyl, propyl, or butyl. In some embodiments, $R^{4b}$ is —F. In some embodiments, $R^{4b}$ is —Cl, —Br, or —I. In certain embodiments, $R^{4b}$ is —$OR^{SO}$. In some embodiments, $R^{4b}$ is —OH. In some embodiments, $R^{4b}$ is methoxy, ethoxy, propoxy, or butoxy. In some embodiments, $R^{4b}$ is —$OR^{SO}$, and $R^{SO}$ is an oxygen protecting group (e.g., alkoxycarbonyl). In some embodiments, $R^{4b}$ is —$OR^{SO}$, and $R^{SO}$ is a carbohydrate. In some embodiments, $R^{4b}$ is —$OR^{SO}$, and $R^{SO}$ is a monosaccharide.

Groups R⁵ and R⁶

Compounds of Formula (B'), (C'), (D'), (J), and (K) include R⁵ and R⁶, which each may independently be hydrogen, optionally substituted $C_1$-$C_6$ alkyl, a carbohydrate, or an oxygen protecting group. In certain embodiments, $R^5$ and $R^6$ are hydrogen. In certain embodiments, at least one of $R^5$ and $R^6$ is hydrogen. In certain embodiments, $R^5$ and $R^6$ are both oxygen protecting groups. In certain embodiments, $R^5$ and $R^6$ are both identical oxygen protecting groups. In some embodiments, $R^5$ is hydrogen. In some embodiments, $R^5$ is optionally substituted $C_1$-$C_6$ alkyl. In some embodiments, $R^5$ is $C_1$-$C_6$ alkyl. In some embodiments, $R^5$ is methyl. In some embodiments, $R^5$ is ethyl, propyl, or butyl. In certain embodiments, $R^5$ is an oxygen protecting group. In some embodiments, $R^5$ is alkoxycarbonyl. In some embodiments, $R^5$ is methoxycarbonyl. In some embodiments, $R^5$ is acetyl, benzoyl, benzyl, methoxymethyl ether, p-methoxybenzyl ether, methylthiomethylether, pivaloyl, tetrahydropyranyl, tetrahydrofuranyl, triphenylmethyl, or silyl (e.g., trimethyl silyl, tert-butyldimethylsilyl, triisopropylsilyloxymethyl, triisopropylsilyl). In some embodiments, $R^5$ is a carbohydrate. In some embodiments, $R^5$ is a monosaccharide. In some embodiments, $R^6$ is hydrogen. In some embodiments, $R^6$ is optionally substituted $C_1$-$C_6$ alkyl. In some embodiments, $R^6$ is $C_1$-$C_6$ alkyl. In some embodiments, $R^6$ is methyl. In some embodiments, $R^6$ is ethyl, propyl, or butyl. In certain embodiments, $R^6$ is an oxygen protecting group. In some embodiments, $R^6$ is alkoxycarbonyl. In some embodiments, $R^6$ is methoxycarbonyl. In some embodiments, $R^6$ is acetyl, benzoyl, benzyl, methoxymethyl ether, p-methoxybenzyl ether, methylthiomethylether, pivaloyl, tetrahydropyranyl, tetrahydrofuranyl, triphenylmethyl, or silyl (e.g., trimethyl silyl, tert-butyldimethylsilyl, triisopropylsilyloxymethyl, triisopropylsilyl). In some embodiments, $R^6$ is a carbohydrate. In some embodiments, $R^6$ is a monosaccharide.

Groups $R^7$ and $R^8$

Compounds of Formula (D') include $R^7$ and $R^8$, which each may independently be hydrogen, optionally substituted $C_1$-$C_6$ alkyl, optionally substituted carbocyclyl, optionally substituted heterocyclyl, optionally substituted aryl, optionally substituted heteroaryl, optionally substituted acyl, or a nitrogen protecting group, or $R^7$ and $R^8$ may be joined to form an optionally substituted heterocyclyl or heteroaryl ring. In certain embodiments, $R^7$ and $R^8$ are each independently hydrogen, optionally substituted $C_1$-$C_6$ alkyl, or a nitrogen protecting group, or $R^7$ and $R^8$ may be joined to form an optionally substituted heterocyclyl or heteroaryl ring. In certain embodiments, at least one of $R^7$ and $R^8$ is hydrogen. In certain embodiments, $R^7$ and $R^8$ are joined to form an optionally substituted heterocyclyl ring. In certain embodiments, $R^7$ and $R^8$ are joined to form an optionally substituted heteroaryl ring. In certain embodiments, $R^7$ and $R^8$ are optionally substituted $C_1$-$C_6$ alkyl. In certain embodiments, $R^7$ and $R^8$ are $C_1$-$C_6$ alkyl. In certain embodiments, $R^7$ and $R^8$ are methyl. In certain embodiments, $R^7$ and $R^8$ are both ethyl, both propyl, or both butyl. In certain embodiments, $R^7$ and $R^8$ are independently methyl, propyl, or butyl. In certain embodiments, $R^7$ and $R^8$ are both nitrogen protecting groups. In certain embodiments, $R^7$ and $R^8$ are both identical nitrogen protecting groups. In certain embodiments, $R^7$ is hydrogen, and $R^8$ is optionally substituted $C_1$-$C_6$ alkyl. In certain embodiments, $R^7$ is hydrogen, and $R^8$ is $C_1$-$C_6$ alkyl. In certain embodiments, $R^7$ is hydrogen, and $R^8$ is methyl. In certain embodiments, $R^7$ is hydrogen, and $R^8$ is ethyl, propyl, or butyl. In certain embodiments, $R^7$ is hydrogen, and $R^8$ is a nitrogen protecting group. In certain embodiments, $R^7$ is hydrogen, and $R^8$ is benzyl. In certain embodiments, $R^7$ is hydrogen, and $R^8$ is alkoxycarbonyl (e.g., methoxycarbonyl, tert-butylcarbonyl). In certain embodiments, $R^7$ is hydrogen, and $R^8$ is carbobenzyloxy, fluorophenylmethyloxycarbonyl, acetyl, benzoyl, p-toluenesulfonyl, p-bromobenzenesulfonyl, 2-nitrobenzenesulfonyl, 4-nitrobenzenesulfonyl, methanesulfonyl, or trifluoromethanesulfonyl.

Groups $R^{7a}$ and $R^{8a}$

Compounds of Formula (J) include $R^{7a}$ and $R^{8a}$, which each may independently be hydrogen, optionally substituted $C_1$-$C_6$ alkyl, optionally substituted carbocyclyl, optionally substituted heterocyclyl, optionally substituted aryl, optionally substituted heteroaryl, optionally substituted acyl, or a nitrogen protecting group, or $R^{7a}$ and $R^{8a}$ may be joined to form an optionally substituted heterocyclyl or heteroaryl ring. In certain embodiments, $R^{7a}$ and $R^{8a}$ are each independently hydrogen, optionally substituted $C_1$-$C_6$ alkyl, or a nitrogen protecting group, or $R^{7a}$ and $R^{8a}$ may be joined to form an optionally substituted heterocyclyl or heteroaryl ring. In certain embodiments, at least one of $R^{7a}$ and $R^{8a}$ is hydrogen. In certain embodiments, $R^{7a}$ and $R^{8a}$ are joined to form an optionally substituted heterocyclyl ring. In certain embodiments, $R^{7a}$ and $R^{8a}$ are joined to form an optionally substituted heteroaryl ring. In certain embodiments, $R^{7a}$ and $R^{8a}$ are optionally substituted $C_1$-$C_6$ alkyl. In certain embodiments, $R^{7a}$ and $R^{8a}$ are $C_1$-$C_6$ alkyl. In certain embodiments, $R^{7a}$ and $R^{8a}$ are methyl. In certain embodiments, $R^{7a}$ and $R^{8a}$ are both ethyl, both propyl, or both butyl. In certain embodiments, $R^{7a}$ and $R^{8a}$ are independently methyl, propyl, or butyl. In certain embodiments, $R^{7a}$ and $R^{8a}$ are both nitrogen protecting groups. In certain embodiments, $R^{7a}$ and $R^{8a}$ are both identical nitrogen protecting groups. In certain embodiments, $R^{7a}$ is hydrogen, and $R^{8a}$ is optionally substituted $C_1$-$C_6$ alkyl. In certain embodiments, $R^{7a}$ is hydrogen, and $R^{8a}$ is $C_1$-$C_6$ alkyl. In certain embodiments, $R^{7a}$ is hydrogen, and $R^{8a}$ is methyl. In certain embodiments, $R^{7a}$ is hydrogen, and $R^{8a}$ is ethyl, propyl, or butyl. In certain embodiments, $R^{7a}$ is hydrogen, and $R^{8a}$ is a nitrogen protecting group. In certain embodiments, $R^{7a}$ is hydrogen, and $R^{8a}$ is benzyl. In certain embodiments, $R^{7a}$ is hydrogen, and $R^{8a}$ is alkoxycarbonyl (e.g., methoxycarbonyl, tert-butylcarbonyl). In certain embodiments, $R^{7a}$ is hydrogen, and $R^{8a}$ is carbobenzyloxy, fluorophenylmethyloxycarbonyl, acetyl, benzoyl, p-toluenesulfonyl, p-bromobenzenesulfonyl, 2-nitrobenzenesulfonyl, 4-nitrobenzenesulfonyl, methanesulfonyl, or trifluoromethanesulfonyl.

Groups $R^S$, $R^{SO}$, and $R^{SN}$

Compounds of Formulae (A), (B), (B'), (C'), (D'), (Q), (J), (K), and (R) may include one or more $R^S$, which independently may be hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two $R^S$ attached to the same nitrogen atom may be taken together to form $=N_2$ or an optionally substituted heterocyclyl or heteroaryl ring. In some embodiments, $R^S$ is hydrogen. In some embodiments, $R^S$ is optionally substituted alkyl. In some embodiments, $R^S$ is optionally substituted $C_1$-$C_6$ alkyl. In some embodiments, $R^S$ is $C_1$-$C_6$ alkyl. In some embodiments, $R^S$ is methyl. In some embodiments, $R^S$ is ethyl, propyl, or butyl. In some embodiments, $R^S$ is optionally substituted alkenyl. In some embodiments, $R^S$ is optionally substituted alkynyl. In some embodiments, $R^S$ is optionally substituted carbocyclyl. In some embodiments, $R^S$ is optionally substituted heterocyclyl. In some embodiments, $R^S$ is optionally substituted aryl. In some embodiments, $R^S$ is optionally substituted phenyl. In some embodiments, $R^S$ is optionally substituted heteroaryl. In certain embodiments, $R^S$ is an oxygen protecting group. In some embodiments, $R^S$ is alkoxycarbonyl. In some embodiments, $R^S$ is methoxycarbonyl. In some embodiments, $R^S$ is acetyl, benzoyl, benzyl, methoxymethyl ether, p-methoxybenzyl ether, methylthiomethylether, pivaloyl, tetrahydropyranyl, tetrahydrofuranyl, triphenylmethyl, or silyl (e.g., trimethyl silyl, tert-butyldimethylsilyl, triisopropylsilyloxymethyl, triisopropylsilyl). In certain embodiments, $R^S$ is a carbohydrate. In certain embodiments, $R^S$ is a monosaccharide. In certain embodiments, at least one $R^S$ is a nitrogen protecting group. In some embodiments, at least one $R^S$ is benzyl. In some embodiments, at least one $R^S$ is alkoxycarbonyl. In some embodiments, at least one $R^S$ is methoxycarbonyl or tert-butoxycarbonyl. In some embodiments, at least one $R^S$ is carbobenzyloxy, fluorophenylmethyloxycarbonyl, acetyl, benzoyl, p-toluenesulfonyl, p-bromobenzenesulfonyl, 2-nitrobenzenesulfonyl, 4-nitrobenzenesulfonyl, methanesulfonyl, or trifluoromethanesulfonyl. In certain embodiments, two $R^S$ attached to the same nitrogen atom are taken together to form =$N_2$, i.e. —$N(R^S)_2$ is —$N_3$. In certain embodiments, two $R^S$ attached to the same nitrogen atom are joined to form an optionally substituted heterocyclyl ring. In certain embodiments, two $R^S$ attached to the same nitrogen atom are joined to form an optionally substituted heteroaryl ring. In certain embodiments, $R^S$ is a sulfur protecting group. In certain embodiments, $R^S$ is optionally substituted alkenyl. In certain embodiments, $R^S$ is optionally substituted alkynyl.

Compounds of Formula (A), (B), (B'), (C'), (D'), (Q), and (R) may include one or more $R^{SO}$, which independently may be hydrogen, optionally substituted $C_1$-$C_6$ alkyl, a carbohydrate, or an oxygen protecting group. In some embodiments, $R^{SO}$ is hydrogen. In some embodiments, $R^{SO}$ is optionally substituted $C_1$-$C_6$ alkyl. In some embodiments, $R^{SO}$ is $C_1$-$C_6$ alkyl. In some embodiments, $R^{SO}$ is methyl. In some embodiments, $R^{SO}$ is ethyl, propyl, or butyl. In certain embodiments, $R^{SO}$ is an oxygen protecting group. In some embodiments, $R^{SO}$ is alkoxycarbonyl. In some embodiments, $R^{SO}$ is methoxycarbonyl. In some embodiments, $R^{SO}$ is acetyl, benzoyl, benzyl, methoxymethyl ether, p-methoxybenzyl ether, methylthiomethylether, pivaloyl, tetrahydropyranyl, tetrahydrofuranyl, triphenylmethyl, or silyl (e.g., trimethyl silyl, tert-butyldimethylsilyl, triisopropylsilyloxymethyl, triisopropylsilyl). In some embodiments, $R^{SO}$ is a carbohydrate. In some embodiments, $R^{SO}$ is a monosaccharide.

Compounds of Formulae (A), (B), (B'), (C'), (D'), (Q), and (R) may include $R^{SO}$, which may independently be hydrogen, optionally substituted $C_1$-$C_6$ alkyl, or a nitrogen protecting group, or two $R^{SN}$ attached to the same nitrogen atom may be joined to form an optionally substituted heterocyclyl or heteroaryl ring. In certain embodiments, $R^{SN}$ is optionally substituted $C_1$-$C_6$ alkyl. In certain embodiments, $R^{SN}$ is $C_1$-$C_6$ alkyl. In certain embodiments, $R^{SN}$ is methyl. In certain embodiments, $R^{SN}$ is ethyl, propyl, or butyl. In certain embodiments, $R^{SN}$ is a nitrogen protecting group. In certain embodiments, $R^{SN}$ is benzyl. In certain embodiments, $R^{SN}$ is alkoxycarbonyl (e.g., methoxycarbonyl, tert-butylcarbonyl). In certain embodiments, $R^{SN}$ is carbobenzyloxy, fluorophenylmethyloxycarbonyl, acetyl, benzoyl, p-toluenesulfonyl, p-bromobenzenesulfonyl, 2-nitrobenzenesulfonyl, 4-nitrobenzenesulfonyl, methanesulfonyl, or trifluoromethanesulfonyl. In certain embodiments, two $R^{SN}$ attached to the same nitrogen atom are joined to form an optionally substituted heterocyclyl ring. In certain embodiments, two $R^{SN}$ attached to the same nitrogen atom are joined to form an optionally substituted heteroaryl ring.

Definitions

Chemical Terms

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *E. L. Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⁓⁓⁓ is a single bond where the stereochemistry of the moieties immediately attached thereto is not specified, − − − is absent or a single bond, and ═ or ═ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═$CHCH_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms, at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-8}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-s}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3{}^+$X$^-$, —N(OR$^{cc}$)R$^{bb}$, —SH, —SR$^{aa}$, —SSR$^{cc}$, —C(=O)R$^{cc}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{aa}$ groups;

each instance of R$^{bb}$ is, independently, selected from hydrogen, —OH, —O$^{aa}$, —N(R$^{cc}$)$_2$, —CN, —C(=O)R$^{aa}$, —C(=O)N(R$^{cc}$)$_2$, —CO$_2$R$_{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3{}^+$X$^-$, —N(OR—)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^g$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$alkyl)$_2$, —N(C$_{1-6}$alkyl)$_3$$^+$X$^-$, —NH(C$_{1-6}$ alkyl)$_2$$^+$X$^-$, —NH$_2$(C$_{1-6}$alkyl)$^+$X$^-$, —NH$_3$$^+$X$^-$, —N(OC$_{1-6}$alkyl)(C$_{1-6}$ alkyl), —N(OH)(C$_{1-6}$alkyl), —NH(OH), —SH, —SC$_{1-6}$ alkyl, —SS(C$_{1-6}$alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$alkyl), —C(=O)NH$_2$, —C(=O)N(C$_{1-6}$ alkyl)$_2$, —OC(=O)NH(C$_{1-6}$alkyl), —NHC(=O)(C$_{1-6}$ alkyl), —N(C$_{1-6}$alkyl)C(=O)(C$_{1-6}$ alkyl), —NHCO$_2$(C$_{1-6}$alkyl), —NHC(O)N(C$_{1-6}$ alkyl)$_2$, —NHC(=O)NH(C$_{1-6}$alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^9$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$_{aa}$, —SO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$, —C(=O)OR$^{X1}$, —C(=O)—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (—C(=O)$R^{aa}$), carboxylic acids (—CO$_2$H), aldehydes (—CHO), esters (—CO$_2R^{aa}$, —C(=O)S$R^{aa}$, —C(=S)S$R^{aa}$), amides (—C(=O)N($R^{bb}$)$_2$, —C(=O)N$R^{bb}$SO$_2R^{aa}$, —C(=S)N($R^{bb}$)$_2$), and imines (—C(=N$R^{bb}$)$R^{aa}$, —C(=N$R^{bb}$)O$R^{cc}$, —C(=N$R^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{bb}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$alkyl (e.g., aralkyl, heteroaralkyl), $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), p-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})$ $R^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo), —OR$^{aa}$ (when the O atom is attached to a carbonyl group, wherein R$^{aa}$ is as defined herein), —O(C=O)R$^{LG}$, or —O(SO)$_2$R$^{LG}$ (e.g., tosyl, mesyl, besyl), wherein R$^{LG}$ is optionally substituted alkyl, optionally substituted aryl, or optionally substituted heteroaryl. In some cases, the leaving group is a halogen. In some embodiments, the leaving group is I.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, idose, desosamine, and mycaminose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., 24) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an α anomer, the —OH substituent on the anomeric carbon rests on the opposite side (trans) of the ring from the —CH$_2$OH side branch. The alternative form, in which the —CH$_2$OH substituent and the anomeric hydroxyl are on the same side (cis) of the plane of the ring, is called a β anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, or rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

These and other exemplary substituents are described in more detail in the Detailed Description, Examples, and claims. The invention is not intended to be limited in any manner by the above exemplary listing of substituents.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, ethanoate, propanoate, benzoate, glycerate, lactate, tartrate, glycolate, and the like), $BF_4^-$, $PF_4^-$, $PF_6^-$, $AsF_6^-$, $SbF^-$, $B[3,5-(CF_3)_2C_6H_3]_4]^-$, $BPh_4^-$, $Al(OC(CF_3)_3)_4^-$, and a carborane anion (e.g., $CB_{11}H_{12}^-$ or $(HCB_{11}Me_5Br_6)^-$).

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "isotopically labeled derivative" refers to a compound wherein one or more atoms in the compound has been replaced with an isotope of the same element. For the given element or position in the molecule the isotope will be enriched, or present in a higher percentage of all atoms of the element or of all atoms at the position in the molecule in a sample, relative to an unlabeled sample. In certain embodiments, the enriched isotope will be a radioactive isotope (e.g., a radionuclide).

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Synthesis of D-Desosamine (1)

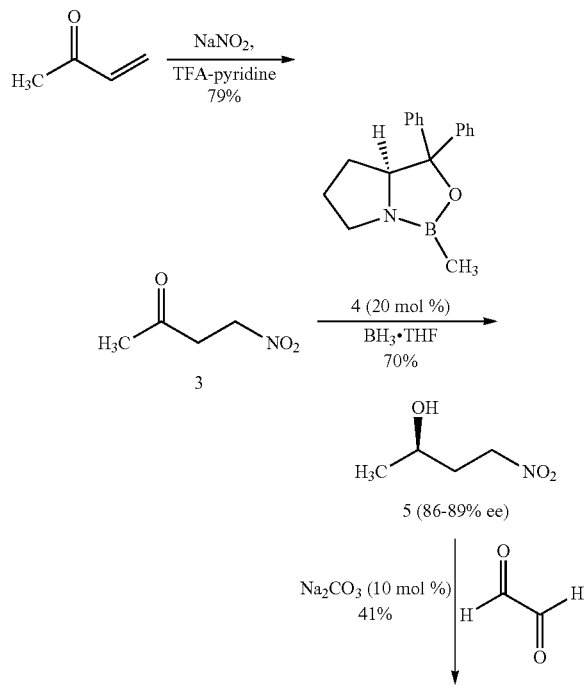

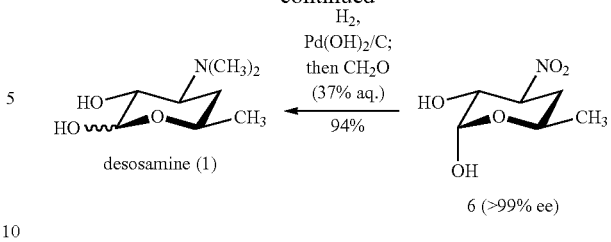

The optimized 4-step sequence to D-desosamine (1) is shown in Scheme E1, and begins with the transformation of methyl vinyl ketone to 4-nitro-2-butanone (3). Miyakoshi et al. have shown that conjugative addition of sodium nitrite to methyl vinyl ketone in a mixed solvent of acetic acid and THF provides 4-nitro-2-butanone in 82% yield. See, e.g., Miyakoshi et al., Chem. Lett.) (1981) 10:1677-1678; Miyakoshi et al., Nippon Kagaku Kaishi (1984) 1984:458-462. When we employed this method to prepare 3 we did successfully obtain the desired product, but it was contaminated with 4-acetoxy-2-butanone as a by-product (~4:1 ratio, respectively) and the mixture proved challenging to separate. A way to obviate this problem is substitution of pyridinium trifluoroacetate for acetic acid. Thus, addition of trifluoroacetic acid (86.0 mL, 1.30 equiv.) to a solution of pyridine (91.0 mL, 1.30 equiv.) in THF (1.0 L) at 0° C. over 10 minutes led to a suspension of pyridinium trifluoroacetate. Admixture of methyl vinyl ketone (60.0 g, 1 equiv.) with sodium nitrite (70.9 g, 1.20 equiv.) and this suspension at 23° C. for 16 hours followed by an extractive isolation procedure (ethyl acetate) afforded 4-nitro-2-butanone in a high state of purity in 50% yield (50.4 g). Yields as high as 79% have also been obtained by using self-prepared pyridinium trifluoroacetate and careful workup to account for the product being low boiling and highly water soluble. While it has been reported that 3 can be purified by distillation, we do not recommend this, as distillation may lead to decomposition (browning) with bumping, likely due to retro-Michael addition to form nitrous acid and methyl vinyl ketone. Because 3 is formed in a high state purity by the modified method, no further purification is necessary.

Slow addition of the "crude" ketone 3 to a mixture of the Corey-Bakshi-Shibata oxazaborolidine catalyst 4 (20 mol %) and borane-tetrahydrofuran complex (0.8 equiv.) afforded the secondary alcohol 5 in 65% yield (33.3 g) and 87% ee (Mosher ester analysis, See, e.g., Dale et al., J. Am. Chem. Soc. (1973) 95:512-519; Hoye et al., Nat. Protocols (2007) 2:2451:2458) after purification by extractive isolation (ethyl acetate) and distillation (1.2 mmHg, 80° C.). See, e.g., Corey et al., J. Am. Chem. Soc. (1987) 109:5551-5553; Angew. Chem. Int. Ed. (1998) 37:1986-2012. The use of a substoichiometric amount of borane and slow addition of the ketone led to reproducibly high enantioselectivities (86-89% ee). Yields as high as 70% have also been obtained. The aminoalcohol ligand (S)-1,1-diphenylprolinol was readily recovered (in 80% yield) from the reaction mixture by extraction with aqueous acid, neutralization, extraction with dichloromethane and recrystallization, and could be used to regenerate the catalyst 4 in one step.

In the cyclization step, a biphasic mixture of nitro alcohol 5 (33.3 g, 1 equiv., ~2.6 M in 3:1 dichloromethane:water), 40% aqueous glyoxal (42.6 mL, 1.05 equiv.) and sodium carbonate (1.5 g, 5 mol %) was stirred at 4° C. for 16 hours, leading to direct precipitation of the nitro sugar 6 from the reaction mixture. After filtration of the reaction solution through a sintered glass filter funnel, the product was obtained in pure form in 41% yield as a white powder (20.1 g). Chiral HPLC analysis established that the product was >99% ee, which is substantially higher than the ee of the starting nitro alcohol 5. Although further purification of 6 is unnecessary; if desired, it can be recrystallized from hot n-butanol (87% recovery). X-ray crystallographic analysis of crystals obtained from n-butanol confirmed the stereochemistry of the nitro sugar was homologous with D-desosamine. $^1$H NMR analysis of a CD$_3$OD solution of 6 showed a mixture of α and β anomers, ~15:1.

Completion of the synthesis was achieved wherein sequential nitro reduction and reductive amination were conducted in a single step. A suspension of 6 (15.0 g, 1 equiv.) and palladium hydroxide on carbon (20 wt. % loading, 6.0 g) in 9:1 methanol:acetic acid (420 mL) was stirred under H$_2$ (1 atm) at 23° C. Aqueous formaldehyde (37 wt. %, 15.8 mL, 2.50 equiv.) was added when TLC analysis indicated full consumption of starting material (typically in 8 hours), and the mixture was stirred for additional 12 hours. Filtration of the reaction solution through Celite, concentration of the filtrate and neutralization of the acetate salt with Amberlyst A26 resin afforded D-desosamine (1) as a colorless liquid in 94% yield. This process is amenable to large-scale synthesis, and we have prepared 20-g batches of D-desosamine in about 4 days.

4-nitrobutane-2-one (3)

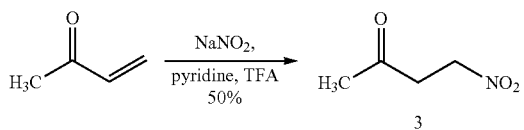

Trifluoroacetic acid (86.0 mL, 1.11 mol, 1.30 equiv) was added to a stirred mixture of pyridine (91.0 mL, 1.11 mol, 1.30 equiv) and THF (1000 mL) at 0° C. After 10 minutes, sodium nitrite (70.9 g, 1.03 mol, 1.20 equiv) and methyl vinyl ketone (60.0 g, 856 mmol, 1 equiv) were added. The reaction mixture was warmed to 23° C. and stirred for 18 hours. Water (700 mL) and ether (500 mL) were added and the layers were separated. The aqueous layer was extracted with ethyl acetate (7×300 mL). The combined organic layers were concentrated to ~500 mL, and washed with 1 N HCl (2×400 mL). The combined aqueous layers were extracted with ethyl acetate (5×300 mL). The combined organic layer was washed with half saturated aqueous sodium bicarbonate solution (300 mL). The aqueous layer was extracted with ethyl acetate (3×300 mL). The combined organic layers were washed with brine (300 mL), dried over magnesium sulfate, and concentrated to afford 4-nitrobutan-2-one (50.4 g, 50%). $^1$H NMR (500 MHz, CDCl$_3$) δ 4.63 (td, J=6.2, 2.4 Hz, 2H), 3.09 (t, J=6.0 Hz, 2H), 2.27 (d, J=2.3 Hz, 3H). $^{13}$C NMR (126 MHz, CDCl$_3$) δ 203.5, 68.8, 38.9, 29.7. FTIR (neat), cm$^{-1}$: 2924 (m), 1720 (s), 1554 (s), 1400 (s), 1375 (s), 1127 (s). HRMS (ESI): Calcd for (C$_4$H$_7$NO$_3$+Na)$^+$: 140.0318; Found: 140.0319.

(R)-4-nitrobutane-2-ol (5)

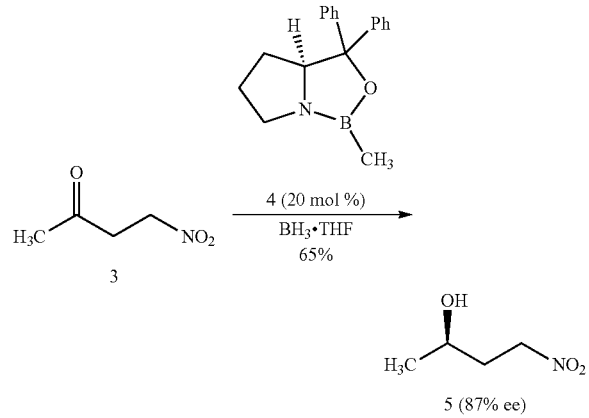

To a flame-dried flask was charged borane-tetrahydrofuran complex (1.0 M in THF, 344 mL, 344 mmol, 0.800 equiv) and THF (1.0 L). The solution was cooled to −10° C. (ice-salt bath) and (S)-1-methyl-3,3-diphenyltetrahydro-1H, 3H-pyrrolo[1,2-c][1,3,2]oxazaborole (86 mL, 86 mmol, 0.20 equiv) was added as a 1.0 M solution in toluene. A solution of 4-nitrobutan-2-one (50.4 g, 430 mmol) in THF (120 mL) was added dropwise over 60 minutes. The internal temperature was maintained at −10° C. over the course of addition. The reaction mixture was stirred at −10° C. After 30 minutes, methanol (150 mL) was added, and the mixture was vigorously stirred for 10 minutes. 1 N HCl (600 mL) was added and the mixture was stirred for additional 10 minutes. The mixture was extracted with ether (500 mL) followed by ethyl acetate (7×500 mL). The combined organic layers were dried over magnesium sulfate and concentrated. After concentration, the crude mixture was diluted with ether (500 mL) and filtered through a pad of Celite. The solution was washed with 1 N HCl (2×200 mL) and brine (200 mL). The aqueous acid layers were combined for the recovery of (S)-1,1-diphenylprolinol (vide infra). The organic layer was dried over magnesium sulfate and concentrated. The crude product was purified by distillation (1.2 mmHg, 80° C.) to give the title compound as pale yellow oil (33.3 g, 65%). $^1$H NMR (500 MHz, CDCl$_3$) δ 4.69-4.43 (m, 2H), 4.00-3.88 (m, 1H), 2.28-2.18 (m, 1H), 2.08-2.00 (m, 1H), 1.65 (br, 1H), 1.29 (d, J=6.2 Hz, 3H). $^{13}$C NMR (126 MHz, CDCl$_3$) δ 72.5, 64.9, 35.8, 23.7. FTIR (neat), cm$^{-1}$: 3389 (br), 2972 (m), 1548 (s), 1379 (s), 1130 (s), 1103 (s). HRMS (ESI): Calcd for (C$_4$H$_9$NO$_3$+Na)$^+$: 142.0475; Found: 142.0482.

Determination of Enantiomeric Excess:

Crude 5 (10 mg, 0.088 mmol, 1 equiv) was dissolved in dichloromethane (0.2 mL). Pyridine (14.0 μL, 0.168 mmol, 2.00 equiv) and (R)-(−)-MTPA acid chloride (42.5 mg, 0.168 mmol, 2.00 equiv) were added at 23° C. The solution was stirred for 1 hour and concentrated. $^1$H NMR was taken of the residue. Enantiomeric excess was calculated from integrations of methyl doublets at 1.42 ppm (desired) and 1.35 ppm (undesired). The ee of this sample was found to be 87%.

Recovery of (S)-1,1-diphenylprolinol

The combined acid layers were treated with 6 N NaOH until the pH reaches 13. The mixture was extracted with dichloromethane (3×500 mL). The combined organic layers were dried over magnesium sulfate and concentrated to give (S)-1,1-diphenylprolinol as a white solid. This solid was recrystallized from hot heptane (3 mL/g) to give the recovered amino alcohol as colorless crystals.

4-nitro-4,5,6-trideoxy-α-D-glucose (6)

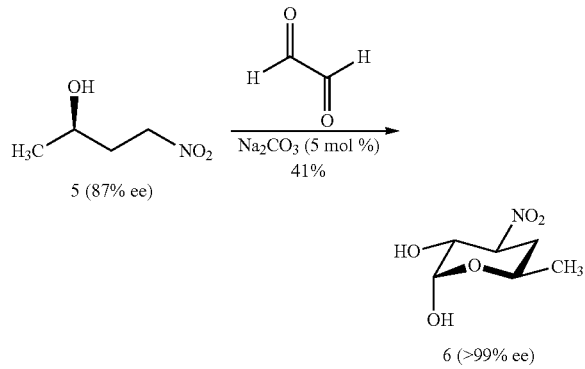

To the solution of sodium carbonate (1.48 g, 14.0 mmol, 0.0500 equiv) in water (28.0 mL) were added sequentially glyoxal (40 wt. % in water, 42.6 mL, 294 mmol, 1.05 equiv), (R)-4-nitrobutan-2-ol (5) (33.3 g, 280 mmol, 1 equiv, 87% ee) and dichloromethane (80 mL). The biphasic mixture was vigorously stirred at 4° C. for 16 hours. Ether (100 mL) was added to the reaction mixture. The reaction mixture was filtered through a sintered glass funnel. The filter cake was washed with ether (2×50 mL) and dried under vacuum to give the title compound as a white powder (20.1 g, 41%). $^1$H NMR (15:1 α:β anomeric mixture, 500 MHz, CD$_3$OD) α-anomer: δ 5.15 (d, J=3.5 Hz, 1H), 4.93-4.88 (m, 1H), 4.20 (dqd, J=12.5, 6.2, 2.2 Hz, 1H), 3.97 (dd, J=10.3, 3.6 Hz, 1H), 2.26 (ddd, J=12.4, 4.5, 2.3 Hz, 1H), 1.83 (app q, J=12.2 Hz, 1H), 1.20 (d, J=6.3 Hz, 3H). β-anomer: δ 4.65 (ddd, J=12.3, 10.0, 4.8 Hz, 1H), 4.49 (d, J=7.7 Hz, 1H), 3.77-3.70 (m, 1H), 3.68 (dd, J=10.0, 7.7 Hz, 1H), 2.30-2.20 (m, 1H), 1.83 (app q, J=12.4 Hz, 1H), 1.25 (d, J=6.2 Hz, 3H). $^{13}$C NMR (15:1 α:β anomeric mixture, 126 MHz, CD$_3$OD) α-anomer: δ 93.8, 86.3, 71.5, 63.3, 38.8, 20.9. β-anomer δ 97.9, 88.8, 73.7, 69.3, 39.0, 21.0. FTIR (neat), cm$^{-1}$: 3323 (br), 2933 (m), 2470 (s), 1720 (s), 1552 (s), 1384 (s), 1267 (s), 1155 (s), 1095 (s), 1039 (s). HRMS (ESI): Calcd for (C$_6$H$_{11}$NO$_5$+Na)$^+$: 200.0529; Found: 200.0517.

The product is pure by $^1$H NMR analysis. But if desired, it could be recrystallized from hot n-butanol (5.5 mL/g) to give the product as colorless crystals (15.0 g, 75% recovery).

Enantiomeric excess was determined by chiral HPLC (Chiralcel OC—H Column, Daicel Corp., Eluent: 10% iPrOH-Hexane, Detector Wavelength=210 nm). t$_R$ (major)=18.4 minutes, t$_R$ (minor)=22.8 minutes. Samples before and after recrystallization were both found to be have >99% ee.

D-Desosamine (1)

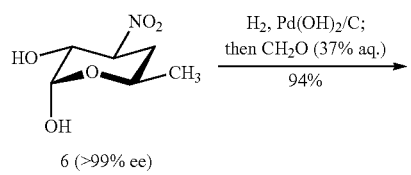

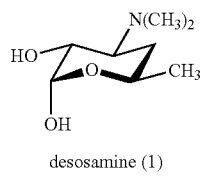

desosamine (1)

α:β ~ 1:1.6

4-nitro-4,5,6-trideoxy-α-D-glucose (6) (15.0 g, 85.0 mmol) was dissolved in 9:1 methanol:acetic acid (420 mL) in a 1-L flask. 20 wt. % Palladium hydroxide on carbon (5.95 g, 8.47 mmol) was added. The flask was evacuated and refilled with argon (3 times). The evacuation-refill cycle was repeated with hydrogen gas (2 times). The suspension was stirred at 23° C. under hydrogen atmosphere (balloon pressure) and the reaction progress was monitored by TLC (100% ether). After full consumption of starting material (typically in 8 hours), aqueous formaldehyde (37 wt. % in water, 15.8 mL, 212 mmol) was added. The mixture was kept stirred at 23° C. under hydrogen atmosphere for 15 hours. The mixture was filtered through a thin pad of Celite (~30 g), rinsing with methanol (~100 mL). The filtrate was concentrated and the residue was dissolved in methanol (300 mL). To the solution was added Amberlyst A26 resin (OH form, 300 g). The slurry was stirred at 23° C. for 1 hour, and filtered through a sintered glass funnel. The resin was rinsed with 300 mL methanol. The filtrate was concentrated to give D-desosamine (13.9 g, 94%, α:β~1:1.6). $^1$H NMR (1:1.6 α:β anomeric mixture, 500 MHz, CD$_3$OD) α-anomer: δ 5.09 (d, J=3.6 Hz, 1H), 4.12 (dqd, J=12.6, 6.1, 2.0 Hz, 1H), 3.53 (dd, J=10.6, 3.6 Hz, 1H), 2.96 (ddd, J=12.2, 10.7, 3.9 Hz, 1H), 2.34 (s, 6H), 1.81-1.72 (m, 1H), 1.30-1.22 (m, 1H), 1.14 (d, J=6.3 Hz, 3H). β-anomer: δ 4.41 (d, J=7.4 Hz, 1H), 3.61 (dqd, J=12.4, 6.2, 1.9 Hz, 1H), 3.20 (dd, J=10.2, 7.4 Hz, 1H), 2.61 (ddd, J=12.3, 10.3, 4.2 Hz, 1H), 2.33 (s, 6H), 1.76 (ddt, J=12.8, 4.2, 2.1 Hz, 1H), 1.28-1.19 (m, 1H), 1.22 (d, J=6.2 Hz, 3H). $^{13}$C NMR (1:1.6 α:β anomeric mixture, peaks are reported collectively, 126 MHz, CD$_3$OD) δ 99.3, 94.4, 72.9, 70.7, 70.5, 65.6, 65.2, 60.8, 40.8, 40.7, 33.0, 32.0, 21.5. FTIR (neat), cm$^{-1}$: 3399 (br), 2937 (m), 2486 (s), 2069 (s), 1556 (m), 1384 (m), 1120 (s), 1082 (s), 1042 (s), 980 (s). HRMS (ESI): Calcd for (C$_8$H$_{17}$NO$_3$+H)$^-$: 176.1281; Found: 176.1276.

Thioglycosidation of D-Desosamine

Scheme E2.

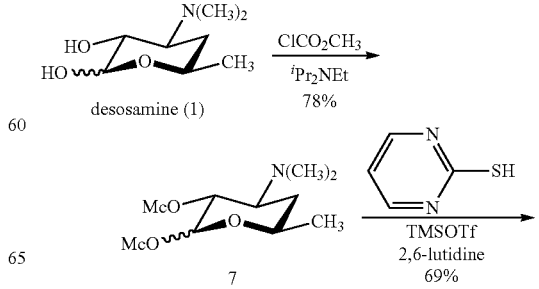

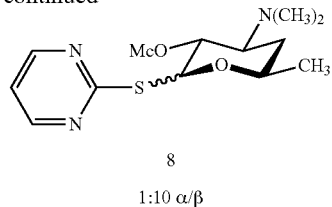

8

1:10 α/β

As shown in Scheme E2, D-Desosamine (1) can be transformed into the protected thioglycoside 8, an anomerically activated form of desosamine optimized for glycosidic coupling reactions by Woodward and coworkers in their landmark synthesis of erythromycin A. See, e.g., Woodward et al., *J. Am. Chem. Soc.* (1981) 103:3215-3217. The original Woodward procedure involved a Mitsunobu reaction (n-Bu3P, DEAD, 2-mercaptopyrimidine) for anomeric activation followed by protection of the free 2-hydroxyl group (ClCO2CH3/NaHCO3, 63% over 2 steps). Herein we describe a more practical as well as economical two-step transformation. Thus, treatment of D-desosamine (9.33 g, 1 equiv.) with methylchloroformate (12.4 mL, 3.00 equiv.) and diisopropylethylamine (27.9 mL, 3.00 equiv.) in dichloromethane (106 mL) at 0° C. for 1 hour led to formation of dimethyl biscarbonate 7 (12.0 g, 78%, α:β ~1:1.5). Addition of trimethylsilyl triflate (13.7 mL, 2.00 equiv.) to a mixture of 7 (11.0 g, 1 equiv.), 2-mercaptopyrimidine (4.24 g, 1.00 equiv.), 2,6-lutidine (8.8 mL, 2.00 equiv.) in dichloromethane (76 mL) followed by stirring for 19 hours at 4° C. afforded thioglycoside 8 (69%, α:β ~1:10) after purification by column chromatography.

D-desosamine-1,2-dimethyl biscarbonate (7)

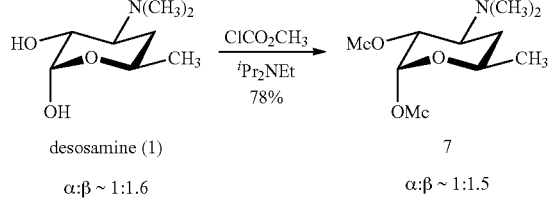

desosamine (1)

α:β ~ 1:1.6

7

α:β ~ 1:1.5

D-desosamine (9.33 g, 53.2 mmol) was dissolved in dichloromethane (106 mL) and cooled to 0° C. Hunig's Base (27.9 mL, 160 mmol) and methyl chloroformate (12.4 mL, 160 mmol) were added sequentially. After 1 hour, 100 mL saturated sodium bicarbonate solution was added to the reaction mixture. The resulting biphasic mixture was stirred for 5 minutes, and extracted with dichloromethane (3×100 mL). The combined organic layers were dried over sodium sulfate and concentrated. The residue was dissolved in ether (250 mL) and 1 N HCl (100 mL). The layers were separated and the ether layer was extracted with 1N HCl (2×50 mL). The combined aqueous layers were neutralized with solid sodium bicarbonate until pH=8. The milky aqueous mixture was extracted with ether (3×200 mL). The combined organic layers were dried over magnesium sulfate and concentrated to provide the title compound as a colorless oil (12.0 g, 78%, α:β~1:1.5). $^1$H NMR (1:1.5 α:β anomeric mixture, 500 MHz, CDCl$_3$) α-anomer: δ 6.17 (d, J=3.6 Hz, 1H), 4.85 (dd, J=11.1, 3.6 Hz, 1H), 4.14-4.05 (m, 1H), 3.83 (s, 3H), 3.81 (s, 3H), 3.20 (app td, J=11.8, 4.0 Hz, 1H), 2.32 (s, 6H), 1.87 (ddd, J=13.2, 3.9, 2.3 Hz, 1H), 1.45 (app q, J=10.8 Hz, 1H), 1.23 (d, J=6.2 Hz, 3H). β-anomer: δ 5.46 (d, J=7.9 Hz, 1H), 4.73 (dd, J=10.5, 7.9 Hz, 1H), 3.78-3.70 (m, 1H), 2.84 (ddd, J=12.3, 10.6, 4.3 Hz, 1H), 2.31 (s, 6H), 1.82 (ddd, J=13.3, 4.2, 1.9 Hz, 1H), 1.42 (app q, J=11.5 Hz, 1H), 1.30 (d, J=6.1 Hz, 3H). $^{13}$C NMR (1:1.5 α:β anomeric mixture, peaks are reported collectively, 126 MHz, CDCl$_3$) δ 155.0, 154.9, 154.4, 154.3, 96.9, 94.4, 77.2, 73.3, 72.5, 70.5, 67.3, 63.2, 57.6, 55.0, 55.0, 54.9, 40.6, 40.4, 31.3, 29.9, 21.0, 20.9. FTIR (neat), cm$^{-1}$: 2958 (m), 1751 (s), 1442 (s), 1274 (s), 1250 (s), 1084 (s), 979 (s). HRMS (ESI): Calcd for (C$_{12}$H$_{21}$NO$_7$+H)$^+$: 292.1391; Found: 292.1395.

Thioglycoside 8

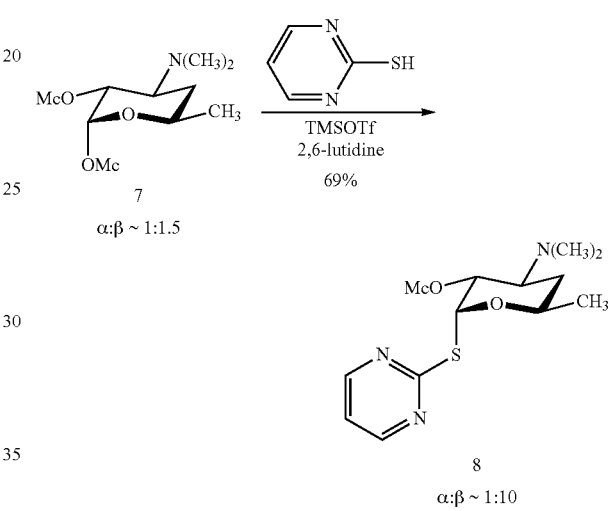

8

α:β ~ 1:10

2-mercaptopyrimidine (4.24 g, 37.8 mmol) and 2,6-lutidine (8.80 mL, 76 mmol) were added to a solution of D-desosamine-1,2-dimethyl biscarbonate (11.0 g, 37.8 mmol) in dichloromethane (76 mL). The mixture was cooled to 0° C. and trimethylsilyl trifluoromethanesulfonate (13.7 mL, 76 mmol) was added dropwise. After addition, the flask was transferred to a 4° C. cold room and stirred for 19 hours. Saturated sodium bicarbonate solution (200 mL) was added, and the biphasic mixture was vigorously stirred for 30 minutes (gas evolution). The layers were separated and the aqueous layer was extracted with dichloromethane (2×100 mL). The combined organic layers were dried over sodium sulfate and concentrated. The residue was purified by column chromatography over silica gel (30% acetone-hexanes) to afford the title compound as a yellow foam (8.5 g, 69%, α:β ~1:10). $^1$H NMR (1:10 α:β anomeric mixture, 500 MHz, CDCl$_3$) α-anomer: δ 8.53 (d, J=4.9 Hz, 3H), 6.98 (t, J=4.8 Hz, 1H), 6.76 (d, J=5.3 Hz, 1H), 5.07 (dd, J=11.1, 5.3 Hz, 1H), 3.73 (s, 3H), 3.04-2.96 (m, 1H), 2.33 (s, 6H), 1.86 (ddd, J=13.2, 4.3, 1.8 Hz, 1H), 1.49 (app td, J=12.6, 11.2 Hz, 1H), 1.21 (d, J=6.1 Hz, 3H). β-anomer: δ 8.51 (d, J=4.8 Hz, 2H), 6.98 (t, J=4.8 Hz, 1H), 5.69 (d, J=10.1 Hz, 1H), 4.85 (app t, J=10.1 Hz, 1H), 3.77 (s, 3H), 2.92 (ddd, J=12.4, 10.0, 4.3 Hz, 1H), 2.32 (s, 6H), 1.86 (ddd, J=13.2, 4.3, 1.8 Hz, 1H), 1.49 (app td, J=12.6, 11.2 Hz, 1H), 1.27 (d, J=6.2 Hz, 3H). $^{13}$C NMR (1:10 α:β anomeric mixture, β-anomer is reported, 126 MHz, CDCl$_3$) δ 170.2, 157.3, 117.1, 83.1, 73.7, 72.3, 64.8, 55.0, 40.7, 31.1, 21.3. FTIR (neat), cm$^{-1}$:

2974 (m), 1749 (s), 1550 (s), 1381 (s), 1274 (s), 1055 (s), 738 (s). HRMS (ESI): Calcd for $(C_{14}H_{21}N_3O_4S+H)^+$: 328.1326; Found: 328.1333.

Synthesis of Desosamine Analogs

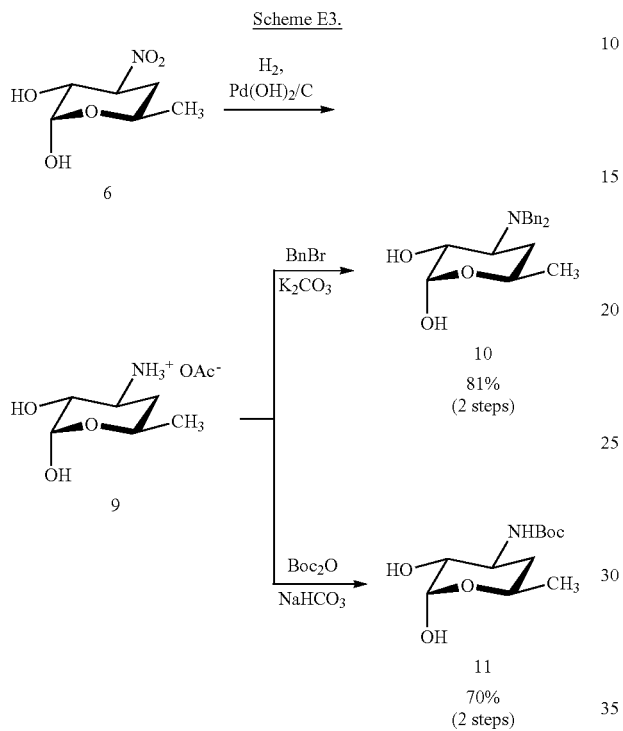

Scheme E3.

N-protected derivatives of desosamine can be readily accessed (Scheme E3) from the acetate salt of primary amine 9, which in turn was prepared from catalytic hydrogenation of nitro sugar 6 following the protocol described for desosamine in the absence of formaldehyde. Heating a mixture of 9 (100 mg, 1 equiv.), potassium carbonate (267 mg, 4.00 equiv.) and benzyl bromide (115 µL, 2.00 equiv.) at 80° C. for 1 hour led to formation of N,N-dibenzyl derivative 10 (136 mg, 81%). Treatment of 9 (415 mg, 1 equiv.) with di-tert-butyl dicarbonate (446 µL, 1.20 equiv.) and sodium bicarbonate (538 mg, 4.00 equiv.) afforded N-tert-butoxycarbonyl derivative 11 (278 mg, 70%).

4-amino-4,5,6-trideoxy-D-glucose hydroacetate (9)

4-nitro-4,5,6-trideoxy-α-D-glucose (1.72 g, 9.71 mmol) was dissolved in 9:1 MeOH/AcOH (48 mL). 20 wt. % Palladium hydroxide on carbon (682 mg, 8.47 mmol) was added. The flask was evacuated and refilled with argon (3 times). The evacuation-refill cycle was repeated with hydrogen gas (2 times). The suspension was stirred at 23° C. under hydrogen atmosphere (balloon pressure) and the reaction progress was monitored by TLC (100% ether). After 6 hours, The mixture was filtered through a thin pad of celite and washed with methanol (~50 mL) The filtrate was concentrated to afford the title compound as an orange oil (2.01 g, 100%).

4-dibenzylamino-4,5,6-trideoxy-D-glucose (10)

4-amino-4,5,6-trideoxy-D-glucose hydroacetate (100 mg, 0.483 mmol) was dissolved in 2:1 ethanol/water (1.0 mL). Potassium carbonate (267 mg, 1.93 mmol) and benzyl bromide (115 µL, 0.965 mmol) were added sequentially. The biphasic mixture was heated to 80° C. for 1 hour. The reaction mixture was cooled to 23° C., diluted with water (2 mL), and extracted with ether (3×5 mL). The combined ether layers were washed with brine and dried over magnesium sulfate. The solution was filtered and concentrated. The residue was dissolved in ether (10 mL) and the solution was extracted with 1 N HCl (3×1 mL). The ether layer was discarded, and the combined acid layers were neutralized with solid sodium bicarbonate to pH=8. The mixture was extracted with dichloromethane (3×5 mL). The combined organic layer were dried over sodium sulfate and concentrated to provide the title compound as a pale yellow oil (136 mg, 81%, α:β ~1:2.0). $^1$H NMR (500 MHz, CDCl$_3$) α-anomer: δ 5.33 (d, J=3.5 Hz, 1H), 4.16-4.03 (m, 1H), 3.87 (d, J=13.3 Hz, 2H), 3.66 (dd, J=10.5, 3.6 Hz, 1H), 3.45 (d, J=13.4 Hz, 2H), 3.09 (ddd, J=12.2, 10.7, 3.6 Hz, 1H), 1.96-1.80 (m, 1H), 1.50-1.36 (m, 1H), 1.24 (d, J=6.2 Hz, 3H). β-anomer: δ 4.42 (d, J=7.2 Hz, 2H), 3.89 (d, J=13.3 Hz, 2H), 3.58-3.50 (m, 1H), 3.41 (d, J=13.5 Hz, 2H), 3.40 (dd, J=10.1, 7.2 Hz, 1H), 2.68 (ddd, J=12.4, 10.3, 3.9 Hz, 1H), 1.96-1.80 (m, 1H), 1.50-1.36 (m, 1H), 1.31 (d, J=6.2 Hz, 3H). $^{13}$C NMR (1:2.0 α:β anomeric mixture, peaks are reported collectively, 126 MHz, CDCl$_3$) δ 140.0, 139.1, 139.0, 128.8, 128.7, 128.5, 128.5, 128.3, 128.1, 127.3, 127.2, 126.9, 97.8, 92.4, 71.2, 69.8, 68.1, 65.3, 59.6, 55.4, 53.7, 53.6, 53.0, 30.8, 30.3, 21.3. FTIR (neat), cm$^{-1}$: 3419 (br), 2920 (m), 1454 (s), 1045 (s), 738 (s), 698 (s). HRMS (ESI): Calcd for $(C_{20}H_{25}NO_3+H)^+$: 328.1914; Found: 328.1907.

Scheme E4.

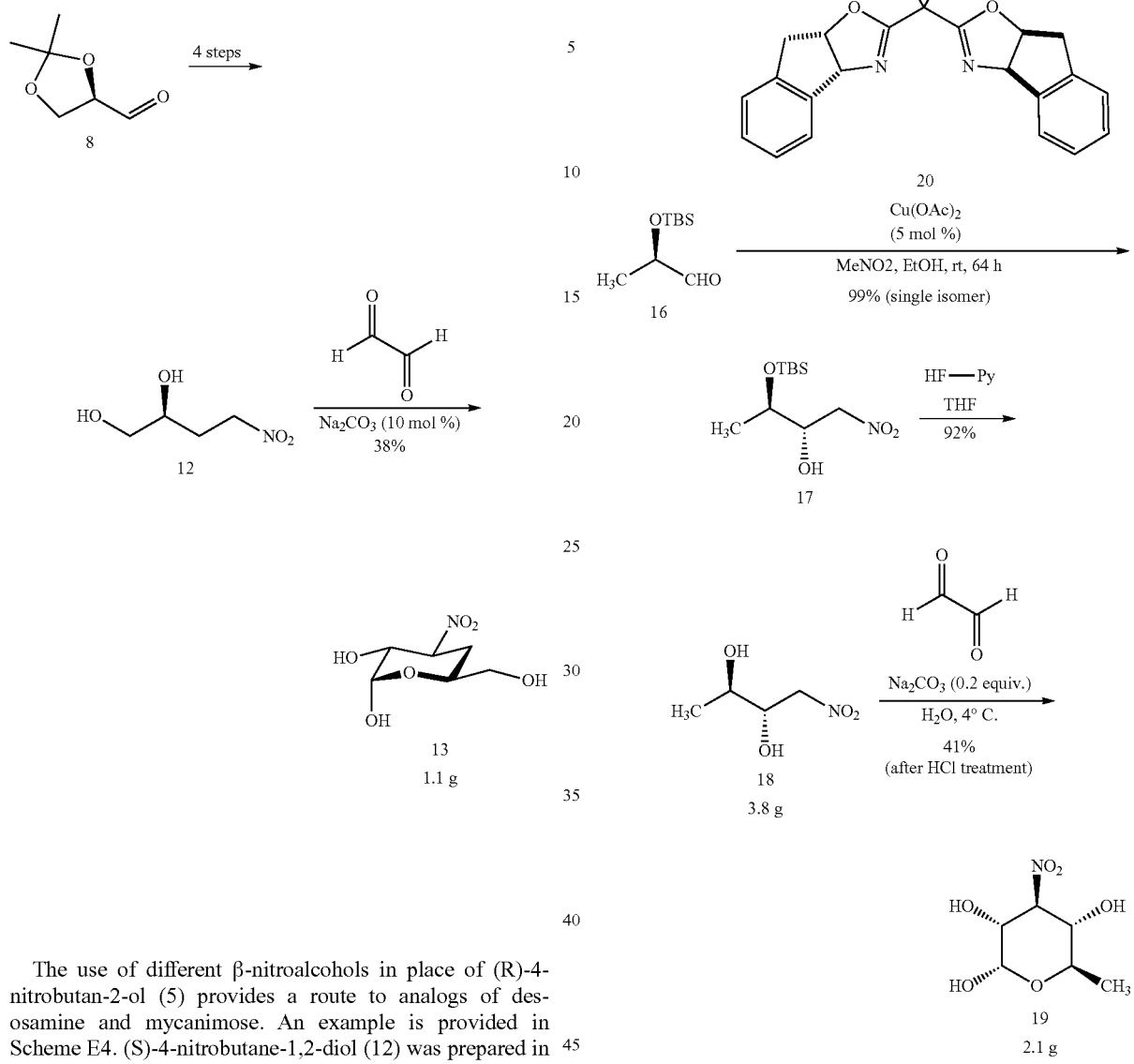

The use of different β-nitroalcohols in place of (R)-4-nitrobutan-2-ol (5) provides a route to analogs of desosamine and mycanimose. An example is provided in Scheme E4. (S)-4-nitrobutane-1,2-diol (12) was prepared in 4 steps from (R)-glyceraldehyde acetonide (8), following a procedure described in Zindel et al. (*J. Org. Chem.* (1995) 60:2968-2973). Diol 12 underwent coupling with 40% aqueous glyoxal to give 13 in 38% yield. Although in this case precipitates did not appear in the reaction mixture, cyclization product 13 was obtained as white, needle-shaped crystals when the crude product was treated with hot n-butanol (0.6 mL/mmol) and cooled to 23° C. The nitro sugar 13 can be converted to a desosamine analog according to methods described in Scheme E1.

Scheme E5.

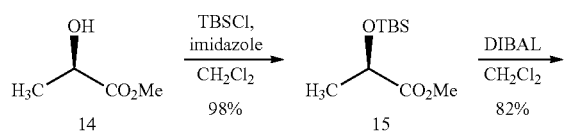

The synthesis of a 4-hydroxy nitro sugar is described in Scheme E5. Methyl (R)-2-hydroxypropanoate (14) was treated with tert-butyldimethylsilyl chloride and imidazole to afford the silyl protected alcohol 15 (98% yield), which was then reduced to aldehyde 16 in 82% yield. An asymmetric copper catalyzed Henry reaction to couple 16 and nitromethane employed the chiral bis(oxazaline) derivative 20, and formed the protected nitro diol 17 in 99% yield as a single isomer. Deprotection to give (2S,3R)-1-nitrobutane-2,3-diol (18) in 92% yield was accomplished by treatment with pyridinium hydrofluoride. Cyclization of diol 18 with glyoxal yields the 4-hydroxy nitro sugar (19) as an anomeric mixture. Initial precipitation gave only the α-anomer in 29% yield. Treatment of the mother liquor with HCl-dioxane promotes epimerization of the less crystalline β-anomer providing a second crop of the α-anomer and bringing the overall yield to 41%. Nitro sugar 19 can be converted to D-mycaminose via the reduction and methylation step described in Scheme E1.

Scheme E6.

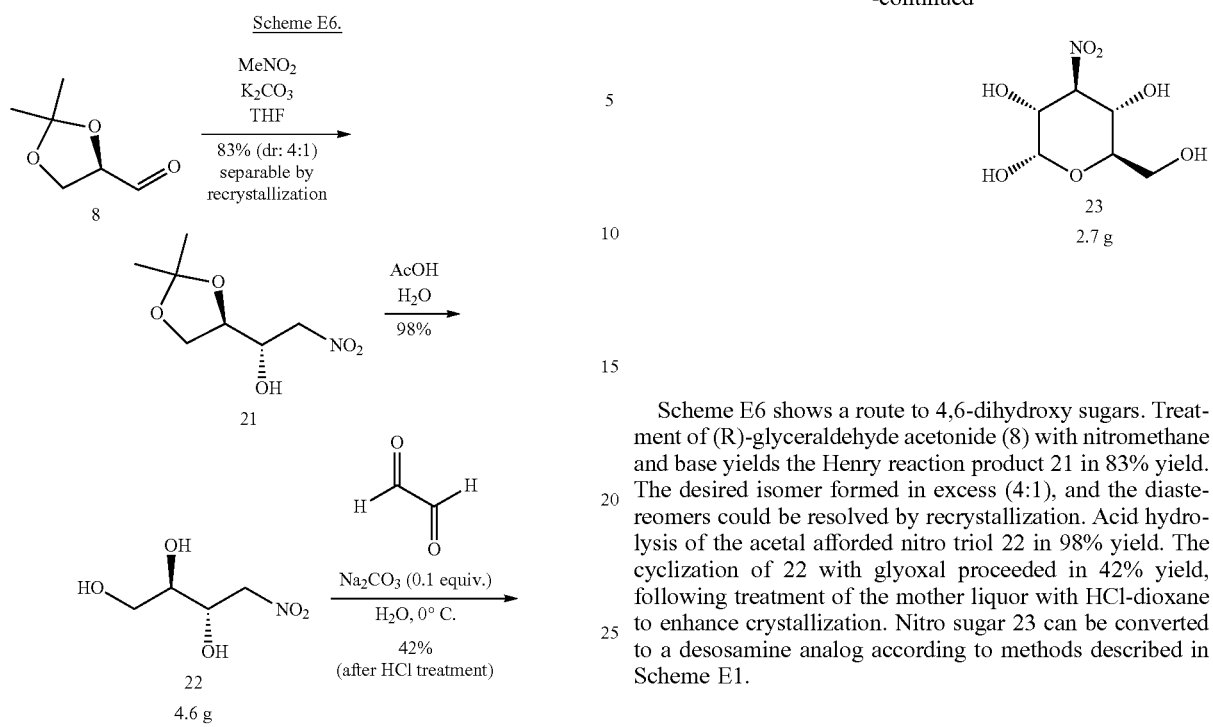

Scheme E6 shows a route to 4,6-dihydroxy sugars. Treatment of (R)-glyceraldehyde acetonide (8) with nitromethane and base yields the Henry reaction product 21 in 83% yield. The desired isomer formed in excess (4:1), and the diastereomers could be resolved by recrystallization. Acid hydrolysis of the acetal afforded nitro triol 22 in 98% yield. The cyclization of 22 with glyoxal proceeded in 42% yield, following treatment of the mother liquor with HCl-dioxane to enhance crystallization. Nitro sugar 23 can be converted to a desosamine analog according to methods described in Scheme E1.

Synthesis of 6-azido-D-desosamine Derivatives

Scheme E7.

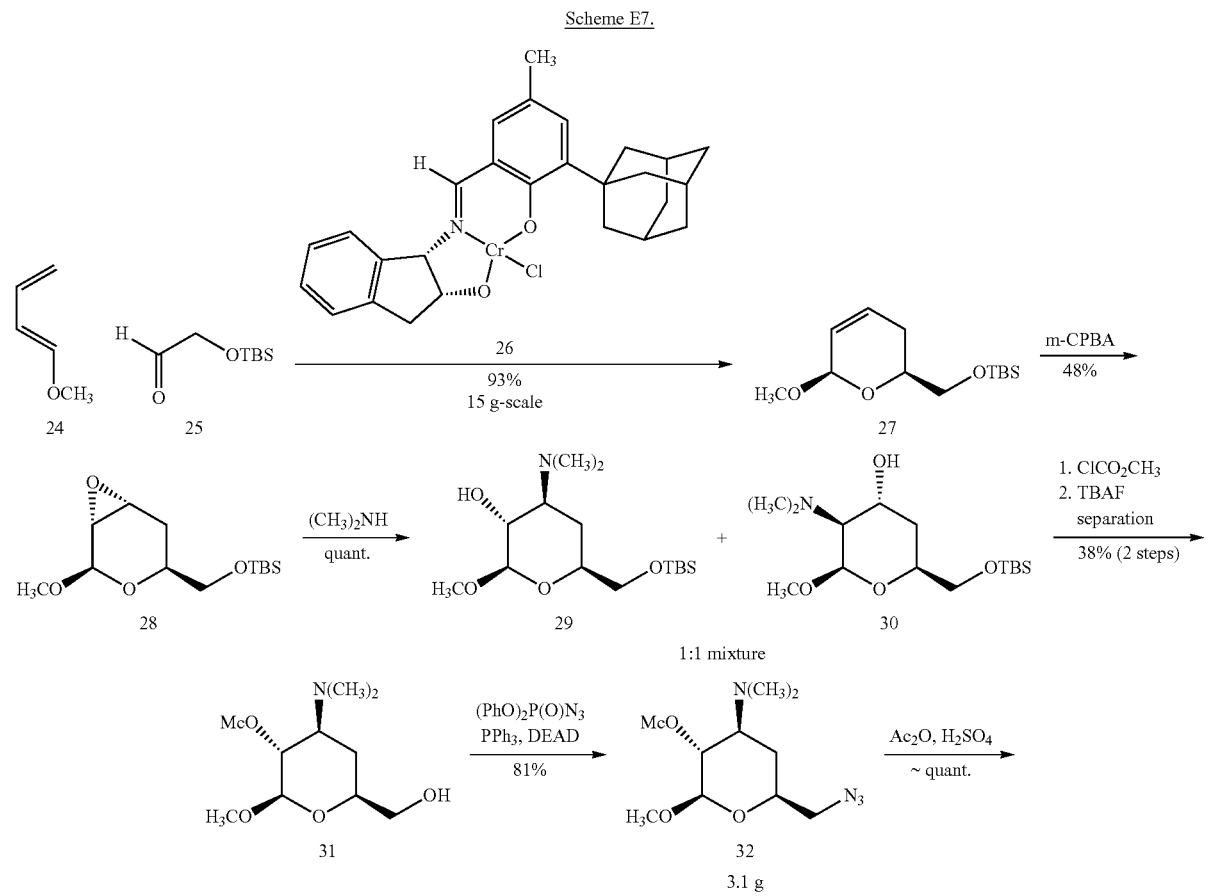

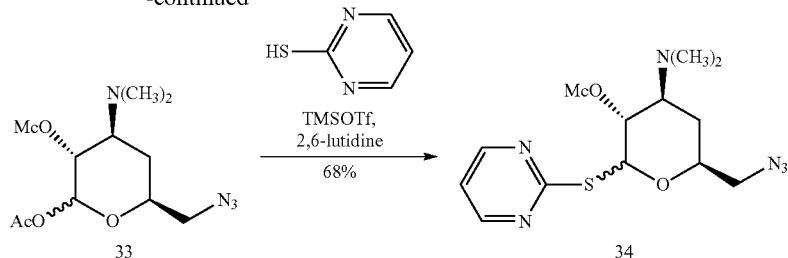

6-azido D-desosamine derivatives can be accessed as described in Scheme E7. The synthesis of methyl 2-O-methoxycarbonyl-3,4-dideoxy-3-dimethylamino-β-D-xylo-hexopyranoside (31) was adapted from procedures described by Roy and co-workers. See, e.g., Giguere et al., J. Org. Chem. (2011) 76:9687-9698. Methoxycarbonyl chloride was used in place of acetic anhydride in the step of protecting the C2 hydroxyl position. From intermediate 31 a Mitsunobu reaction with diphenylphosphoryl azide (DPPA) yields the protected 6-azido D-desosamine derivative 32 in 81% yield. Deprotection of both hydroxyl groups would provide 6-azido D-desosamine.

32 was converted to the protected thioglycoside in two additional steps. Treatment with acetic anhydride quantitatively converts the anomeric methoxy position to acetoxy. The acetoxy group of 33 is a suitable leaving group for thioglycosidation, which was carried out with mercaptopyrimidine, trimethylsilyl triflate and 2,6-lutidine to yield thioglycoside 34 in 68% yield.

Preparation of Nitro Sugars Bearing an Axial Substituent at 4-Position

Methods described herein are also applicable to the preparation of sugars bearing axial groups at the 4-position of the sugars. For example, a single 1-g-scale reaction, coupling of (2S,3S)-4-nitrobutane-1,2,3-triol and glyoxal afforded the crystalline nitrosugar shown in Scheme E8 27% yield. Examination of its NMR spectrum indicated that this nitrosugar differs from compound 23 in that the 4-hydroxy group adopts an axial configuration. In addition, when the 3-hydroxy group was protected as a benzhydryl ether as shown in Scheme E8, the cyclization reaction afforded the corresponding protected nitro sugar in 58% yield after purification by column chromatography.

(S)-1-((R)-2,2-dimethyl-1,3-dioxolan-4-yl)-2-nitroethan-1-ol (S4) and (R)-1-((R)-2,2-dimethyl-1,3-dioxolan-4-yl)-2-nitroethan-1-ol (S5)

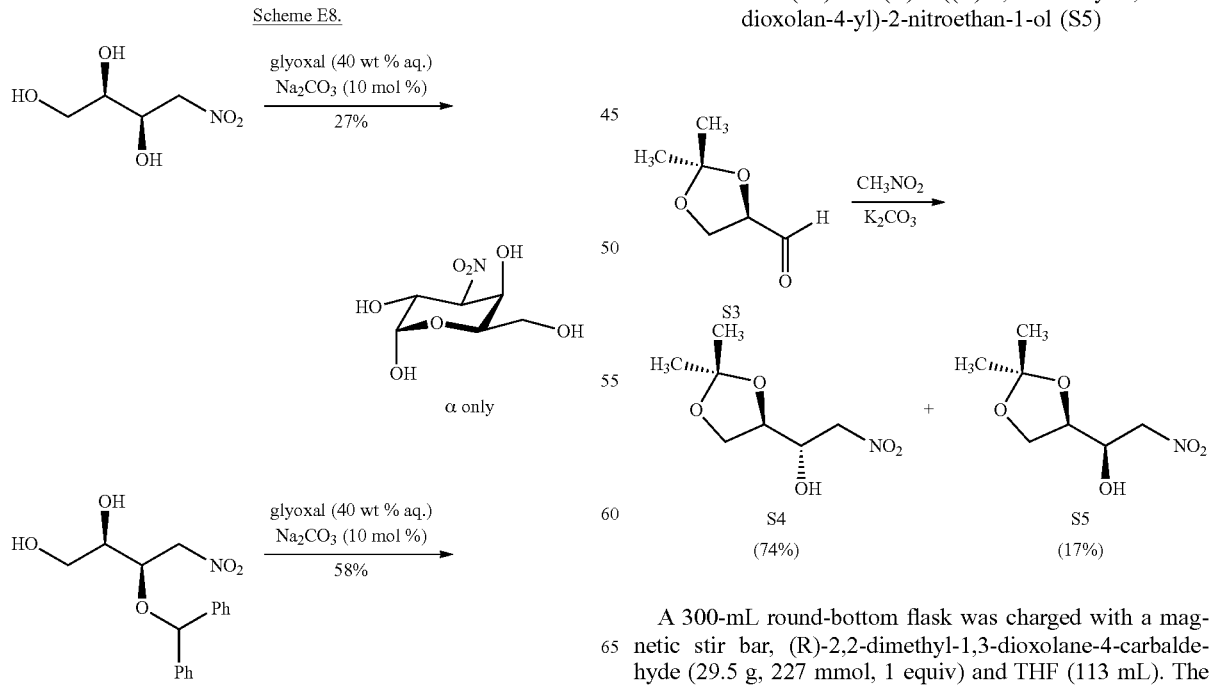

A 300-mL round-bottom flask was charged with a magnetic stir bar, (R)-2,2-dimethyl-1,3-dioxolane-4-carbaldehyde (29.5 g, 227 mmol, 1 equiv) and THF (113 mL). The mixture was cooled to 0° C., and nitromethane (36.7 mL, 680 mmol, 3.00 equiv) and solid potassium carbonate (40.7 g, 295 mmol, 1.30 equiv) were added. The reaction mixture was stirred at 23° C. for 18 h. Water (100 mL) was added and the mixture was extracted with ether (2×100 mL). The combined organic layers were washed with brine (200 mL). The washed solution was dried over magnesium sulfate, and the dried solution was concentrated. The residue was purified by column chromatography over silica gel (30% ethyl acetate-hexanes) to afford separately (S)-1-((R)-2,2-dimethyl-1,3-dioxolan-4-yl)-2-nitroethan-1-ol (S4) (32.2 g, 74%) and (R)-1-((R)-2,2-dimethyl-1,3-dioxolan-4-yl)-2-nitroethan-1-ol (S5) (7.32 g, 17%).

(S)-1-((R)-2,2-dimethyl-1,3-dioxolan-4-yl)-2-nitroethan-1-ol (S4)

TLC (30% ethyl acetate-hexanes): $R_f$=0.20 (phosphomolybdic acid). $^1$H NMR (500 MHz, CDCl$_3$) δ 4.72 (dd, J=13.2, 2.6 Hz, 1H), 4.47 (dd, J=13.2, 8.8 Hz, 1H), 4.27-4.21 (m, 1H), 4.18-4.14 (m, 1H), 4.06-3.99 (m, 2H), 2.78 (dd, J=5.4 Hz, 1H), 1.45 (s, 3H), 1.36 (s, 3H). $^{13}$C NMR (126 MHz, CD$_3$OD) δ 110.3, 78.0, 75.4, 70.2, 66.8, 26.7, 24.9. FTIR (neat), cm$^{-1}$: 3437 (br), 2990 (m), 2938 (m), 2897 (m), 1555 (s), 1375 (s), 1215 (s), 1153 (s), 1063 (s), 843 (s). HRMS (ESI): Calcd for (C$_7$H$_{13}$NO$_5$+Na)$^+$: 214.0686, Found: 214.0686.

(R)-1-((R)-2,2-dimethyl-1,3-dioxolan-4-yl)-2-nitroethan-1-ol (S5)

TLC (30% ethyl acetate-hexanes): $R_f$=0.15 (phosphomolybdic acid). $^1$H NMR (500 MHz, CDCl$_3$) δ 4.55 (dd, J=13.2, 8.8 Hz, 1H), 4.51 (dd, J=13.2, 3.9 Hz, 1H), 4.41-4.35 (m, 1H), 4.21 (ddd, J=6.8, 5.8, 2.9 Hz, 1H), 4.12 (dd, J=8.8, 6.8 Hz, 1H), 4.00 (dd, J=8.8, 5.8 Hz, 1H), 2.55 (d, J=7.8 Hz, 1H), 1.49 (s, 3H), 1.38 (s, 3H). $^{13}$C NMR (126 MHz, CD$_3$OD) δ 110.2, 78.3, 75.2, 68.4, 65.4, 26.2, 24.7. FTIR (neat), cm$^{-1}$: 3441 (br), 2990 (m), 2938 (m), 2897 (m), 1553 (s), 1375 (s), 1211 (s), 1154 (s), 1138 (s), 1063 (s), 845 (s). HRMS (ESI): Calcd for (C$_7$H$_{13}$NO$_5$+Na)$^+$: 214.0686, Found: 214.0691.

(2R,3R)-4-nitrobutane-1,2,3-triol (S6)

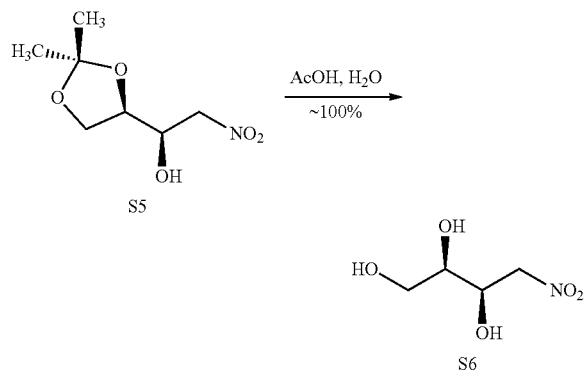

A 300-mL round-bottom flask was charged with a magnetic stir bar, (R)-1-((R)-2,2-dimethyl-1,3-dioxolan-4-yl)-2-nitroethan-1-ol S5 (4.16 g, 21.8 mmol, 1 equiv), acetic acid (54.4 mL) and water (18.1 mL). The reaction mixture was heated at 70° C. for 1 h with stirring. After cooling to 23° C., the product solution was concentrated under reduced pressure to afford the title compound as a colorless solid (3.28 g, ~100%). TLC (ethyl acetate): $R_f$=0.37 (p-anisaldehyde). $^1$H NMR (500 MHz, CD$_3$OD) δ 4.67 (dd, J=12.7, 2.9 Hz, 1H), 4.57 (dd, J=12.7, 9.8 Hz, 1H), 4.44-4.39 (m, 1H), 3.70-3.58 (m, 2H), 2.62-2.58 (m, 2H), 2.02-1.97 (m, 1H). $^{13}$C NMR (126 MHz, CD$_3$OD) δ 80.0, 73.3, 70.3, 63.5. FTIR (neat), cm$^{-1}$: 3389 (br), 2930 (m), 2496 (m), 1547 (s), 1424 (s), 1385 (s), 1219 (s), 1078 (s), 1038 (s). HRMS (ESI): Calcd for (C$_4$H$_9$NO$_5$+Na)$^+$: 174.0373, Found: 174.0362.

3-Nitro-3-deoxy-α-ᴠ-galactose (S7)

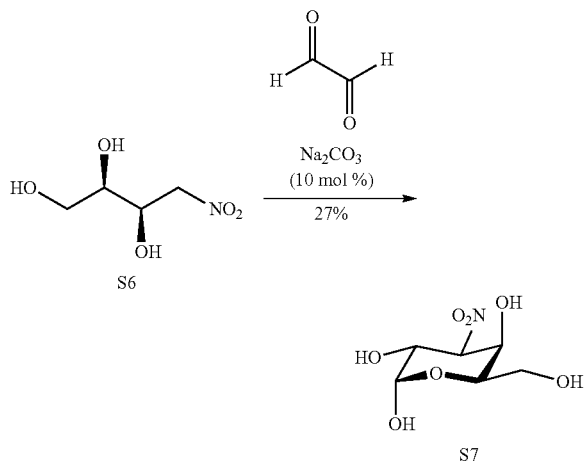

A 50-mL round-bottom flask was charged with a magnetic stir bar, (2R,3R)-4-nitrobutane-1,2,3-triol S6 (775 mg, 5.13 mmol) and water (1.03 mL). The solution was cooled to 0° C. Aqueous glyoxal solution (40 wt. %, 0.706 mL, 6.15 mmol, 1.20 equiv) and an aqueous solution of sodium carbonate (1.0 M, 0.513 mL, 0.513 mmol, 0.10 equiv) were added sequentially via syringe. After 2 h at 0° C., sufficient 1 N HCl was added to the product solution to achieve pH 7. The solution was then concentrated under reduced pressure. The oil residue was diluted with 5:1 ethyl acetate:methanol (10 mL), and the resulting solution was filtered through a thin pad of silica-gel (5 g). The filter cake was rinsed with 5:1 ethyl acetate:methanol (40 mL). The filtrate was concentrated and the residue was diluted with 1:1 toluene:isopropanol (20 mL). After stirring for 16 h at 23° C., the solution was concentrated under a stream of nitrogen, and the solid residue was triturated with 5:1 ethyl acetate:isopropanol (20 mL) with sonication. The resulting suspension was filtered through a sintered glass funnel (medium porosity), and the filter cake was rinsed with 5:1 ethyl acetate:isopropanol (5 mL). Further drying of the collected solids at reduced pressure (0.2 mmHg) afforded the title compound as an off white powder (290 mg, 27%). TLC (100% ethyl acetate): $R_f$=0.21 (p-anisaldehyde). Mp=132-134° C. $^1$H NMR (α-anomer, 500 MHz, CD$_3$OD) δ 5.22 (d, J=3.9 Hz, 1H), 4.79 (dd, J=10.7, 3.4 Hz, 1H), 4.48 (dd, J=10.7, 3.9 Hz, 1H), 4.40 (dd, J=3.4, 1.5 Hz, 1H), 4.12 (app t, J=6.4 Hz, 1H), 3.71 (dd, J=11.2, 6.4 Hz, 1H), 3.66 (dd, J=11.2, 6.4 Hz, 1H). $^{13}$C NMR (α-anomer, 126 MHz, CD$_3$OD) δ 93.7, 88.8, 71.0, 66.9, 65.9, 62.0. FTIR (neat), cm$^{-1}$: 3354 (br), 2942 (m), 2481 (m), 1715 (s), 1553 (s), 1375 (s), 1148 (s), 1051 (s), 976 (s). HRMS (ESI): Calcd for (C$_6$H$_{11}$NO$_7$+Na)$^+$: 232.0428, Found: 232.0421.

(R)-4-((R)-1-(benzhydryloxy)-2-nitroethyl)-2,2-dimethyl-1,3-dioxolane (S8)

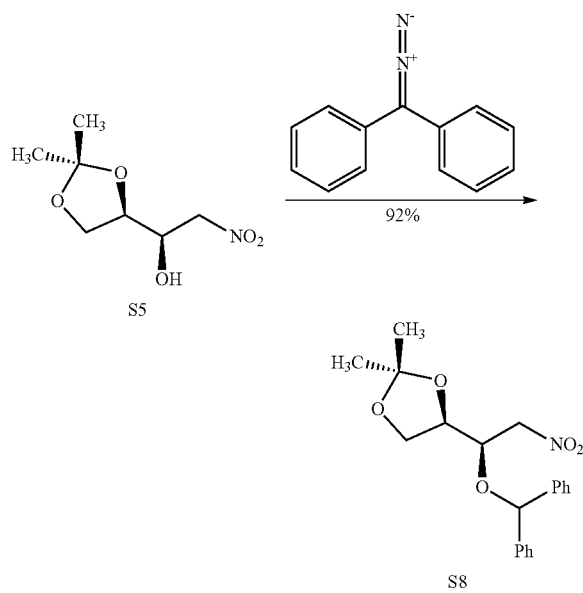

A 200-mL round-bottom flask was charged with a magnetic stir bar, (R)-1-((R)-2,2-dimethyl-1,3-dioxolan-4-yl)-2-nitroethan-1-ol S5 (934 mg, 4.89 mmol, 1 equiv) and toluene (48.9 mL). (Diazomethylene)dibenzene (1.90 g, 9.77 mmol, 2.00 equiv) was added, affording a purple solution. The reaction mixture was heated at reflux with stirring. After 1 h, the purple color had changed to yellow. The solution was cooled to 23° C. and then was concentrated under reduced pressure. The residue was purified by column chromatography over silica gel (30% ethyl acetate-hexanes) to afford the title compound as a white solid (1.60 g, 92%). TLC (20% ethyl acetate-hexanes): $R_f$=0.30 (UV, phosphomolybdic acid). $^1$H NMR (500 MHz, CDCl$_3$) δ 7.40-7.26 (m, 10H), 5.61 (s, 1H), 4.64 (dd, J=12.7, 3.9 Hz, 1H), 4.57 (dd, J=12.7, 8.3 Hz, 1H), 4.53-4.47 (m, 1H), 4.23-4.19 (m, 1H), 4.00-3.94 (m, 2H), 1.45 (s, 3H), 1.31 (s, 3H). $^{13}$C NMR (126 MHz, CDCl$_3$) δ 141.3, 141.0, 128.6, 128.4, 128.1, 127.8, 127.3, 126.9, 109.9, 83.7, 75.8, 74.4, 74.1, 64.7, 26.0, 24.3. FTIR (neat), cm$^{-1}$: 3063 (m), 3030 (m), 2988 (m), 2936 (m), 2895 (m), 1555 (s), 1495 (s), 1454 (s), 1261 (s), 1213 (s), 1155 (s), 1059 (s), 920 (s), 742 (s), 696 (s). HRMS (ESI): Calcd for (C$_{20}$H$_{23}$NO$_5$+Na)$^+$: 380.1468, Found: 380.0451.

(2R,3R)-3-(benzhydryloxy)-4-nitrobutane-1,2-diol (S9)

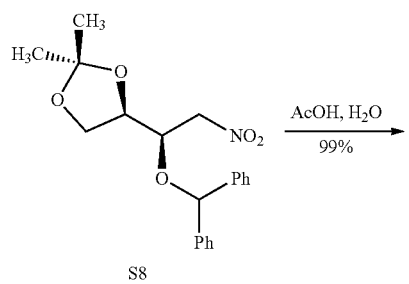

A 200-mL round-bottom flask was charged with a magnetic stir bar, (R)-4-((R)-1-(benzhydryloxy)-2-nitroethyl)-2,2-dimethyl-1,3-dioxolane S8 (1.60 g, 4.48 mmol, 1 equiv), acetic acid (11.19 ml) and water (3.73 ml). The resulting solution was heated at 70° C. for 1 h with stirring. After cooling to 23° C., the reaction mixture was concentrated under reduced pressure to afford the title compound as a colorless oil (1.40 g, 99%). TLC (50% ethyl acetate-hexanes): $R_f$=0.21 (UV, phosphomolybdic acid). $^1$H NMR (500 MHz, CDCl$_3$) δ 7.41-7.27 (m, 10H), 5.57 (s, 1H), 4.71 (dd, J=12.7, 4.4 Hz, 1H), 4.63 (dd, J=12.7, 6.8 Hz, 1H), 4.39 (dt, J=6.8, 4.4 Hz, 1H), 3.81-3.75 (m, 1H), 3.68-3.63 (m, 1H), 2.62-2.58 (m, 2H), 2.02-1.97 (m, 1H). $^{13}$C NMR (126 MHz, CDCl$_3$) δ 140.8, 140.7, 128.8, 128.5, 128.3, 127.9, 127.4, 126.8, 83.7, 76.0, 75.1, 71.1, 62.6. FTIR (neat), cm$^{-1}$: 3553 (br), 3422 (br), 3063 (m), 3030 (m), 2928 (m), 2889 (m), 1553 (s), 1495 (s), 1454 (s), 1424 (s), 1381 (s), 1076 (s), 918 (s), 743 (s), 698 (s). HRMS (ESI): Calcd for (C$_{17}$H$_{19}$NO$_5$+Na)$^+$: 340.1155, Found: 340.1167.

3-Nitro-3-deoxy-4-O-benzhydryl-v-galactose (S10)

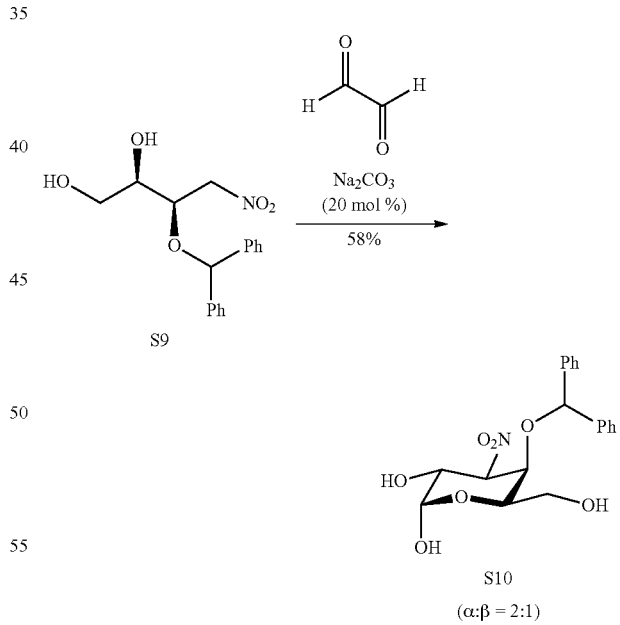

(α:β = 2:1)

A 50-mL round-bottom flask was charged with a magnetic stir bar, (2R,3R)-3-(benzhydryloxy)-4-nitrobutane-1,2-diol S9 (1.00 g, 3.15 mmol, 1 equiv), dichloromethane (1.38 mL) and water (0.63 mL). The solution was cooled to 0° C. Aqueous glyoxal solution (40 wt. %, 0.434 mL, 3.78 mmol, 1.20 equiv) and an aqueous solution of sodium carbonate (1.0 M, 0.315 mL, 0.315 mmol, 0.10 equiv) were added sequentially via syringe. The resulting biphasic mixture was stirred vigorously at 4° C. After 18 h, brine (20 mL) was added and the mixture was extracted with ethyl acetate (3×20 mL). The combined organic layers were dried over magnesium sulfate, and the dried solution was concentrated. The residue was purified by column chromatography over silica gel (70% ethyl acetate-hexanes) to afford the title compound as a white amorphous solid (2:1 anomeric mixture, 684 mg, 58%). TLC (100% ethyl acetate): $R_f$=0.21 (p-anisaldehyde). $^1$H NMR (2:1 α:β anomeric mixture, 500 MHz, CD$_3$OD) α-anomer: δ 7.36-7.22 (m, 10H), 5.49 (s, 1H), 5.28 (d, J=3.9 Hz, 1H), 4.74 (dd, J=10.7, 2.9 Hz, 1H), 4.64 (dd, J=10.7, 3.9 Hz, 1H), 4.48 (dd, J=2.9 Hz, 1H), 4.12 (d, J=6.8 Hz, 1H), 3.59 (dd, J=11.2, 6.8 Hz, 1H), 3.35-3.30 (m, 1H). β-anomer: δ 7.36-7.22 (m, 10H), 5.48 (s, 1H), 4.58 (dd, J=10.7, 3.4 Hz, 1H), 4.54 (d, J=7.8 Hz, 1H), 4.44 (dd, J=3.4 Hz, 1H), 4.35 (dd, J=10.7, 7.8 Hz, 1H), 3.68-3.62 (m, 2H), 3.35-3.30 (m, 1H). $^{13}$C NMR (2:1 α:β anomeric mixture, peaks are reported collectively, 126 MHz, CD$_3$OD) δ 143.3, 142.5, 129.2, 128.8, 128.7, 128.6, 128.3, 128.2, 93.6, 90.1, 87.4, 85.0, 84.9, 77.7, 74.6, 74.2, 71.7, 69.5, 66.4, 61.9. FTIR (neat), cm$^1$: 3402 (br), 3065 (m), 3030 (m), 2982 (m), 2942 (m), 1736 (s), 1709 (s), 1495 (s), 1454 (s), 1373 (s), 1244 (s), 1142 (s), 1076 (s), 1042 (s), 1009 (s), 743 (s), 698 (s). HRMS (ESI): Calcd for $(C_{19}H_{21}NO_7+Na)^+$: 398.1210, Found: 398.1227.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (J):

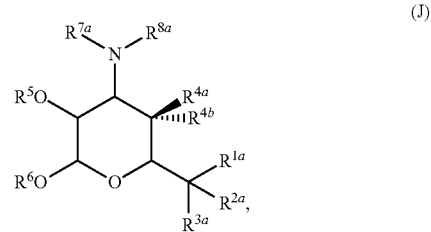

or salt thereof, wherein:
R$^{1a}$ is —N(R$^S$)$_2$, —NR$^S$(OR$^S$), or of formula:

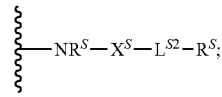

each of R$^{2a}$ and R$^{3a}$ is independently hydrogen, halogen, optionally substituted C$_1$-C$_6$ alkyl, or —OR$^{SO}$;
X$^S$ is a bond, —C(=O)—, —C(=NR$^{SN}$)—, —S(=O)—, or —S(=O)$_2$—;
L$^{S2}$ is a bond, —NR$^S$—, —O—, or —S—, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;
each R$^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two $R^S$ attached to the same nitrogen atom are taken together to form $=N_2$ or an optionally substituted heterocyclyl or heteroaryl ring;

each of $R^{7a}$ and $R^{8a}$ is independently optionally substituted $C_1$-$C_6$ alkyl, optionally substituted carbocyclyl, optionally substituted aryl, optionally substituted heterocyclyl, optionally substituted heteroaryl, optionally substituted acyl, or a nitrogen protecting group, or $R^{7a}$ and $R^{8a}$ are joined to form an optionally substituted heterocyclyl or heteroaryl ring;

each $R^{SN}$ is independently hydrogen, optionally substituted $C_1$-$C_6$ alkyl, or a nitrogen protecting group, or two $R^{SN}$ attached to the same nitrogen atom are joined to form an optionally substituted heterocyclyl or heteroaryl ring;

each of $R^{4a}$ and $R^{4b}$ is independently hydrogen, halogen, optionally substituted $C_1$-$C_6$ alkyl, or $-OR^{SO}$; and each of $R^5$, $R^6$ and $R^{SO}$ is independently hydrogen, optionally substituted $C_1$-$C_6$ alkyl, a carbohydrate, or an oxygen protecting group;

provided $R^{1a}$ is not:

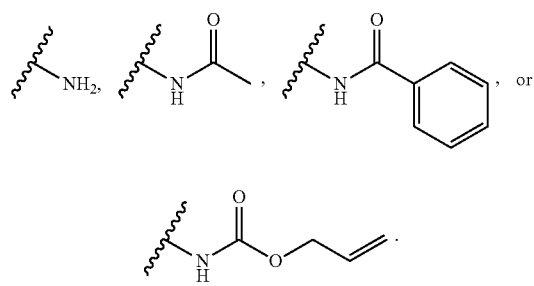

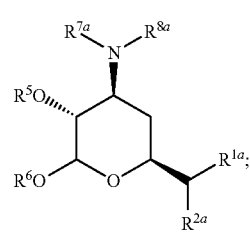

2. The compound of claim 1, wherein the compound is of Formula (J-1), (J-d-1), (J-m-1), or (J-m-1-A):

(J-1)

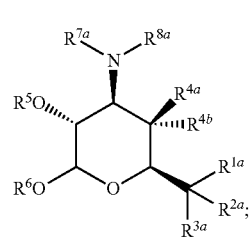

(J-d-1)

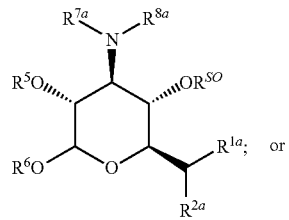

(J-m-1)

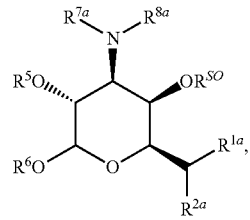

(J-m-1-A)

or salt thereof.

3. The compound of claim 1, or salt thereof, wherein $R^{7a}$ and $R^{8a}$ are methyl.

4. The compound of claim 1, or salt thereof, wherein $R^{2a}$ is hydrogen or methyl.

5. The compound of claim 1, or salt thereof, wherein $R^{1a}$ is $-N(R^S)_2$.

6. The compound of claim 5, or salt thereof, wherein $R^{1a}$ is:

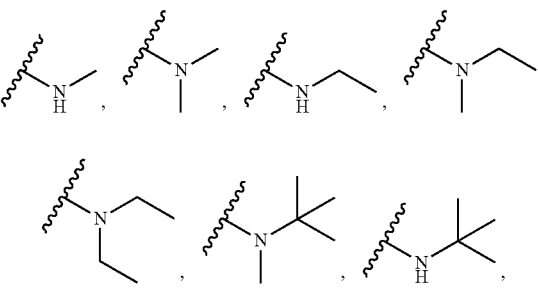

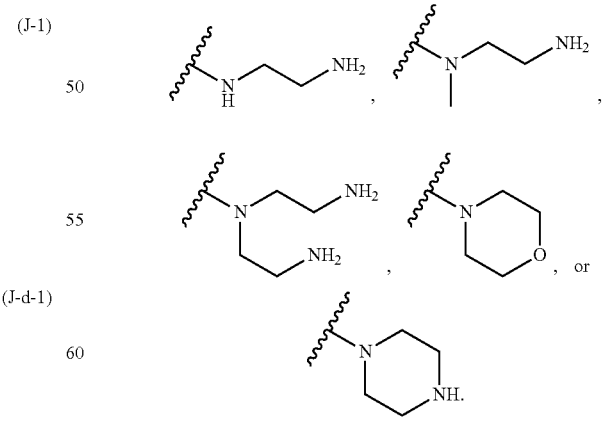

7. The compound of claim 1, or salt thereof, wherein $R^{1a}$ is $-NHC(=O)R^S$, $-NHC(=O)OR^S$, or $-NHC(=O)N(R^S)_2$.

8. The compound of claim 7, or salt thereof, wherein $R^{1a}$ is:

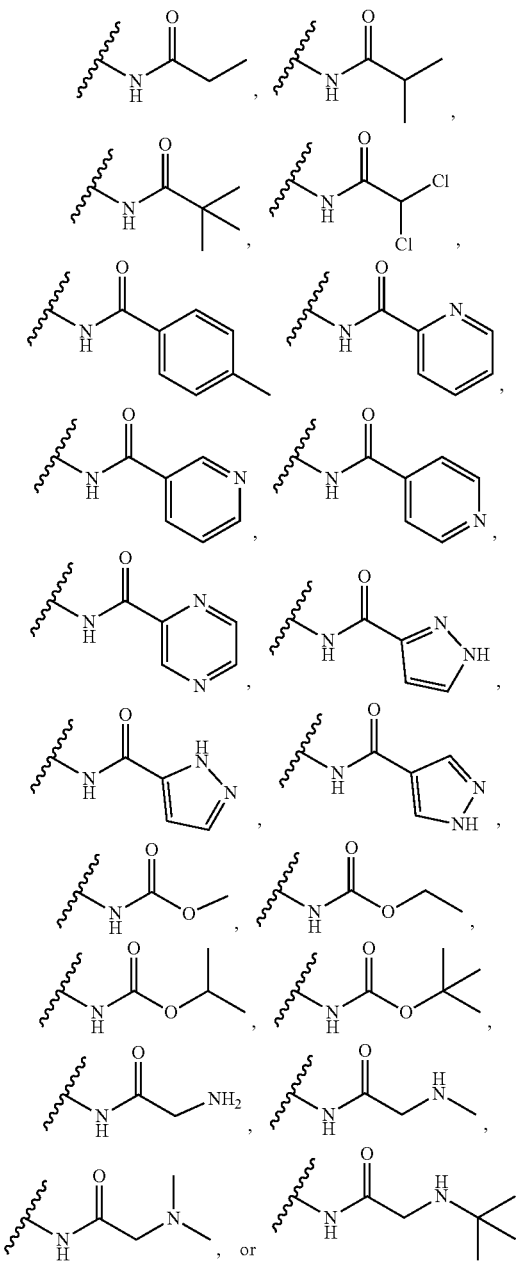

9. The compound of claim 1, or salt thereof, wherein $R^{1a}$ is —NHC(=NR$^{SN}$)R$^S$, —NHC(=NR$^{SN}$)OR$^S$, —NHC(=NR$^{SN}$)N(R$^S$)$_2$, or —NHS(=O)$_2$R$^S$.

10. The compound of claim 9, or salt thereof, wherein $R^{1a}$ is:

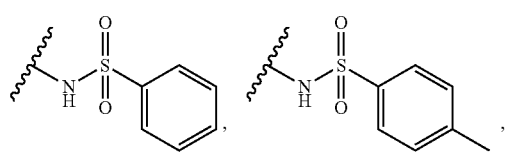

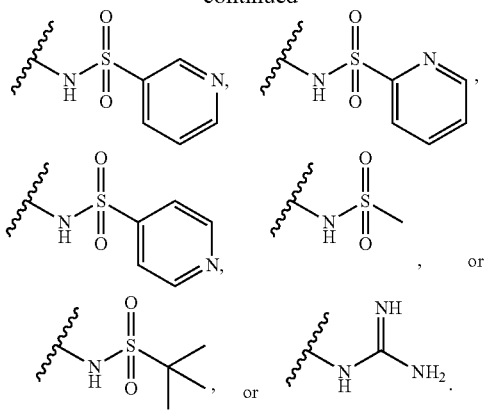

11. A compound of Formula (K):

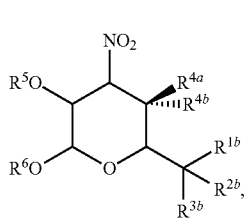

or salt thereof, wherein:
$R^{1b}$ is —N(R$^S$)$_2$, —NR$^S$(OR$^S$), or of formula:

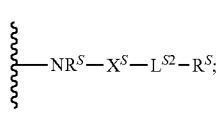

each of $R^{2b}$ and $R^{3b}$ is independently hydrogen, halogen, optionally substituted $C_1$-$C_6$ alkyl, or —OR$^{SO}$;
$X^S$ is a bond, —C(=O)—, —C(=NR$^{SN}$)—, —S(=O)—, or —S(=O)$_2$—;
$L^{S2}$ is a bond, —NR$^S$—, —O—, or —S—, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;
each R$^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two R$^S$ attached to the same nitrogen atom are taken together to form =N$_2$ or an optionally substituted heterocyclyl or heteroaryl ring;
R$^{SN}$ is hydrogen, optionally substituted alkyl, or a nitrogen protecting group;

each of $R^{4a}$ and $R^{4b}$ is independently hydrogen, optionally substituted $C_1$-$C_6$ alkyl, or —$OR^{SO}$; and each of $R^5$, $R^6$ and $R^{SO}$ is independently hydrogen, halogen, optionally substituted $C_1$-$C_6$ alkyl, a carbohydrate, or an oxygen protecting group;

provided $R^{1b}$ is not:

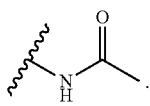

12. The compound of claim 11, wherein the compound is of Formula (K-1), (K-d-1), (K-m-1), (K-m-1-A):

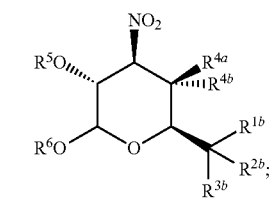

(K-1)

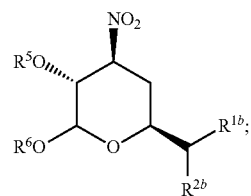

(K-d-1)

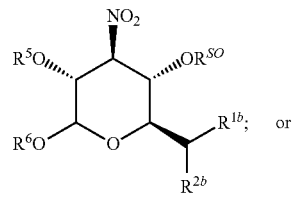

(K-m-1)

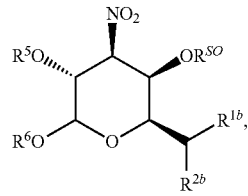

(K-m-1-A)

or salt thereof.

13. The compound of claim 11, or salt thereof, wherein $R^{2b}$ is hydrogen or methyl.

14. The compound of claim 11, or salt thereof, wherein $R^{1b}$ is —$N(R^S)_2$.

15. The compound of claim 14, or salt thereof, wherein $R^{1b}$ is:

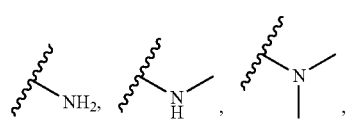

-continued

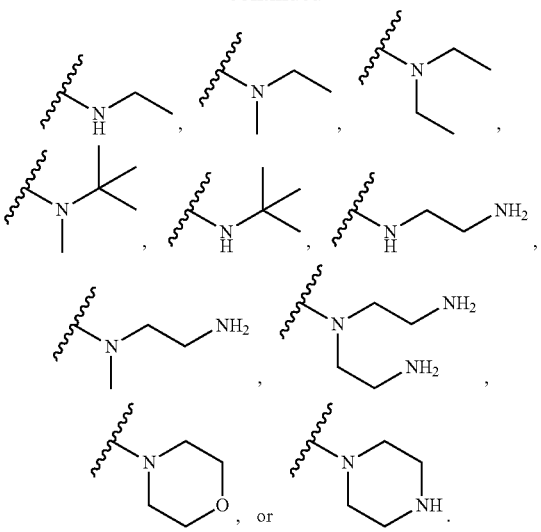

16. The compound of claim 11, or salt thereof, wherein $R^{1b}$ is —NHC(=O)$R^S$, —NHC(=O)O$R^S$, or —NHC(=O)N($R^S$)$_2$.

17. The compound of claim 16, or salt thereof, wherein $R^{1b}$ is:

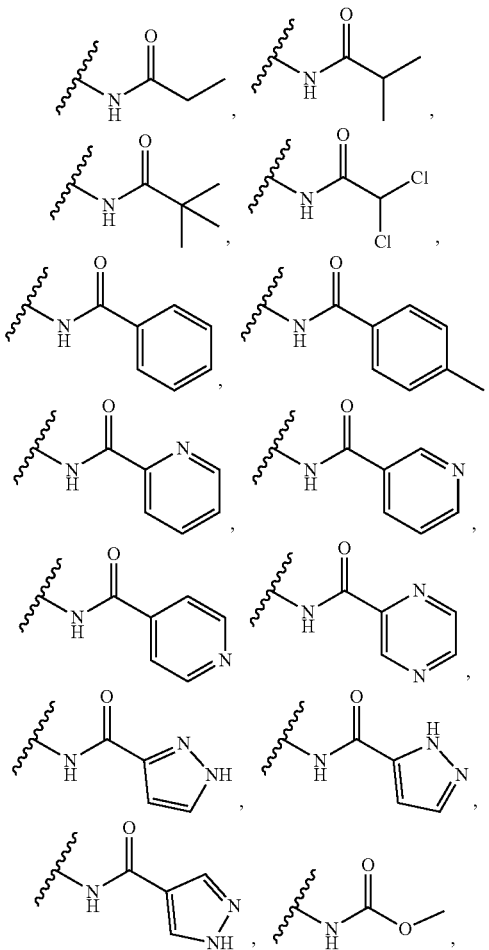

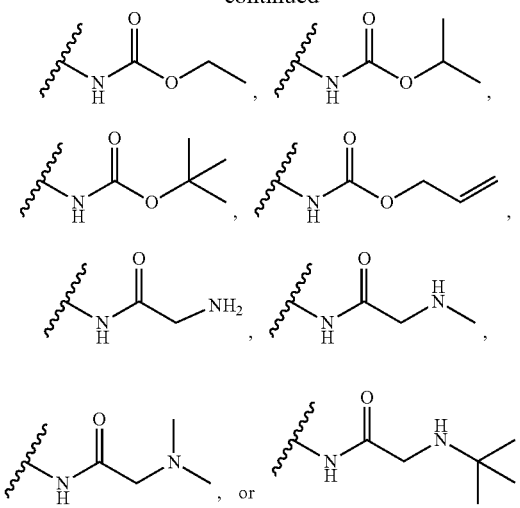
18. The compound of claim 11, or salt thereof, wherein $R^{1b}$ is —NHC(=NR$^{SN}$)R$^S$, —NHC(=NR$^{SN}$)OR$^S$, or —NHC(=NR$^{SN}$)N(R$^S$)$_2$.
19. The compound of claim 11, or salt thereof, wherein $R^{1b}$ is —NHS(=O)$_2$R$^S$.
20. The compound of claim 11, or salt thereof, wherein $R^{1b}$ is:
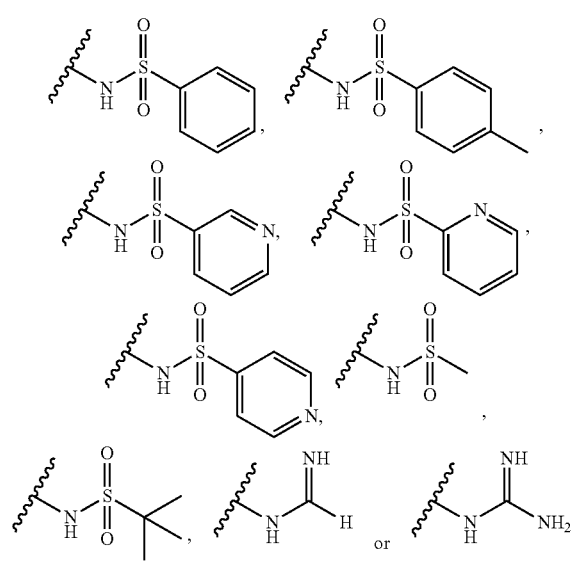
* * * * *